US 6,521,654 B2

(12) United States Patent
Wehner et al.

(10) Patent No.: US 6,521,654 B2
(45) Date of Patent: Feb. 18, 2003

(54) SUBSTITUTED IMIDAZOLIDINE DERIVATIVES, THEIR PREPARATION, THEIR USE AND PHARMACEUTICAL PREPARATIONS INCLUDING THEM

(75) Inventors: Volkmar Wehner, Sandberg (DE); Hans Ulrich Stilz, Frankfurt (DE); Wolfgang Schmidt, Frankfurt (DE); Dirk Seiffge, Mainz-Kostheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/952,028

(22) Filed: Sep. 14, 2001

(65) Prior Publication Data

US 2002/0143043 A1 Oct. 3, 2002

Related U.S. Application Data

(62) Division of application No. 09/516,587, filed on Mar. 1, 2000, now Pat. No. 6,331,552, which is a continuation of application No. 09/195,440, filed on Nov. 18, 1998, now abandoned.

(30) Foreign Application Priority Data

Nov. 19, 1997 (DE) ......................... 197 51 251

(51) Int. Cl.$^7$ ............... A61K 31/4166; A61K 31/4178; C07D 233/72; C07D 407/12

(52) U.S. Cl. .................. 514/389; 514/391; 548/311.7; 548/319.5

(58) Field of Search .................. 548/311.7, 319.5; 514/389, 391

(56) References Cited

U.S. PATENT DOCUMENTS

| | | | |
|---|---|---|---|
| 4,344,949 A | 8/1982 | Hoefle et al. | 424/258 |
| 4,350,704 A | 9/1982 | Hoefle et al. | 424/274 |
| 4,374,847 A | 2/1983 | Gruenfeld | 424/274 |
| 5,389,614 A | 2/1995 | Koenig et al. | 514/18 |
| 5,397,796 A | 3/1995 | Zoller et al. | 514/389 |
| 5,424,293 A | 6/1995 | Zoller et al. | 514/20 |
| 5,554,594 A | 9/1996 | Zoller et al. | 514/18 |
| 5,658,935 A | 8/1997 | Klinger et al. | 514/359 |
| 5,686,421 A | 11/1997 | Koenig et al. | 514/18 |
| 5,998,447 A | * 12/1999 | Stilz et al. | 514/341 |

FOREIGN PATENT DOCUMENTS

| | | |
|---|---|---|
| DE | 235 866 | 5/1986 |
| EP | 0 029 488 | 6/1981 |
| EP | 0 031 741 | 7/1981 |
| EP | 0 046 953 | 3/1982 |
| EP | 0 049 605 | 4/1982 |
| EP | 0 049 658 | 4/1982 |
| EP | 0 050 800 | 5/1982 |
| EP | 0 052 870 | 6/1982 |
| EP | 0 079 022 | 5/1983 |
| EP | 0 084 164 | 7/1983 |
| EP | 0 089 637 | 9/1983 |
| EP | 0 090 341 | 10/1983 |
| EP | 0 090 362 | 10/1983 |
| EP | 0 105 102 | 4/1984 |
| EP | 0 109 020 | 5/1984 |
| EP | 0 111 873 | 6/1984 |
| EP | 0 271 865 | 6/1988 |
| EP | 0 344 682 | 12/1989 |
| EP | 0 449 079 | 10/1991 |
| EP | 0 796 855 | 9/1997 |
| EP | 0 842 943 | 11/1997 |
| EP | 0 842 944 | 11/1997 |
| EP | 0 842 945 | 11/1997 |

(List continued on next page.)

OTHER PUBLICATIONS

Cronstein, Bruce N. et al., "The Adhesion Molecules of Inflammation", *Arthritis and Rheumatism*, vol. 36(2); pp. 147–157(1993).A52.

Elices, Mariano J. et al., "VCAM–1 on Activated Endothelium Interacts with the Leukocyte Integrin VLA–4 at a Site Distinct from the VLA–4/Fibronectin Binding Site", *Cell*, vol. 60; pp. 577–584(1990).

Foster, Carolyn A. et al., "VCAM–1/α4–integrin adhesion pathway: Therapeutic target for allergic inflammatory disorders", *Jour. Allergy Clin. Immunol.*, vol. 96(6); pp. S270–S277(1996).

(List continued on next page.)

*Primary Examiner*—Rona T. Powers

(57) ABSTRACT

Substituted imidazolidine derivatives of the formula I, $$\text{(I)}$$

in which B, E, W, Y, R, $R^2$, $R^3$, $R^{30}$, e and h have the meanings indicated in the claims. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leucocytes and/or antagonists of the adhesion receptor VLA-4 belonging to the integrins group. They are generally suitable for the therapy or prophylaxis of illnesses which are caused by an undesired extent of leucocyte adhesion and/or leucocyte migration or are associated therewith, or in which cell-cell or cell-matrix interactions which are based on interactions of VLA-4 receptors with their ligands play a part. The invention furthermore relates to processes for the preparation of the compounds of the formula I, their use, in particular as pharmaceutical active compounds, and pharmaceutical preparations which contain compounds of the formula I.

19 Claims, No Drawings

FOREIGN PATENT DOCUMENTS

| WO | 93/13798 | 7/1993 |
|---|---|---|
| WO | WO 93/15764 | 8/1993 |
| WO | 93/18057 | 9/1993 |
| WO | 94/15958 | 7/1994 |
| WO | WO 94/16094 | 7/1994 |
| WO | WO 94/17828 | 8/1994 |
| WO | 95/14008 | 5/1995 |
| WO | 95/15973 | 6/1995 |
| WO | WO 95/19790 | 7/1995 |
| WO | 96/00581 | 1/1996 |
| WO | 96/06108 | 2/1996 |
| WO | 96/20216 | 7/1996 |
| WO | 96/22966 | 8/1996 |
| WO | 96/33976 | 10/1996 |
| WO | 97/03094 | 1/1997 |
| WO | 98/04247 | 2/1998 |
| WO | 98/04913 | 2/1998 |
| WO | 98/42656 | 10/1998 |

OTHER PUBLICATIONS

Kilger et al., "Molecular analysis of the physiological and pathophysiological role of α4–integrins", *J. Mol. Med.*, vol. 73; pp. 347–354(1995).

McMurray, Robert, W., "Adhesion Molecules in Autoimmune Disease", Seminars in Arthritis and Rheumatism, vol. 25(4); pp. 215–233(1996).

Albelda, S., et al., "Molecular and Cellular Properties of PECAM–1 (endoCAM/CD31): A Novel Vascular Cell–Cell Adhesion Molecule", Journal of Cell Biology, vol. 114, No. 5, pp. 1059–1068.

Issekutz, Thomas B. et al., Rat Blood Neutrophils Express Very Late Antigen 4 and it Mediates Migration to Arthritic Joint and Dermal Inflammation. J. Exp. Med., vol. 183; pp 2175–2184(1996).

Damle, N., et al., "Vascular Cell Adhesion Molecule 1 Induces T–cell Antigen Receptor–Dependent Activation of CD4+T Lymphocytes," Proc. Nat'l. Acad. Sci. USA, vol. 88, pp. 6403–6407 (1991).

Davies, S., et al., "Asymmetric Synthesis of R–β–Amino Butanoic Acid and S–β–Tyrosine: Homochiral Lithium Amide Equivalents for Michael Additions to α,β–Unsaturated Esters," Tetrahedron: Asymmetry, vol. 2, No. 3, pp. 183–186 (1991).

Elices, M.J., et al., "The Integrin VLA–4 Mediates Leukocyte Recruitment to Skin Inflammatory Sites In Vivo," Clinical and Experimental Rheumatology, vol. 11, Supp. 8, pp. S77–S80 (1993).

Elices, M.J., et al., "Expression and Functional Significance of Alternatively Spliced CS1 Fibronectin in Rheumatoid Arthritis Microvasculature," J. Clin. Invest., vol. 93, pp. 405–416 (1994).

Elices, M.J., "The Integrin $\alpha_4\beta_1$ (VLA–4) As a Therapeutic Target," Ciba Foundation Symposium, vol. 189, pp. 79–90 (1995).

Fleisher, D., et al., "Improved Oral Drug Delivery: Solubility Limitations Overcome by the Use of Prodrugs," Advanced Drug Delivery Reviews, vol. 19, pp. 115–130 (1996).

Freedman, A., et al., "Follicular Non–Hodgkin's Lymphoma Cell Adhesion to Normal Germinal Centers and Neoplastic Follicles Involves Very Late Antigen–4 and Vascular Cell Adhesion Molecule–1," Blood, vol. 79, No. 1, pp. 206–212 (1992).

Goldschmidt, V.S., et al., "Über Peptid–Synthesen I," Liebigs. Ann. Chem., vol. 575, pp. 217–231 (1952).

Hafner, L.S., et al., "Preparation of 2–Imino– and 2–Nitrimino–1,3–diazacycloalkanes," J. Am. Chem. Soc., vol. 79, pp. 1157–1159 (1957).

Harlan, J., "Leukocyte–Endothelial Interactions," Blood, vol. 65, No. 3, pp. 513–525 (1985).

Hubbuch, A., "Schutzgruppen in der Peptidsynthese (Part I): Schutzgruppentaktik, Amino– and Carboxyl–Schutzgruppen," Kontakte, vol. 3, No. 79, pp. 14–23 (1979).

Isobe, M., et al, "Effect of Anti–VCAM–1 and Anti–VLA–4 Monoclonal Antibodies on Cardiac Allograft Survival and Response to Soluble Antigens in Mice," Transplantation Proceedings, vol. 26, No. 2, pp. 867–868 (1994).

Issekutz, T., "Inhibition of In Vivo Lymphocyte Migration to Inflammation and Homing to Lymphoid Tissues by the TA–2 Monoclonal Antibody," Journal of Immunology, vol. 147, No. 12, pp. 4178–4184 (1991).

Kim, K., et al., "Monosubstituted Guanidines from Primary Amines and Aminoiminomethanesulfonic Acid," Tetrahedron Letters, vol. 29, No. 26, pp. 3183–3186 (1988).

Kuijpers, T., "Pathophysiological Aspects of VLA–4 Interactions and Possibilities for Therapeutical Interventions," Springer Seminars in Immunopathology, vol. 16, pp. 379–389 (1995).

Laffon, A., et al., "Upregulated Expression and Function of VLA–4 Fibronectin Receptors on Human Activated T–Cells in Rheumatoid Arthritis," J. Clin. Invest., vol. 88, pp. 546–552 (1991).

Morales–Ducret, J., et al., "$\alpha_4/\beta_1$ Integrin (VLA–4) Ligands in Arthritis: Vascular Cell Adhesion Molecule–1 Expression in Synovium and on Fibroblast–Like Synoviocytes," Journal of Immunology, vol. 149, No. 4, pp. 1424–1431 (1992).

Muacevic, G., "New Apparatus and Method for the Toxicological Investigation of Metered Aerosols in Rats," Arch. Toxicol., vol. 34, pp. 1–8 (1975).

Nielson, N., et al., "Glycolamide Esters as Biolabile Prodrugs of Carboxylic Acid Agents: Synthesis, Stability, Bioconversion, and Physiochemical Properties," Journal of Pharmaceutical Sciences, vol. 77, No. 4, pp. 285–298 (1988).

Nowick, J., et al., "Synthesis of Peptide Isocyanates and Isothiocynates," J. Org. Chem, vol. 61, pp. 3929–3934 (1996).

O'Brien, K., et al., "Vascular Cell Adhesion Molecule–1 is Expressed in Human Coronary Atherosclerotic Plaques," J. Clin. Invest., vol. 92, pp. 945–951 (1993).

Ockenhouse, C., et al., "Human Vascular Endothelial Cell Adhesion Receptors for *Plasmodium falciparium*–infected Erythrocytes: Roles for Endothelial Leukocyte Adhesion Molecule 1 and Vascular Cell Adhesion Molecule 1," Journal of Experimental Medicine, vol. 176, pp. 1183–1189 (1992).

Osborn, L., et al., "Direct Expression Cloning of Vascular Cell Adhesion Molecule 1, a Cytokine–Induced Endothelial Protein that Binds to Lymphocytes," Cell, vol. 59, pp. 1203–1211 (1989).

Osborn, L., "Leukocyte Adhesion to Endothelium in Inflammation," Cell, vol. 62, pp. 3–6 (1990).

Postigo, A., et al., Increased Binding of Synovial T. Lymphocytes from Rheumatoid Arthritis to Endothelial–Leukocyte Adhesion Molecule–1 (ELAM–1) and Vascular Cell Adhesion Molecule–1 (VCAM–1), J. Clin. Invest., vol. 89, pp 1445–1452 (1992).

Renkonen, R., et al., "Rapid Communication: Expression of Endothelial Adhesion Molecules In Vivo," Journal of Pathology, vol. 140, No. 4, pp. 763–767 (1992).

Rice, G., et al., "An Inducible Endothelial Cell Surface Glycoprotein Mediates Melanoma Adhesion," Science, vol. 246, pp. 1303–1306 (1989).

Ruoslahti, E., "Fibronectin and its Receptors," Ann. Rev. Biochem., vol. 57, pp. 375–413 (1988).

Safadi, M., et al., "Phosphoryloxymethyl Carbamates and Carbonates—Novel Water–Soluble Prodrugs for Amines and Hindered Alcohols," Pharmaceutical Research, vol. 10, No. 9, pp. 1350–1354 (1993).

Saulnier, M., et al,. "An Efficient Method for the Synthesis of Guanidino Prodrugs," Bioorganic & Medicinal Chemistry Letters, vol. 4, No. 16, pp. 1985–1990 (1994).

Scott, F., et al., "Studies in the Pyrazole Series," Pyrazole Series: Substituted Guanidines, vol. 75, pp. 4053–4054 (1953).

Seiffge, D., et al., "Effects of Different Mediators or Cytokines and Monoclonal Antibodies to Adhesion Molecules on Leukocyte Adhesion in Rat Mesenteric Venules," Int. J. Microcirc., vol. 15, pp. 301–308 (1995).

Springer, T., "Traffic Signals for Lymphocyte Recirculation and Leukocyte Emigration: The Multistep Paradigm," Cell, vol. 76, pp. 301–314 (1994).

Stoolman, L., "Adhesion Molecules Controlling Lymphocyte Migration," Cell, vol. 56, pp. 907–910 (1989).

Takeuchi, T., et al., "Upregulated Expression and Function of Integrin Adhesive Receptors in Systemic Lupus Erythematosus Patients with Vasculitis," J. Clin. Invest., vol. 92, pp. 3008–3016 (1993).

Tropp, C., "Einwirkung von Phosgen auf Polypeptidartige Derivate der p–Amino–benzosäure: Bildung von 1.3–substi–tuierten Hydantoinen," Chem. Ber, vol. 61, pp. 1431–1439 (1928).

Von Hans, T., et al., "Über die Bildung Substituierter Hydantoine aus Aldehyden und Ketonen," Journal für prakishche Chemie N.F., vol. 141, pp. 5–43 (1934).

Wagner, G., et al., "Synthese von 3–[Amidinophenyl]–alaninen und 3–[Amidinophenyl]–milchsären," Pharmaze, vol. 29, No. 1, pp. 12–15 (1974).

Weiss, S., et al., "Zur Guanylierung von Aminen mit O Methyl–isoharnstoff–sulfat," Chemiker–Zeitung, vol. 98, No. 12, pp. 617–618 (1974).

Wollweber, H., et al., "2–(Guanidino)–anilide und Verwandte Verbindungen," Arzneim–Forsch./Drug Res., vol. 34, No. 5, (1984).

Yang, X., et al., "Inhibition of Insulitis and Prevention of Diabetes in Nonobese Diabetic Mice by Blocking L–selectin and Very Late Antigen–4 Adhesion Receptors," Proc. Nat'l. Acad. Sci. USA, vol. 90, pp. 10494–10498 (1993).

Yednock, T., et al., "Prevention of Experimental Autoimmune Encephalomyelitis by Antibodies Against $\alpha_4\beta_1$ Integrin," Nature, vol. 356, pp. 63–66 (1992).

Zettlmeissl, G., et al., "Expression and Characterization of Human CD4: Immunoglobulin Fusion Proteins," DNA and Cell Biology, vol. 9, No. 5, pp. 347–353 (1990).

Anna, C., et al., "The VLA–4/VCAM–1 Pathway is Involved in Lymphocyte Adhesion to Endothelium in Rheumatoid Synovium," Journal of Immunology, vol. 147, No. 12, pp. 4207–4210 (1991).

Barbadillo, C., et al., "Anti–Integrin Immunotherapy in Rheumatoid Arthritis: Protective Effect of Anti–$\alpha$–4 Antibody in Adjuvant Arthritis," Springer Seminars in Immunotherapy, vol. 16 pp. 427–436 (1995).

Bergelson, J., et al., "Do Integrins Use a 'Midas Touch' to Grasp an Asp?" Current Biology, vol. 5, No. 6, pp. 615–617 (1995).

Bergeron, R., et al., "Total Synthesis of ($\pm$)–15–Deoxyspergualin," J. Org. Chem., vol. 52, pp. 1700–1703 (1987).

Borne, R., et al., "Conformational Analogues of Antihypertensive Agents Related to Guanethidine<" Journal of Medicinal Chemistry, vol. 20, No. 6, pp. 771–776 (1977).

Bundgaard, H., "Novel Chemical Approaches in Prodrug Design," Drugs of the Future, vol. 16, No. 5, pp. 443–458 (1991).

Büllesbach, E. "Protection in Peptide Synthesis (Part II): Multifunctional Amino Acids—Cleavage of Protecting Groups—Outlook on the Technique of Protection," Kontakte, vol. 1, No. 80, pp. 23–35 (1980).

* cited by examiner

SUBSTITUTED IMIDAZOLIDINE DERIVATIVES, THEIR PREPARATION, THEIR USE AND PHARMACEUTICAL PREPARATIONS INCLUDING THEM

CROSS-REFERENCE TO RELATED APPLICATIONS

The instant application is a divisional of U.S. Ser. No. 09/516,587, now U.S. Pat. No. 6,331,552, which is a continuation of U.S. Ser. No. 09/195,440, filed on Nov. 18, 1998, now abandoned.

BACKGROUND OF THE INVENTION

1. Field of the Invention

The present invention relates to substituted imidazolidine derivatives of the formula I

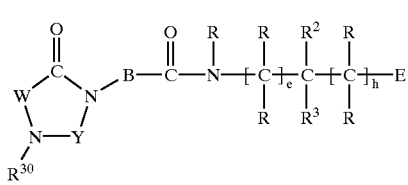

in which B, E, W, Y, R, $R^2$, $R^3$, $R^{30}$, e and h have the meanings indicated below. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leucocytes and/or antagonists of the adhesion receptor VLA-4 belonging to the integrins group. They are generally suitable for the therapy or prophylaxis of illnesses which are caused by an undesired extent of leucocyte adhesion and/or leucocyte migration or are associated therewith, or in which cell-cell or cell-matrix interactions which are based on interactions of VLA-4 receptors with their ligands play a part. The invention furthermore relates to processes for the preparation of the compounds of the formula I, their use, in particular as pharmaceutical active compounds, and pharmaceutical preparations which contain compounds of the formula I.

2. Description of Related Art

The integrins are a group of adhesion receptors which play an important part in cell-cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1. Mac-1 and p 150/95, which are responsible in particular for cell-cell interactions of the immune system, and the subfamilies β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4β1) is atypical, insofar as it is mainly restricted to lymphoid and myeloid cells and is responsible in these for cell-cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leucocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin). which, inter alia, binds neutrophils, ICAM-1 (intercellular adhesion molecule-1), which interacts with LFA-1 (leucocyte function-associated antigen 1) on leucocytes, and VCAM-1 (vascular cell adhesion molecule-1), which binds various leucocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule that is induced on endothelial cells by inflammatory cytokines such as TNF and IL-1 and lipopolysaccharides (LPS). Elices et al. (Cell 1990, 60, 577) showed that VLA-4 and VCAM-1 form a receptor-ligand pair which mediates the adhesion of lymphocytes to activated endothelium. The binding of VCAM-1 to VLA-4 does not take place here due to an interaction of the VLA-4 with an RGD sequence; this sequence is not contained in VCAM-1 (Bergelson et al., Current Biology 1995, 5, 615). VLA-4, however, also occurs on other leucocytes, and the adhesion of leucocytes other than lymphocytes is also mediated via the VCAM-1/VLA-4 adhesion mechanism. VLA-4 thus represents an individual example of a β1 integrin receptor which, via the ligands VCAM-1 and fibronectin, plays an important part both in cell-cell interactions and in cell-extracellular matrix interactions.

The cytokine-induced adhesion molecules play an important part in the recruitment of leucocytes into extravascular tissue regions. Leucocytes are recruited into inflammatory tissue regions by cell adhesion molecules which are expressed on the surface of endothelial cells and serve as ligands for leucocyte cell surface proteins or protein complexes (receptors) (the terms ligand and receptor can also be used vice versa). Leucocytes from the blood must first adhere to endothelial cells before they can migrate into the synovium. Since VCAM-1 binds to cells which carry the integrin VLA-4 (α4β1), such as eosinophils, T and B lymphocytes, monocytes or neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA-4 is also found, for example, on melanoma cell lines, and the VCAM-1/VLA-4 adhesion mechanism is connected with the metastasis of such tumors (Rice et al., Science 1989, 246, 1303).

The main form in which VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. In a further form consisting of six domains, designated here as VCAM-6D, the fourth domain is removed by alternative splicing. VCAM-6D can also bind VLA-4 expressing cells.

Further details on VLA-4. VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; Kuijpers, Springer Semin. Immunopathol. 1995, 16, 379.

On account of the role of the VCAM-1/VLA-4 mechanism in cell adhesion processes, which are of importance, for example, in infections, inflammations or atherosclerosis, it has been attempted to intervene into these adhesion processes to control illnesses, in particular, for example, inflammations (Osborn et al., Cell 1989, 59, 1203). A method of doing this is the use of monoclonal antibodies which are directed against VLA-4. Monoclonal antibodies (mABs)of this type, which as VLA-4 antagonists block the interaction between VCAM-1 and VLA-4, are known. Thus, for example, the anti-VLA-4 mABs HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells CT-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a part in rheumatoid arthritis (van Dinther-Janssen et al., J. Immunol. 1991, 147, 4207).

In vivo experiments have shown that an experimental autoimmune encephalomyelitis can be inhibited by anti-α4 mAB. The migration of leucocytes into an inflammatory focus is likewise blocked by a monoclonal antibody against the α4 chain of VLA-4. The influencing of the VLA-4-dependent adhesion mechanism by antibodies was also investigated in an asthma model in order to investigate the role of VLA-4 in the recruitment of leucocytes into inflamed lung tissue (WO-A-93/13798). The administration of anti-VLA-4 antibodies inhibited the late-phase reaction and airway overreaction in allergic sheep.

The VLA-4-dependent cell adhesion mechanism was also investigated in a primate model of inflammatory bowel disease (IBD). In this model, which corresponds to ulcerative colitis in man, the administration of anti-VLA-4 antibodies resulted in a significant reduction in the acute inflammation.

Moreover, it was possible to show that VLA-4-dependent cell adhesion plays a part in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, S77), multiple sclerosis (Yednock et al., Nature 1992, 356, 63), malaria (Ockenhouse et al., J. Exp. Med. 1992, 176, 1183), arteriosclerosis (O'Brien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991, 114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this case results, as already stated, from the fact that leucocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leucocytes into areas of infection and inflammatory foci has already been discussed above. At the same time, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149, 1424). VLA-4 is upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, has some disadvantages, for example lack of oral availability, easy degradability or immunogenic action on longer-term use, and there is thus a need for VLA-4 antagonists having a favorable profile of properties for use in therapy and prophylaxis.

WO-A-95/14008, WO-A-94/21607 (U.S. Pat. No. 5,658, 935), WO-A-93/18057, EP-A-449 079 (U.S. Pat. No. 5.686, 421), EP-A-530 505 (U.S. Pat. No. 5,389,614), EP-A-566 919 (U.S. Pat. No. 5,397,796), EP-A-580 008 (U.S. Pat. No. 5,424,293)and EP-A-584 694 (U.S. Pat. No. 5,554,594) describe substituted 5-membered ring heterocycles which have an amino, amidino or guanidino function at the N-terminal end of the molecule and which exhibit platelet aggregation-inhibiting actions. EP-A-796 855 describes further heterocycles which are inhibitors of bone resorption. EP-A-842 943, EP-A842 945 and EP-A842 944 (German Patent Applications 19647380.2, 19647381.0 and 19647382.9) describe that compounds from this series and further compounds surprisingly also inhibit leucocyte adhesion and are VLA-4 antagonists. Further investigations showed that the compounds of the present application are also strong inhibitors of leucocyte adhesion and/or are VLA-4 antagonists.

SUMMARY OF THE INVENTION

The present invention relates to compounds of the formula I

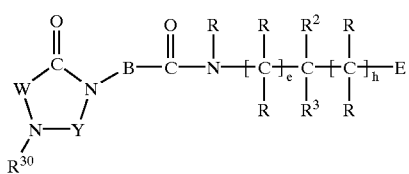

(I)

in which

W is a divalent radical selected from the group consisting of $R^1$—A—$C(R^{13})$, $R^1$—A—$C(R^{13})$=C,

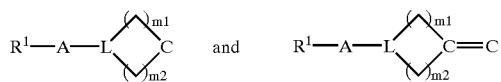

in which the ring systems

can contain one or two identical or different heteroatoms selected from the group consisting of N, O and S, can be saturated or mono- or polyunsaturated and can be substituted by 1, 2 or 3 identical or different substituents $R^{13}$ and/or by one or two doubly bonded oxygen atoms and/or sulfur atoms, and in which L is $C(R^{13})$ or N and in which m1 and m2 independently of one another are one of the numbers 0, 1, 2, 3, 4, 5 and 6, but the sum m1+m2 is one of the numbers 1, 2, 3, 4, 5 or 6;

Y is a carbonyl group, thiocarbonyl group or methylene group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl or a divalent radical of a 5-membered or 6-membered, saturated or unsaturated heterocycle which can contain one or two nitrogen atoms and can be monosubstituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent radical selected from the group consisting of $(C_1-C_6)$-alklene, $(C_2-C_6)$-alkenylene, phenylene, phenylene-$(C_1-C_3)$-alkyl, $(C_1-C_3)$-alkylenephenyl and $(C_1-C_3)$-alkylenephenyl-$(C_1-C_3)$-alkyl, where the $(C_1-C_6)$-alkylene radical and the $(C_2-C_6)$-alkenylene radical are unsubstituted or substituted by one or more identical or different radicals selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl and heteroaryl-$(C_1-C_6)$-alkyl optionally substituted in the heteroaryl radical;

E is tetrazolyl, $(R^8O)_2P(O)$, $R^{10}OS(O)_2$, $R^9NHS(O)_2$, $R^6CO$, $R^7CO$, $R^{10}CO$, HCO, $R^8O$—$CH_2$, $R^8CO$—O—$CH_2$, $R^{8a}O$—CO—O—$CH_2$ or $(R^8O)_2P(O)$—O—$CH_2$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where all radicals R are independent of one another and the radicals R can be identical or different;

$R^1$ is hydrogen, $(C_1-C_{10})$-alkyl which can optionally be mono- or polysubstituted by fluorine, $(C_3-C_{12})$-cycloalkyl, $(C_3-C_{12})$-cycloalkyl-$(C_1-C_8)$-alkyl, $R^{21}$-(($C_6-C_{14}$)-aryl) optionally substituted in the aryl radical, ($R^{21}$—(($C_6-C_{14}$)-aryl))-$(C_1-C_8)$-alkyl optionally substituted in the aryl radical, the radical Het-, Het-$(C_1-C_8)$-alkyl or one of the radicals X—NH—C(=NH)—$R^{20}$—, $X^1$—NH—$R^{20}$—, $R^{21}O$—$R^{20}$—, $R^{21}N(R^{21})$—$R^{20}$—, $R^{21}C(O)$—, $R^{21}O$—C(O)—, $R^{22}N(R^{21})$—C(O)—, $R^{22}C(O)$—N($R^{21}$)—, $R^{21}O$—N=, O= and S=;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, cyano, hydroxyl, $(C_1-C_6)$-alkoxy, $(C_6-C_{14})$-aryl-$(C_1-C_6)$-alkoxy which can also be substituted in the aryl radical, or amino;

X' has one of the meanings of X or is R'—NH—C(=N—R''), in which R' and R'' independently of one another have the meanings of X;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_{10})$-alkyl which can optionally be mono- or polysubstituted by fluorine, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{21}$, $COOR^{15}$, $CON(CH_3)R^{15}$ or $CONHR^{15}$;

$R^4$ is hydrogen or $(C_1-C_{10})$-alkyl which is unsubstituted or is mono- or polysubstituted by identical or different radicals selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-(($C_1$–$C_{10}$)-alkyl)-aminocarbonyl, ($C_6$–$C_{14}$)-aryl-($C_1$–$C_8$)-alkoxycarbonyl which can also be substituted in the aryl radical, ($C_1$–$C_8$)-alkoxycarbonyl, $R^6$—CO, $R^7$—CO, tetrazolyl, trifluormethyl;

$R^5$ is optionally substituted ($C_6$–$C_{14}$)-aryl, ($C_6$–$C_{14}$)-aryl-($C_1$–$C_8$)-alkyl optionally substituted in the aryl radical, or a radical of an optionally substituted monocyclic or bicyclic, 5-membered to 12-membered heterocyclic ring which can be aromatic, partially saturated or completely saturated and which can contain one, two or three identical or different heteroatoms selected from the group consisting of nitrogen, oxygen, and sulfur;

$R^6$ is the radical of a natural or unnatural amino acid, imino acid, optionally N-($C_1$–$C_8$)-alkylated or N-(($C_6$–$C_{14}$)-aryl-($C_1$–$C_8$)-alkylated) azaamino acid which can also be substituted in the aryl radical, or the radical of a dipeptide, tripeptide or tetrapeptide, and their esters and amides, in which free functional groups can be protected by protective groups customary in peptide chemistry and in which the nitrogen atoms in the amide bonds in the group $R^6$—CO can carry a radical R as a substituent;

$R^7$ is the radical of a 5-membered to 10-membered, saturated monocyclic or polycyclic heterocycle bonded via a nitrogen atom, which can contain one, two, three or four identical or different additional ring heteroatoms selected from the group consisting of oxygen, nitrogen and sulfur and which can optionally be substituted on carbon atoms and on additional ring nitrogen atoms, in which additional ring nitrogen atoms can carry identical or different radicals selected from the group consisting of hydrogen, $R^h$, HCO, $R^h$CO, $R^h$O—CO, HO—CO—($C_1$–$C_4$)-alkyl and $R^h$O—CO—($C_1$–$C_4$)-alkyl as substituents and $R^h$ is ($C_1$–$C_8$)-alkyl, ($C_3$–$C_8$)-cycloalkyl, ($C_3$–$C_8$)-cycloalkyl-($C_1$–$C_8$)-alkyl, optionally substituted ($C_6$–$C_{14}$)-aryl or ($C_6$–$C_{14}$)-aryl-($C_1$–$C_8$)-alkyl optionally substituted in the aryl radical;

$R^8$ is hydrogen, ($C_1$–$C_{10}$)-alkyl, optionally substituted ($C_6$–$C_{14}$)-aryl or ($C_6$–$C_{14}$)-aryl-($C_1$–$C_8$)-alkyl which can also be substituted in the aryl radical, where the radicals $R^8$ are independent of one another and can be identical or different;

$R^{8a}$ independently of $R^8$ has one of the meanings of $R^8$ with the exception of hydrogen;

$R^9$ is hydrogen, aminocarbonyl, ($C_1$–$C_{10}$)-alkylaminocarbonyl, ($C_3$–$C_8$)-cycloalkylaminocarbonyl, optionally substituted ($C_6$–$C_{14}$)-arylaminocarbonyl, ($C_1$–$C_{10}$)-alkyl, optionally substituted ($C_6$–$C_{14}$)-aryl or ($C_3$–$C_8$)-cycloalkyl;

$R^{10}$ is hydroxyl, ($C_1$–$C_{10}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, ($C_1$–$C_8$)-alkylcarbonyloxy-($C_1$–$C_6$)-alkoxy, ($C_6$–$C_{14}$)-arylcarbonyloxy-($C_1$–$C_6$)-alkoxy optionally substituted in the aryl radical, ($C_6$–$C_{14}$)-aryl-($C_1$–$C_6$)-alkylcarbonyloxy-($C_1$–$C_6$)-alkoxy optionally substituted in the aryl radical, ($C_1$–$C_6$)-alkoxycarbonyloxy-($C_1$–$C_6$)-alkoxy, ($C_6$–$C_{14}$)-aryloxycarbonyloxy-($C_1$–$C_6$)-alkoxy optionally substituted in the aryl radical, ($C_6$–$C_{14}$)-aryl-($C_1$–$C_6$)-alkoxycarbonyloxy-($C_1$–$C_6$)-alkoxy optionally substituted in the aryl radical, amino, mono- or di-($C_1$–$C_{10}$)-alkyl)-amino or $R^8R^8$N—CO—($C_1$–$C_6$)-alkoxy, in which the radicals $R^8$ are independent of one another and can be identical or different;

$R^{11}$ is hydrogen, $^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is ($C_1$–$C_{10}$)-alkyl, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, or the radical $R^{15}$;

$R^{12b}$ is amino, di-(($C_1$–$C_{10}$)-alkyl)-amino or $R^{12a}$—NH;

$R^{13}$ is hydrogen, ($C_1$–$C_6$)-alkyl which can optionally be mono- or polysubstituted by fluorine, optionally substituted ($C_6$–$C_{14}$)-aryl, ($C_6$–$C_{14}$)-aryl-($C_1$–$C_6$)-alkyl optionally substituted in the aryl radical, ($C_3$–$C_8$)-cycloalkyl or ($C_3$–$C_8$)-cycloalkyl-($C_1$–$C_6$)-alkyl;

$R^{15}$ is $R^{16}$—($C_1$–$C_6$)-alkyl or $R^{16}$;

$R^{16}$ is a 6-membered to 24-membered, bicyclic or tricyclic radical which is saturated or partially unsaturated and which can also contain one, two, three or four identical or different heteroatoms selected from the group consisting of nitrogen, oxygen and sulfur and which can also be substituted by one or more identical or different substituents from the group consisting of ($C_1$–$C_4$)-alkyl and oxo;

$R^{20}$ is a direct bond or a divalent ($C_1$–$C_6$)-alkylene radical;

$R^{21}$ is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, the radical Het- or Het-($C_1$–$C_8$)-alkyl, in which alkyl radicals can be monosubstituted or polysubstituted by fluorine and the radicals $R^{21}$, if they occur more than once, are independent of one another and can be identical or different;

$R^{22}$ is $R^{21}$—, $R^{21}$O—, $R^{21}$N($R^{21}$)—, $R^{21}$C(O)—, $R^{21}$O—C(O)—, $R^{21}$N($R^{21}$)—C(O)—, $R^{21}$N($R^{21}$)—C(=N($R^{21}$))— or $R^{21}$C(O)—N($R^{21}$)—;

$R^{30}$ is one of the radicals $R^{32}$(R)N—CO—N(R)—$R^{31}$, $R^{32}$(R)N—CS—N(R)—$R^{31}$, $R^{32}$(R)N—S(O)$_n$—N(R)—$R^{31}$, $R^{32}$—CO—N(R)—$R^{31}$, $R^{32}$—CS—N(R)—$R^{31}$, $R^{32}$—S(O)$_n$—N(R)—$R^{31}$, $R^{32}$(R)N—CO—$R^{31}$, $R^{32}$(R)N—CS—$R^{31}$, $R^{32}$(R)N—S(O)$_n$—$R^{31}$, $R^{32}$—CO—$R^{31}$, $R^{32}$—CS—$R^{31}$, $R^{32}$—S(O)$_n$—$R^{31}$ or $R^{12a}$—O—CO—N(R)—$R^{31}$, where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_1$–$C_8$)-alkyl, which can optionally be substituted by 1 to 8 fluorine atoms, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical;

$R^{33}$ is a direct bond or a divalent ($C_1$–$C_6$)-alkylene radical;

$R^{34}$ is a divalent radical selected from the group consisting of ($C_1$–$C_8$)-alkylene, ($C_3$–$C_{12}$)-cycloalkylene, ($C_6$–$C_{12}$)-bicycloalkylene, ($C_6$–$C_{12}$)-tricycloalkylene, optionally substituted ($C_6$–$C_{14}$)-arylene and optionally substituted heteroarylene;

$R^{35}$ is a direct bond or a divalent ($C_1$–$C_8$)-alkylene radical;

$R^{36}$ is a direct bond, the group —CO— or the group —S(O)$_n$—;

Het is a radical of a monocyclic or polycyclic, 4-membered to 14-membered, aromatic or nonaromatic ring which contains 1, 2, 3 or 4 identical or different heteroatoms from the group consisting of N, O and S as ring members and can optionally be substituted by one or more identical or different substituents;

e and h independently of one another are 0 or 1;

n is 1 or 2, where the numbers n, if they occur more than once, are independent of one another and can be identical or different;

in any their stereoisomeric forms and mixtures thereof in any ratios, and their physiologically tolerable salts.

Further objects, features, and advantages of the invention, will become apparent from the detailed description that follows.

DETAILED DESCRIPTION OF PREFERRED EMBODIMENTS

In the compounds of the invention, if radicals or substituents can occur more than once in the compounds of the formula I, they can all independently of one another have the meanings indicated and can in all cases be identical or different. In combined radicals, for example arylalkyl, the free bond, via which the radical is bonded, starts from the component indicated at the right end of the name, i.e. in the case of the arylalkyl radical from the alkyl group which carries an awl group as substituent.

Alkyl radicals can be straight-chain or branched. This also applies if they carry substituents or occur as substituents of other radicals, for example in alkoxy radicals, alkoxycarbonyl radicals or arylalkyl radicals. Examples of suitable alkyl radicals include methyl, ethyl, n-propyl, n-butyl, n-pentyl, n-hexyl, n-heptyl, n-octyl, n-nonyl, n-decyl, n-undecyl, n-dodecyl, n-tridecyl, n-pentadecyl, n-hexadecyl, n-heptadecyl, n-octadecyl, isopropyl, isobutyl, isopentyl, isohexyl, 3-methylpentyl, neopentyl, neohexyl, 2,3,5-trimethylhexyl, sec-butyl, tert-butyl, tert-pentyl. Preferred alkyl radicals are methyl, ethyl, n-propyl, isopropyl, n-butyl, isobutyl, sec-butyl, tert-butyl, n-pentyl, isopentyl, n-hexyl and isohexyl. If alkyl radicals are substituted by fluorine atoms, they can contain, for example, 1, 2, 3, 4, 5, 6 or 7 fluorine atoms, if not stated otherwise. For example, in a fluorine-substituted alkyl radical, a methyl group can be present as a trifluoromethyl group.

Alkylene radicals (=alkanediyl radicals), i. e., divalent radicals derived from an alkane, can likewise be straight-chain or branched. They can be bonded via any desired positions. Examples of alkylene radicals include the divalent radicals corresponding to the abovementioned monovalent radicals, for example methylene, ethylene (=1,2-ethylene or 1,1-ethylene), trimethylene (=1,3-propylene), tetramethylene (=1,4-butylene), pentamethylene, hexamethylene or methylene or ethylene substituted by alkyl radicals. Examples of substituted methylene are methylene groups which are substituted by a methyl group, an ethyl group, an n-propyl group, an isopropyl group, an n-butyl group, an isobutyl group, a tert-butyl group, an n-pentyl group, an isopentyl group or an n-hexyl group. Substituted ethylene can be substituted either on one carbon atom or on the other carbon atom or also on both carbon atoms.

Alkenyl radicals and alkenylene radicals (=alkenediyl radicals) as well as alkynyl radicals can also be straight-chain or branched. Examples of alkenyl radicals are vinyl, 1-propenyl, allyl, butenyl, 2-methyl-1-propenyl, 2-methyl-2-propenyl, 3-methyl-2-butenyl, examples of alkenylene radicals are vinylene, propenylene, or butenylene, and examples of alkynyl radicals are ethynyl, 1-propynyl or propargyl.

Cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, which, however, can also be substituted, for example, by ($C_1$–$C_4$)-alkyl. Examples of substituted cycloalkyl radicals are 4-methylcyclohexyl and 2,3-dimethylcyclopentyl. These explanations for the monovalent cycloalkyl radicals correspondingly apply to cycloalkylene radicals (=cycloalkanediyl radicals), i.e. divalent radicals derived from cycloalkanes. Cycloalkylene radicals can be bonded via any desired positions.

Bicycloalkyl radicals, tricycloalkyl radicals and the 6-membered to 24-membered bicyclic and tricyclic radicals representing $R^{16}$ can be formally obtained by abstraction of a hydrogen atom from bicycles or tricycles. The parent bicycles and tricycles can contain only carbon atoms as ring members, they can thus be bicycloalkanes or tricycloalkanes, but in the case of the radicals representing $R^{16}$ they can also contain one to four identical or different heteroatoms selected from the group of nitrogen, oxygen and sulfur, they can thus be aza-, oxa- and thiabicyclo- and -tricycloalkanes. If heteroatoms are contained, preferably one or two heteroatoms, in particular nitrogen atoms or oxygen atoms, are contained. The heteroatoms can occupy any desired positions in the bicyclic or tricyclic structure; they can be located in the bridges or, in the case of nitrogen atoms, also on the bridgeheads. Both the bicycloalkanes and tricycloalkanes and their heteroanalogs can be completely saturated or can contain one or more double bonds; preferably they contain one or two double bonds or are, in particular, completely saturated. Both the bicycloalkanes and tricycloalkanes as well as the heteroanalogs and both the saturated and the unsaturated representatives can be unsubstituted or can be substituted in any desired suitable positions by one or more oxo groups and/or one or more identical or different ($C_1$–$C_4$)-alkyl groups, for example methyl groups or isopropyl groups, preferably methyl groups. The free bond of the bicyclic or tricyclic radical can be located in any desired position of the molecule, the radical can thus be bonded via a bridgehead atom or an atom in a bridge. The free bond can also be located in any desired stereochemical position, for example in an exo position or an endo position.

Examples of parent structures of bicyclic ring systems, from which a bicyclic radical can be derived, are norbornane (=bicyclo[2.2.1]heptane), bicyclo[2.2.2]octane and bicyclo[3.2.1]octane, examples of heteroatom-containing, unsaturated or substituted systems are 7-azabicyclo[2.2.1]heptane, bicyclo[2.2.2]oct-5-ene and camphor (=1,7,7-trimethyl-2-oxobicyclo[2.2.1]heptane).

Examples of systems from which a tricyclic radical can be derived are twistane (=tricyclo[4.4.0.0$^{3,8}$]decane), adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Preferably, bicyclic or tricyclic radicals are derived from bridged bicycles or tricycles. i.e., from systems in which rings have two or more than two atoms in common. Additionally preferred, if not stated otherwise, are also bicyclic or tricyclic radicals having 6 to 18 ring members, particularly preferably those having 6 to 14 ring members, very particularly preferably those having 7 to 12 ring members.

Specifically particularly preferred bicyclic or tricyclic radicals which can represent, for example, a bicycloalkyl group or a tricycloalkyl group, are the 2-norbornyl radical, both that having the free bond in the exo position and that having the free bond in the endo position, the 2-bicyclo [3.2.1]octyl radical, the adamantyl radical, both the 1-adamantyl radical and the 2-adamantyl radical, the homoadamantyl radical and the noradamantyl radical, for example the 3-noradamantyl radical. Additionally preferred are the 1-adamantyl radical and the 2-adamantyl radical.

The above explanations for the monovalent bicycloalkyl radicals and tricycloalkyl radicals correspondingly apply to the divalent bicycloalkylene radicals and tricycloalkylene radicals (=bicycloalkanediyl radicals and tricycloalkanediyl radicals).

($C_6$–$C_{14}$)-Aryl groups include, for example, phenyl, naphthyl for example 1-naphthyl and 2-naphthyl, biphenylyl, for example 2-biphenylyl, 3-biphenylyl and 4-biphenylyl, anthryl or fluorenyl, ($C_6$–$C_{10}$)-aryl groups are, for example, 1-naphthyl, 2-naphthyl and phenyl. Biphenylyl radicals, naphthyl radicals and in particular phenyl radicals are preferred aryl radicals. Aryl radicals, in particular phenyl radicals, can be unsubstituted or monosubstituted or polysubstituted, for example monosubstituted, disubstituted, trisubstituted or tetrasubstituted, by identical or different radicals. Substituted aryl radicals, in particular phenyl radicals, are preferably substituted by radicals selected from ($C_1$–$C_8$)-alkyl, in particular ($C_1$–$C_4$)-alkyl such as methyl; ($C_1$–$C_8$)-alkoxy, in particular ($C_1$–$C_4$)-alkoxy such as methoxy; ($C_1$–$C_8$)-alkoxy, in particular ($C_1$–$C_4$)-alkoxy, which is substituted by one or more fluorine atoms, for example 1, 2, 3, 4 or 5 fluorine atoms, such as trifluoromethoxy; halogen; nitro; amino; trifluoromethyl; hydroxyl; hydroxy-($C_1$–$C_4$)-alkyl such as, for example, hydroxymethyl or 1-hydroxyethyl or 2-hydroxyethyl; methylenedioxy; ethylenedioxy, formyl; acetyl; cyano; hydroxycarbonyl; aminocarbonyl; ($C_1$–$C_4$)-alkoxycarbonyl; phenyl; phenoxy; benzyl; benzyloxy, tetrazolyl. The same applies, for example to substituted aryl radicals, in groups such as arylalkyl, arylcarbonyl, etc. Arylalkyl radicals are, for example, 1- and 2-naphthylmethyl, 2-, 3- and 4-biphenylylmethyl and 9-fluorenylmethyl and in particular benzyl, all of which can also be substituted. Substituted arylalkyl radicals are, for example, benzyl radicals and naphthylmethyl radicals substituted in the aryl moiety by one or more ($C_1$–$C_8$)-alkyl radicals, in particular ($C_1$–$C_4$)-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, 1-, 3-, 4-, 5-, 6-, 7- and 8-methyl-2-naphthylmethyl; benzyl radicals and naphthylmethyl radicals substituted in the aryl moiety by one or more ($C_1$–$C_8$)-alkoxy radicals, in particular ($C_1$–$C_4$)-alkoxy radicals, for example 4-methoxybenzyl, 4-neopentyloxybenzyl, 3,5-dimethoxybenzyl, 2,3,4-trimethoxybenzyl, 3,4-methylenedioxybenzyl; trifluoromethoxybenzyl radicals; nitrobenzyl radicals, for example 2-, 3- and 4-nitrobenzyl; halobenzyl radicals, for example 2-, 3- and 4-chlorobenzyl and 2-, 3-, and 4-fluorobenzyl, 3,4-dichlorobenzyl, pentafluoro-benzyl; trifluoromethylbenzyl radicals, for example 3- and 4-trifluoromethylbenzyl or 3,5-bistrifluoromethylbenzyl. Substituted arylalkyl radicals, however, can also contain substituents different from one another. In the compounds of the formula I, however, in general not more than two nitro groups can be present in the molecule.

In monosubstituted phenyl radicals, the substituent can be located in the 2-position, the 3-position or the 4-position. Disubstituted phenyl can be substituted in the 2,3-position, the 2,4-position, the 2,5-position, the 2,6-position, the 3,4-position or the 3,5-position. In trisubstituted phenyl radicals, the substituents can be situated, for example, in the 2,3,4-position, the 2,3,5-position, the 2,4,5-position, the 2,4,6-position, the 2,3,6-position, or the 3,4,5-position.

The above explanations for the monovalent aryl radicals apply correspondingly to the divalent arylene radicals, i.e., divalent radicals derived from aromatics. Arylene radicals can be linked via any desired positions. An example of arylene radicals is phenylene radicals, which can be present, for example, as 1,4-phenylene or as 1,3-phenylene.

Phenylene-alkyl is in particular phenylenemethyl (—$C_6H_4$—$CH_2$—) or phenyleneethyl (for example (—$C_6H_4$—$CH_2$—$CH_2$—), alkylene-phenyl is in particular methylenephenyl (—$CH_2$—$C_6$—$H_4$—). Phenylene-alkenyl is in particular phenyleneethenyl or phenylenepropenyl.

Heteroaryl is a radical of a monocyclic or polycyclic aromatic system having 5 to 14 ring members, which contains 1, 2, 3, 4 or 5 heteroatoms as ring members. Examples of heteroatoms are N, O and S. If several heteroatoms are contained, these can be identical or different. Heteroaryl radicals can also be unsubstituted or monosubstituted or polysubstituted, for example monosubstituted, disubstituted or trisubstituted, by identical or different radicals selected from the ($C_1$–$C_8$)-alkyl, in particular ($C_1$–$C_4$)-alkyl, ($C_1$–$C_8$)-alkoxy, in particular ($C_1$–$C_4$)-alkoxy, ($C_1$–$C_8$)-alkoxy, in particular ($C_1$–$C_4$)-alkoxy, which is substituted by one or more, for example 1, 2, 3, 4 or 5, fluorine atoms, halogen, nitro, amino, trifluoromethyl, hydroxyl, hydroxy-($C_1$–$C_4$)-alkyl such as, for example, hydroxymethyl or 1-hydroxyethyl or 2-hydroxyethyl, methylenedioxy, ethylenedioxy, formyl, acetyl, cyano, hydroxycarbonyl, aminocarbonyl, ($C_1$–$C_4$)-alkoxycarbonyl, phenyl, phenoxy, benzyl, benzyloxy, tetrazolyl. Preferably heteroaryl is a monocyclic or bicyclic aromatic radical which contains 1, 2, 3 or 4, in particular 1, 2 or 3, identical or different heteroatoms selected from N, O and S and which can be substituted by 1, 2, 3 or 4, in particular 1 to 3, identical or different substituents selected from ($C_1$–$C_6$)-alkyl, ($C_1$–$C_6$)-alkoxy, fluorine, chlorine, nitro, amino, trifluoromethyl, hydroxyl, hydroxy-($C_1$–$C_6$)-alkyl, ($C_1$–$C_6$)-alkoxycarbonyl, phenyl, phenoxy, benzyloxy and benzyl. Particularly preferably, heteroaryl is a monocyclic or bicyclic aromatic radical having 5 to 10 ring members, in particular a 5-membered to 6-membered monocyclic aromatic radical which contains 1, 2 or 3, in particular 1 or 2, identical or different heteroatoms selected from N, O and S and can be substituted by 1 or 2 identical or different substituents selected from the group of ($C_1$–$C_4$)-alkyl, ($C_1$–$C_4$)-alkoxy, phenyl, phenoxy, benzyloxy and benzyl.

Heterocycles which represent monocyclic or bicyclic, 5-membered to 12-membered heterocyclic rings can be aromatic or partially or completely saturated. They can be unsubstituted or substituted on one or more carbon atoms or on one or more nitrogen atoms by identical or different substituents, such as is indicated for the radical heteroaryl.

In particular, the heterocyclic ring can be monosubstituted or polysubstituted, for example, monosubstituted, disubstituted, trisubstituted, or pentasubstituted, on carbon atoms by identical or different radicals selected from $(C_1–C_8)$-alkyl, for example $(C_1–C_4)$-alkyl, $(C_1–C_8)$-alkoxy, for example $(C_1–C_4)$-alkoxy such as methoxy, phenyl-$(C_1–C_4)$-alkoxy, for example benzyloxy, hydroxyl, oxo, halogen, nitro, amino or trifluoromethyl, and/or ring nitrogen atoms in heterocyclic rings and in heteroaryl radicals can be substituted by $(C_1–C_8)$-alkyl, for example $(C_1–C_4)$-alkyl such as methyl or ethyl, by optionally substituted phenyl or phenyl-$(C_1–C_4)$-alkyl, for example benzyl.

The radical Het comprises aromatic heterocycles and thus also the groups representing heteroaryl, insofar as these come under the definition of Het with respect to the number of ring members and heteroatoms. However, Het additionally also comprises nonaromatic heterocycles which are completely saturated or which contain one or more double bonds in the ring system. Het can be substituted on nitrogen atoms and/or carbon atoms by one or more, for example 1, 2, 3 or 4, identical or different substituents, for example by $(C_1–C_8)$-alkyl, in particular $(C_1–C_4)$-alkyl, $(C_3–C_{12})$-cycloalkyl, $(C_3–C_{12})$-cycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, heteroaryl, heteroaryl-$(C_1–C_8)$-alkyl, $(C_1–C_8)$-alkoxy, in particular $(C_1–C_4)$-alkoxy, optionally substituted phenoxy, benzyloxy, halogen, nitro, amino, $(C_1–C_8)$-alkylamino, di-$(C_1–C_8)$-alkyl)-amino, trifluoromethyl, hydroxyl, methylenedioxy, ethylenedioxy, cyano, hydroxycarbonyl, aminocarbonyl, $(C_1–C_4)$-alkoxycarbonyl and generally by ester groups, acyl groups, oxo, thioxo, where alkyl radicals can be monosubstituted or polysubstituted by fluorine.

Examples of parent structures of heterocycles from which a heteroaryl radical, the radical Het, the radical of a monocyclic or bicyclic 5-membered to 12-membered heterocyclic ring, the divalent radical of a 5-membered or 6-membered heterocyclic, the heterocyclic radical representing $R^7$ or a heterocyclic radical representing $R^{16}$ can be derived, insofar as in the individual case they come under the respective definition, include pyrrole, furan, thiophene, imidazole, pyrazole, oxazole, isoxazole, thiazole, isothiazole, tetrazole, pyridine, pyrazine, pyrimidine, indole, isoindole, indazole, phthalazine, quinoline, isoquinoline, quinoxaline, quinazoline, cinnoline, β-carboline and benzo-fused, cyclopenta-fused, cyclohexa-fused or cyclohepta-fused derivatives of these heterocycles.

Nitrogen heterocycles can also be present as N-oxides or as quaternary salts.

Radicals which can be heteroaryl or the radical of a monocyclic or bicyclic 5-membered to 12-membered heterocyclic ring include, for example, 2- or 3-pyrrolyl, phenylpyrrolyl, for example 4- or 5-phenyl-2-pyrrolyl, 2- or 3-furyl, 2- or 3-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or 2-benzothiazolyl or, as radicals of partially saturated or completely saturated heterocyclic rings, for example also dihydropyridinyl, pyrrolidinyl, for example 2- or 3-(N-methylpyrrolidinyl), piperazinyl, morpholinyl, thiomorpholinyl, tetrahydrothienyl, benzodioxolanyl.

The explanations for heteroaryl radicals correspondingly apply to the divalent heteroarylene radicals, i.e., the divalent radicals derived from heteroaromatics.

Heterocyclic radicals representing the radical $R^7$ can be unsubstituted or monosubstituted or polysubstituted, for example disubstituted, trisubstituted, tetrasubstituted or pentasubstituted, by identical or different substituents on the carbon atoms and/or on additional ring nitrogen atoms. Carbon atoms can be substituted, for example, by $(C_1–C_8)$-alkyl, in particular $(C_1–C_4)$-alkyl, $(C_1–C_8)$-alkoxy, in particular $(C_1–C_4)$-alkoxy, halogen, nitro, amino, trifluoromethyl, hydroxyl, oxo, cyano, hydroxycarbonyl, aminocarbonyl, $(C_1–C_4)$-alkoxycarbonyl, phenyl, phenoxy, benzyl, benzyloxy, tetrazolyl, in particular by $(C_1–C_4)$-alkyl, for example methyl, ethyl or tert-butyl, $(C_1–C_4)$-alkoxy, for example methoxy, hydroxyl, oxo, phenyl, phenoxy, benzyl, benzyloxy. Sulfur atoms can be oxidized to the sulfoxide or to the sulfone. Examples of the radical Het include 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxo-4-thiomorpholinyl, perhydroazepin-1-yl, 2,6-dimethyl-1-piperidinyl, 3,3-dimethyl-4-morpholinyl, 4-isopropyl-2,2,6,6-tetramethyl-1-piperazinyl, 4-acetyl-1-piperazinyl, and 4-ethoxycarbonyl-1-piperazinyl.

Halogen is fluorine, chlorine, bromine or iodine, in particular fluorine or chlorine.

The substituent on a substituted alkylene radical or alkenylene radical representing B can on the one hand contain a cycle when it is a substituent selected from the group of $(C_3–C_{10})$-cycloalkyl, $(C_3–C_{10})$-cycloalkyl-$(C_1–C_6)$-alkyl, optionally substituted $(C_6–C_{14})$-aryl, $(C_6–C_{14})$-aryl-$(C_1–C_6)$-alkyl optionally substituted in the aryl radical, optionally substituted heteroaryl and heteroaryl-$(C_1–C_6)$ optionally substituted in the heteroayl radical. On the other hand the substituent on a substituted alkylene radical or alkenylene radical representing B can be acyclic if it is a substituent selected from the group of $(C_1–C_8)$-alkyl, $(C_2–C_8)$-alkenyl and $(C_2–C_8)$-alkynyl. The acyclic substituents can contain 2, 3, 4, 5, 6, 7 or 8 carbon atoms and, in the case of a saturated alkyl radical, also 1 carbon atom. In the case of the alkenyl radicals and alkynyl radicals, the double bond or triple bond can be located in any desired position and in the case of the double bond can have the cis configuration or trans configuration. As explained above, these alkyl radicals, alkenyl radicals, and alkynyl radicals can be straight-chain or branched.

Examples of substituents which may be mentioned in particular which the $(C_1–C_6)$-alkylene radical or $(C_2–C_6)$-alkenylene radical representing B can carry are methyl, ethyl, n-propyl, n-butyl, n-pentyl, n-hexyl, n-heptyl, n-octyl, isopropyl, isobutyl, isopentyl, isohexyl, sec-butyl, tert-butyl, tert-pentyl, neopentyl, neohexyl, 3-methylpentyl, 2-ethylbutyl, vinyl, allyl, 1-propenyl, 2-butenyl, 3-butenyl, 3-methyl-2-butenyl, ethynyl, 1-propynyl, 2-propynyl, 6-hexynyl, phenyl, benzyl, 1-phenylethyl, 2-phenylethyl, 3-phenylpropyl, 4-biphenylylmethyl, cyclopropyl, cyclopropylmethyl, cyclobutyl, cyclobutylmethyl, cyclopentyl, cyclopentylmethyl, cyclohexyl, cyclohexylmethyl, 2-cyclohexylethyl, 3-cyclooctylpropyl, 2-pyridyl, 3-pyridyl, 4-pyridyl, 2-pyridylmethyl, 3-pyridylmethyl, 4-pyridylmethyl, 2-(4-pyridyl)ethyl, 2-furylmethyl, 3-furylmethyl, 2-thienylmethyl, 3-thienylmethyl or 2-(3-indolyl)ethyl.

The radical of an amino acid, imino acid or azaamino acid or of a dipeptide, tripeptide or tetrapeptide representing $R^6$ is obtained from the corresponding amino acid, imino acid or azaamino acid or the dipeptide, tripeptide or tetrapeptide as customary in peptide chemistry by formally removing a hydrogen atom from the N-terminal amino group or from the imino group. This group is then linked in peptide fashion through an amide bond to the CO group in the group $R^6$—CO via the free bond on the amino group or the imino group resulting in this way.

The natural and unnatural amino acids can be present in all stereochemical forms, for example in the D form, the L form or in the form of a mixture of stereoisomers, for example in the form of a racemate. Preferred amino acids are α-amino acids and β-amino acids, α-amino acids are particularly preferred. Suitable amino acids which may be mentioned, for example, are (cf. Houben-Weyl, Methoden der organischen Chemie [Methods of Organic Chemistry], Volume 15/1 and 15/2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)₂, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)aminoacetic acid.

If $R^6$ is the radical of a natural or unnatural α-amino acid then this radical can correspond, for example, to the formula —N(R)—CH(SC)—CO—AG in which CO—AG is the acid group of the amino acid or a derivative thereof, for example an ester group, an amide group or a group containing a peptide radical, and SC is the side chain of the α-amino acid, i.e., for example, one of the substituents which are contained in the α-position of the abovelisted α-amino acids. Examples of side chains are alkyl radicals, for example the methyl group in alanine or the isopropyl group in valine, the benzyl radical in phenylalanine, the phenyl radical in phenylglycine, the 4-aminobutyl radical in lysine or the hydroxycarbonyl methyl group in aspartic acid. Apart from by their chemical structure, such side chains and thus the amino acids can also be arranged in groups on the basis of their physicochemical properties, for example lipophilic side chains can be differentiated from hydrophilic side chains which contain polar groups. Examples of lipophilic side chains which can be contained in amino acids representing $R^6$ are alkyl radicals, arylalkyl radicals or aryl radicals. The same applies to amino acids which are part of a radical of a dipeptide, tripeptide or tetrapeptide representing $R^6$.

Azaamino acids are natural or unnatural amino acids in which a CH unit is replaced by a nitrogen atom. For example, in α-amino acids the central structural unit

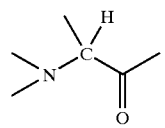

is replaced by

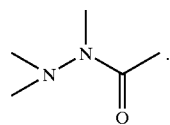

Suitable radicals of imino acids are, in particular, radicals of heterocycles selected from the following group: pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1⁶,⁹]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, hydroxypyrrolidine-2-carboxylic acid, all of which can optionally be substituted (see following formulae):

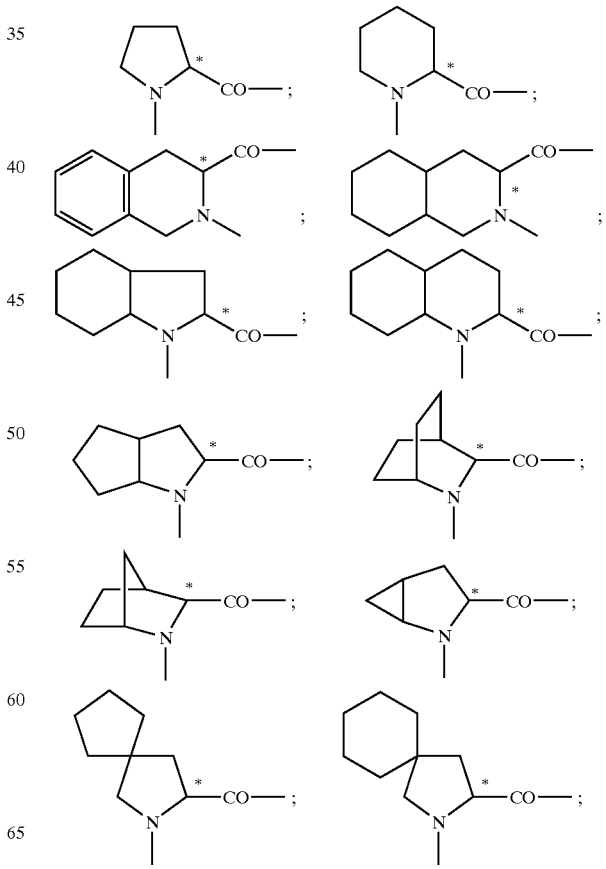

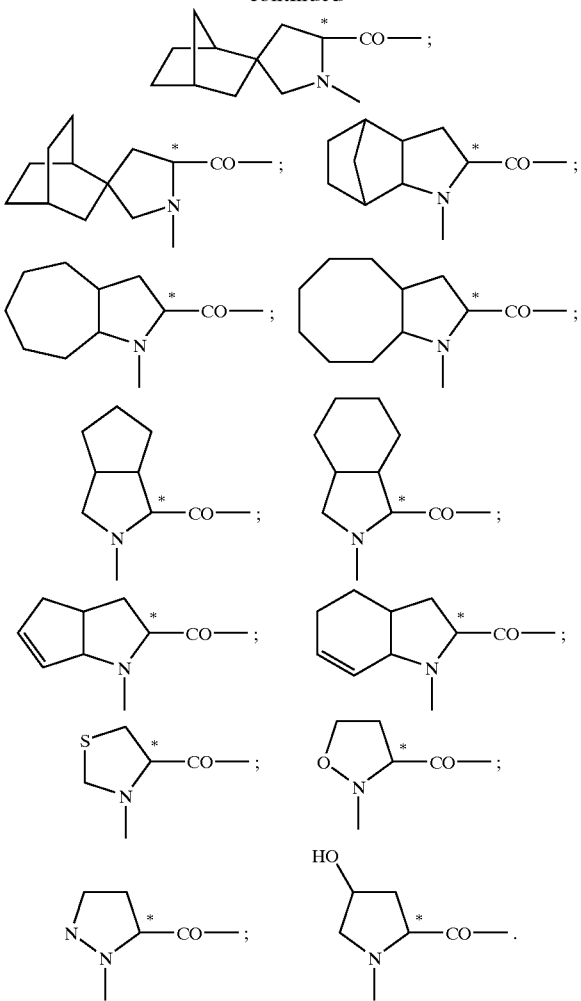

The heterocycles on which the above radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EPA 89,637; EP-A 90,341; EP-A 90,362; EPA 105,102; EP-A 109,020; EP-A 111,873; EP-A 271,865 and EP-A 344,682. All of these documents are incorporated by reference in their entirety, Dipeptides, tripeptides and tetrapeptides can contain natural or unnatural amino acids, imino acids and azaamino acids as structural units. In addition, the natural or unnatural amino acids, imino acids, azaamino acids, dipeptides, tripeptides and tetrapeptides can also be present in the form of derivatives of the carboxylic acid group, for example as esters or amides, such as, for example, as the methyl ester, ethyl ester, n-propyl ester, isopropyl ester, isobutyl ester, tertbutyl ester, benzyl ester, unsubstituted amide, methylamide, ethylamide, semicarbazide or ω-amino-($C_2$-$C_8$)-alkylamide.

Functional groups in radicals of amino acids, imino acids, azaamino acids, dipeptides, tripeptides and tetrapeptides as well as in other parts of the compounds of the formula I can be present in protected form. Suitable protective groups such as, for example, urethane protective groups, carboxyl protective groups and side chain protective groups are described in Hubbuch, Kontakte (Merck) 1979, No. 3, pages 14 to 23, and in Büllesbach, Kontakte (Merck) 1980, No. 1, pages 23 to 35, both incorporated herein by reference in their entirety. The following may be mentioned in particular. Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Physiologically tolerable salts of the compounds of the formula I are, in particular, pharmaceutically utilizable or nontoxic salts. Of compounds of the formula I which contain acidic groups, for example carboxylic acid groups, such salts are, for example, alkali metal salts or alkaline earth metal salts, such as, for example, sodium salts, potassium salts, magnesium salts and calcium salts, or ammonium salts, such as, for example, salts with physiologically tolerable quaternary ammonium ions and acid addition salts with ammonia and physiologically tolerable organic amines, such as, for example triethylamine, ethanolamine, tris(2-hydroxyethyl) amine, α,α,α-tris(hydroxymethyl)methylamine or with amino acids, in particular basic amino acids.

Compounds of the formula I which contain basic groups, for example an amino group, amidino group or guanidino group, form salts with inorganic acids, such as, for example, hydrochloric acid, sulfuric acid or phosphoric acid, and with organic carboxylic acids or sulfonic acids, such as, for example, acetic acid, citric acid, benzoic acid, maleic acid, fumaric acid, tartaric acid, methanesulfonic acid or p-toluenesulfonic acid. Compounds which contain both acidic groups and basic groups can also be present in the form of internal salts or betaines, which are also included by the present invention.

Salts can be obtained from the compounds of the formula I according to customary procedures known to the person skilled in the art, for example by combining with an organic or inorganic acid or base in a solvent or dispersant, or alternatively from other salts by anion exchange or cation exchange.

The compounds of the formula I can be present in stereoisomeric forms. If the compounds of the formula I contain one or more centers of asymmetry, these can independently of one another have the S configuration or the R configuration. The invention includes all possible stereoisomers of the compounds of the formula I, for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention likewise relates to diastereomers in diastereomerically pure form and in the form of mixtures in all ratios. In the presence of cis/trans isomerism, the invention relates to both the cis form and the trans form and mixtures of these forms in all ratios. Individual stereoisomers can be prepared, if desired, by use of stereochemically homogeneous starting substances in the synthesis, by stereoselective synthesis or by separation of a mixture according to customary methods, for example by chromatography or crystallization, in the case of enantiomers, for example, by chromatography on chiral phases. If appropriate, derivatization can be carried out before separation of stereoisomers. A stereoisomer mixture can be separated at the stage of the compounds of the formula I or at the stage of a starting substance or of an intermediate in the course of the synthesis.

The compounds of the formula I according to the invention can moreover contain mobile hydrogen atoms, i.e. be present in various tautomeric forms. The present invention also relates to all tautomers of the compounds of the formula I. The present invention furthermore includes derivatives of compounds of the formula I, for example, solvates such as hydrates and adducts with alcohols, esters, prodrugs and other physiologically tolerable derivatives of compounds of the formula I, as well as active metabolites of compounds of the formula I. The invention relates in particular to prodrugs of the compounds of the formula I which are converted into compounds of the formula I under physiological conditions. Suitable prodrugs of the compounds of the formula I. i.e. chemically modified derivatives of the compounds of the formula I having improved properties as desired, are known to the person skilled in the art. More detailed information on prodrugs is found, for example, in Fleisher et al., Advanced Drug Delivery Reviews 19 (1996) 115–130, Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350, each incorporated herein by reference in their entirety. Suitable prodrugs of the compounds of the formula I are especially ester prodrugs of carboxylic acid groups, amid prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom situated on a nitrogen atom is replaced by an acyl group or carbamate group. Suitable acyl groups and carbamate groups for the acyl prodrugs and carbamate prodrugs are, for example, the groups $R^p$—CO and $R^{p^a}$O—CO, in which $R^p$ is hydrogen, $(C_1-C_{18})$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, heteroaryl or heteroaryl-$(C_1-C_8)$-alkyl and $R^{p^a}$ has the meanings indicated for $R^p$ with the exception of hydrogen.

The individual structural elements in the formula I preferably, for example, have the following meanings which they can have independently of one another. Radicals occurring more than once can have the meanings independently of one another and can in all cases be identical or different.

W is preferably a divalent radical selected from the group of $R^1$—A—$C(R^{13})$ and

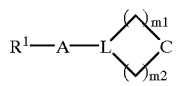

in which the ring systems

can contain one or two identical or different heteroatoms selected from the group of N and O, can be saturated or monounsaturated and can be substituted by 1 or 2 identical or different substituents $R^{13}$ and/or by one or two doubly bonded oxygen atoms, and in which L is $C(R^{13})$ or N and in which m1 and m2 independently of one another are one of the numbers 0, 1, 2, 3 and 4, but the sum m1+m2 is one of the numbers 1, 2, 3 or 4, in particular one of the numbers 1, 3 or 4. W is particularly preferably the divalent radical $R^1$—A—C $(R^{13})$, in which $R^{13}$ has the meanings indicated above. W is very particularly preferably the divalent radical $R^1$—A—$C(R^{13})$, in which $R^{13}$ has the meanings indicated above, but is other than hydrogen. Specific groups of this type are, for example, the divalent radicals di($(C_1-C_4)$-alkyl)methylene (($(C_1-C_4)$-alkyl) $_2$C<, dimethylmethylene $(CH_3)_2$C< and (methyl) (phenyl)methylene $(CH_3)(C_6H_5)$C<. If W is the radical

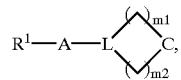

a number of groups of this type is formed by the carbocyclic groups of the formula $(CH_2)_{m3}$C<, which are optionally substituted as indicated, in which the number m3 of the polymethylene chain bonded to the spiro carbon atom C< via the terminal groups is 2, 3, 4, 5 or 6. Specific groups W of this type are, for example, the divalent radicals 1,1-cyclopropylidene (=dimethylenemethylene), 1,1-cyclopentylidene (=tetramethylenemethylene) and 1,1-cyclohexylidene (=pentamethylenemethylene), i.e. the radicals

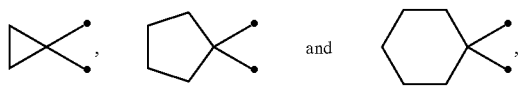

in which the free bonds are symbolized by the line having a dot at the end, where the radicals derived from the 5-membered ring and from the 6-membered ring can in each case carry a doubly bonded oxygen atom as a substituent. On the whole, compounds of the formula I in which W has a meaning other than $CH_2$ form a group of preferred compounds.

Y is preferably a carbonyl group or thiocarbonyl group, particularly preferably a carbonyl group.

A is preferably a direct bond, one of the divalent radicals $(C_1-C_6)$-alkylene, in particular $(C_1-C_4)$-alkylene, $(C_5-C_6)$-cycloalkylene, phenylene, phenylene-$(C_1-C_4)$-alkyl, in particular phenylene-$(C_1-C_2)$-alkyl, or a divalent radical of a 5-membered or 6-membered saturated or unsaturated heterocycle which can contain one or two nitrogen atoms and can be monosubstituted or disubstituted by $(C_1-C_6)$-alkyl or doubly bonded oxygen or sulfur. Particularly preferably, A is a direct bond or one of the divalent radicals $(C_1-C_4)$-alkylene, phenylene and phenylene-$(C_1-C_2)$-alkyl. If W is the radical $R^1$—A—$C(R^{13})$, a number of preferred radicals $R^1$—A— is formed from the radicals $(C_1-C_4)$-alkyl, optionally substituted phenyl and phenyl-$(C_1-C_2)$-alkyl optionally substituted in the phenyl radical, in particular from the radicals $(C_1-C_4)$-alkyl and optionally substituted phenyl.

B is preferably a divalent methylene radical or ethylene radical (=1,2-ethylene), where the methylene radical and the ethylene radical are unsubstituted or substituted by one or more identical or different radicals selected from the group of $(C_1-C_8)$-alkyl, in particular $(C_1-C_6)$-alkyl, $(C_2-C_8)$-alkenyl, $(C_2-C_8)$-alkynyl, $(C_3-C_{10})$-cycloalkyl, in particular $(C_3-C_6)$-cycloalkyl, $(C_3-C_{10})$-cycloalkyl-$(C_1-C_6)$-alkyl, in particular $(C_3-C_6)$-cycloalkyl-$(C_1-C_6)$-alkyl, optionally substituted $(C_6-C_{14})$-aryl, in particular optionally substituted $(C_6-C_{10})$-aryl, $(C_6-C_{14})$-aryl-$(C_1-C_6)$-alkyl optionally substituted in the aryl radical, in particular $(C_6-C_{10})$-aryl-$(C_1-C_6)$-alkyl optionally substituted in the aryl radical, optionally substituted heteroaryl, heteroaryl- ($C_1$–$C_6$)-alkyl optionally substituted in the heteroaryl radical. Particularly preferably, B is a substituted methylene radical or ethylene radical of this type, in particular a substituted methylene radical of this type. If an alkylene radical or alkenylene radical representing B is monosubstituted or polysubstituted, it is preferably monosubstituted, disubstituted or trisubstituted, particularly preferably monosubstituted or disubstituted, in particular monosubstituted. If a methylene radical or ethylene radical representing B is substituted, it is preferably substituted by one or two identical or different radicals, in particular by one radical selected from the group of ($C_1$–$C_8$)-alkyl, in particular ($C_1$–$C_6$)-alkyl, i.e., straight-chain or branched alkyl having 1, 2, 3, 4, 5, 6, 7 or 8 carbon atoms, and ($C_3$–$C_6$)-cycloalkyl-($C_1$–$C_2$)-alkyl.

E is preferably tetrazolyl, $R^6CO$, $R^7CO$, $R^{10}CO$, HCO, $R^8O$—$CH_2$, $R^8CO$—O—$CH_2$ or $(R^8O)_2P(O)$—O—$CH_2$, particularly preferably tetrazolyl, $R^{10}CO$, $R^8O$—$CH_2$, $R^8CO$—O—$CH_2$ or $(R^8O)_2P(O)$—O—$CH_2$, very particularly preferably $R^{10}CO$, $R^8O$—$CH_2$ or $R^8CO$—O—$CH_2$. A radical $R^8O$—$CH_2$ representing the group E is preferably the hydroxymethyl radical HO—$CH_2$. Especially preferably, E is $R^{10}CO$, HO—$CH_2$ or $R^8CO$—O—$CH_2$.

The radicals R preferably independently of one another are hydrogen or ($C_1$–$C_8$)-alkyl, in particular hydrogen, methyl or ethyl. They can be identical or different.

$R^2$ is preferably hydrogen or ($C_1$–$C_8$)-alkyl, in particular ($C_1$–$C_6$)-alkyl, particularly preferably hydrogen, methyl or ethyl.

$R^3$ is preferably hydrogen, ($C_1$–$C_8$)-alkyl which can optionally be substituted by 1 to 8 fluorine atoms, optionally substituted ($C_6$–$C_{12}$)-aryl, ($C_6$–$C_{12}$)-aryl-($C_1$–$C_6$)-alkyl optionally substituted in the aryl radical, optionally substituted heteroaryl, heteroaryl-($C_1$–$C_6$)-alkyl optionally substituted in the heteroaryl radical, ($C_3$–$C_8$)-cycloalkyl, ($C_3$–$C_8$)-cycloalkyl-($C_1$–$C_6$)-alkyl, ($C_6$–$C_{12}$)-bicycloalkyl, ($C_6$–$C_{12}$)-bicycloalkyl-($C_1$–$C_6$)-alkyl, ($C_6$–$C_{12}$)-tricycloalkyl, ($C_6$–$C_{12}$)-tricycloalkyl-($C_1$–$C_6$)-alkyl, ($C_2$–$C_8$)-alkenyl, ($C_2$–$C_8$)-alkynyl, $R^{11}NH$, $COOR^{21}$, $CON(CH_3)R^4$, $CONHR^4$, $CON(CH_3)R^{15}$ or $CONHR^{15}$. Particularly preferably, $R^3$ is hydrogen, ($C_1$–$C_8$)-alkyl which can optionally be substituted by 1 to 6 fluorine atoms, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, ($C_3$–$C_8$)-cycloalklyl, ($C_3$–$C_8$)-cycloalkyl-($C_1$–$C_4$)-alkyl, ($C_6$–$C_{12}$)-bicycloalkyl, ($C_6$–$C_{12}$)-bicycloalkyl-($C_1$–$C_4$)-alkyl, ($C_6$–$C_{12}$)-tricycloalkyl, ($C_6$–$C_{12}$)-tricycloalkyl-($C_1$–$C_4$)-alkyl, $R^{11}NH$, $COOR^{21}$, $CON(CH_3)R^4$, $CONHR^4$, $CON(CH_3)R^{15}$ or $CONHR^{15}$. Very particularly preferably, $R^3$ is hydrogen, ($C_1$–$C_6$)-alkyl which can optionally be substituted by 1 to 6 fluorine atoms, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, ($C_3$–$C_8$)-cycloalkyl, ($C_3$–$C_8$)-cycloalkyl-($C_1$–$C_4$)-alkyl, $R^{11}NH$, $COOR^{21}$, $CON(CH_3)R^4$, $CONHR^4$, $CON(CH_3)R^{15}$ or $CONHR^{15}$. Especially preferably, $R^3$ is, for example, ($C_1$–$C_8$)-alkyl, in particular ($C_1$–$C_4$)-alkyl, for example methyl which can optionally be substituted by 1 to 6 fluorine atoms, ($C_6$–$C_{10}$)-aryl, in particular phenyl which can be unsubstituted or substituted, or $CONHR^4$.

$R^4$ is preferably ($C_1$–$C_8$)-alkyl which is unsubstituted or is substituted as indicated above in the definition of $R^4$. Particularly preferably, $R^4$ is ($C_1$–$C_8$)-alkyl, in particular ($C_1$–$C_6$)-alkyl which is unsubstituted or is substituted by one or two identical or different substituents selected from the group of hydroxyl, ($C_1$–$C_8$)-alkoxy, $R^5$, optionally substituted ($C_3$–$C_8$)-cycloalkyl, hydroxycarbonyl, aminocarbonyl, ($C_6$–$C_{10}$)-aryl-($C_1$–$C_4$)-alkoxycarbonyl which can also be substituted in the aryl radical, ($C_1$–$C_6$)-alkoxycarbonyl, $R^6$—CO, $R^7$—CO tetrazolyl, trifluoromethyl. It is very particularly preferred if one of the substituents in the alkyl group representing $R^4$ is bonded in the 1-position of the alkyl group, i.e., to that carbon atom of the alkyl group to which there is also bonded the nitrogen atom in the group $CONHR^4$ or in the group $CON(CH_3)R^4$, and if this substituent in the 1-position is of one of the radicals hydroxycarbonyl, aminocarbonyl, ($C_6$–$C_{10}$)-aryl-($C_1$–$C_4$)-alkoxycarbonyl which can also be substituted in the aryl radical, $R^6$—CO, $R^7$—CO, ($C_1$–$C_6$)-alkoxycarbonyl or tetrazolyl. In this very particularly preferred case, the radical —$NHR^4$ or the radical —$N(CH_3)R^4$ is then the radical of an α-amino acid or of an N-methyl-α-amino acid or of a derivative thereof, where the radical of the amino acid is formally obtained by abstraction of a hydrogen atom from the amino group of the amino acid (if the substituent in the 1-position is the group $R^6$—CO, the radical —$NHR^4$ or the radical —$N(CH_3)R^4$ is correspondingly the radical of a dipeptide, tripeptide, tetrapeptide or pentapeptide). Especially preferred α-amino acids are in this case those having a lipophilic side chain, for example phenylglycine, phenylalanine, valine, leucine, isoleucine and homologs thereof, as well as derivatives of these amino acids such as esters, amides or the derivatives in which the carboxylic acid group is converted into the radical $R^6$—CO or $R^7$—CO.

$R^5$ is preferably optionally substituted (($C_6$–$C_{12}$)-aryl, in particular optionally substituted ($C_6$–$C_{10}$)-aryl, especially optionally substituted phenyl.

$R^8$ is preferably hydrogen, ($C_1$–$C_8$)-alkyl, optionally substituted ($C_6$–$C_{12}$)-aryl or ($C_6$–$C_{12}$)-aryl-($C_1$–$C_8$)-alkyl which can also be substituted in the aryl radical, particularly preferably hydrogen, ($C_1$–$C_6$)-alkyl, optionally substituted ($C_6$–$C_{10}$)-aryl or ($C_6$–$C_{10}$)-aryl-($C_1$–$C_6$)-alkyl which can also be substituted in the aryl radical, very particularly preferably hydrogen, ($C_1$–$C_6$)-alkyl or phenyl-($C_1$–$C_4$)-alkyl optionally substituted in the phenyl radical. $R^{8a}$ preferably has one of the preferred meanings of $R^8$ with the exception of hydrogen.

$R^{10}$ is preferably hydroxyl, ($C_1$–$C_8$)-alkoxy, ($C_6$–$C_{12}$)-aryl-($C_1$–$C_8$)-alkoxy which can also be substituted in the aryl radical, optionally substituted ($C_6$–$C_{12}$)-aryloxy, ($C_1$–$C_8$)-alkylcarbonyloxy-($C_1$–$C_6$)-alkoxy, ($C_6$–$C_{12}$)-aryl-($C_1$–$C_6$)-alkylcarbonyoxy-($C_1$–$C_6$)-alkoxy optionally substituted in the aryl radical, ($C_1$–$C_8$)-alkoxycarbonyloxy-($C_1$–$C_6$)-alkoxy, ($C_6$–$C_{12}$)-aryl-($C_1$–$C_6$)-alkoxycarbonyloxy-($C_1$–$C_6$)-alkoxy optionally substituted in the aryl radical, amino, mono- or di-(($C_1$–$C_8$)-alkyl)-amino, aminocarbonyl-($C_1$–$C_6$)-alkoxy, (mono- or di-(($C_1$–$C_8$)-alkyl)-amino)-carbonyl-($C_1$–$C_6$)-alkoxy, (mono- or di-(($C_6$–$C_{12}$)-aryl-($C_1$–$C_6$)-alkyl))-amino)-carbonyl-($C_1$–$C_6$)-alkoxy or (N-(($C_1$–$C_8$)-alkyl)-N-(($C_6$–$C_{12}$)-aryl-($C_1$–$C_6$)-alkyl)-amino)-carbonyl-($C_1$–$C_6$)-alkoxy all optionally substituted in the aryl radical. Particularly preferably, $R^{10}$ is hydroxyl, $(C_1-C_8)$-alkoxy, $(C_6-C_{10})$-aryl-$(C_1-C_6)$-alkoxy which can also be substituted in the aryl radical, optionally substituted $(C_6-C_{10})$-aryloxy, $(C_1-C_6)$-alkylcarbonyloxy-$(C_1-C_6)$-alkoxy, $(C_1-C_6)$-alkoxycarbonyloxy-$(C_1-C_6)$-alkoxy, amino, mono- or di-$((C_1-C_6)$-alkyl)-amino, aminocarbonyl-$(C_1-C_6)$-alkoxy or (mono- or di-$((C_1-C_6)$-alkyl)-aminocarbonyl-$(C_1-C_6)$-alkoxy.

$R^{11}$ is preferably hydrogen, $R^{12a}$, $R^{12a}$—CO, $R^{12a}$—O—CO, $R^{12b}$—CO, $R^{12b}$—CS or $R^{12a}$—S(O)$_2$, particularly preferably hydrogen, $R^{12a}$, $R^{12a}$—CO, $R^{12a}$—O—CO, $R^{12b}$—CO, or $R^{12a}$—S(O)$_2$, very particularly preferably $R^{12a}$, $R^{12a}$—CO, $R^{12a}$—O—CO, or $R^{12a}$—S(O)$_2$.

$R^{12a}$ is preferably $(C_1-C_{10})$-alkyl, $(C_2-C_8)$-alkenyl, $(C_2-C_8)$-alkynyl, $(C_5-C_{10})$-cycloalkyl, $(C_5-C_{10})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$.

$R^{13}$ is preferably hydrogen or $(C_1-C_6)$-alkyl, where a preferred alkyl radical represented by $R^{13}$ is the methyl radical. Particularly preferably, $R^{13}$ is $(C_1-C_6)$-alkyl, very particularly preferably $(C_1-C_4)$-alkyl, in particular methyl.

$R^{15}$ is preferably $R^{16}$—$(C_1-C_3)$-alkyl or $R^{16}$, in particular $R^{16}$—$C_1$alkyl or $R^{16}$.

$R^{20}$ is preferably a direct bond or a divalent $(C_1-C_4)$-alkylene radical, particularly preferably a direct bond or a divalent $(C_1-C_2)$-alkylene radical, in particular a direct bond or a methylene radical or ethylene radical (1,2-ethylene), very particularly preferably a direct bond or a methylene radical.

$R^{21}$ is preferably hydrogen, $(C_1-C_8)$-alkyl, $(C_3-C_{12})$-cycloalkyl, $(C_3-C_{12})$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, the radical Het- or Het-$(C_1-C_6)$-alkyl, where alkyl radicals can be monosubstituted or polysubstituted by fluorine and the radicals $R^{21}$, if they occur more than once, are independent of one another and can be identical or different. $R^{21}$ is particularly preferably hydrogen, $(C_1-C_6)$-alkyl, $(C_3-C_6)$-cycloalkyl, $(C_3-C_6)$-cycloalkyl-$(C_1-C_4)$-alkyl, optionally substituted $(C_6-C_{10})$-aryl or $(C_6-C_{10})$-aryl-$(C_1-C_4)$-alkyl, optionally substituted in the aryl radical, where alkyl radicals can be monosubstituted or polysubstituted by fluorine. $R^{21}$ is very particularly preferably hydrogen, $(C_1-C_6)$-alkyl, $(C_3-C_6)$-cycloalkyl, $(C_3-C_6)$-cycloalkyl-$(C_1-C_2)$-alkyl, optionally substituted $(C_6-C_{10})$-aryl or $(C_6-C_{10})$-aryl-$(C_1-C_2)$-alkyl optionally substituted in the aryl radical, where alkyl radicals can be monosubstituted or polysubstituted by fluorine, where again, if the radicals $R^{21}$ occur more than once, they are independent of one another and can be identical or different.

$R^{30}$ is preferably one of the radicals $R^{32}(R)N$—CO—N(R)—$R^{31}$, $R^{32}(R)N$—CS—N(R)—$R^{31}$, $R^{32}(R)N$—S(O)$_n$—N(R)—$R^{31}$, $R^{32}$—CO—N(R)—$R^{31}$, $R^{32}$—S(O)$_n$—N(R)—$R^{31}$, $R^{32}(R)N$—CO—$R^{31}$, $R^{32}(R)N$—S(O)$_n$—$R^{31}$, $R^{32}$—CO—$R^{31}$, $R^{32}$—S(O)$_{n}$—$R^{31}$ or $R^{12a}$—O—CO—N(R)—$R^{31}$, in which n is 1 or 2. Particularly preferably, $R^{30}$ is one of the radicals $R^{32}(R)N$—CO—N(R)—$R^{31}$, $R^{32}(R)N$—CS—N(R)—$R^{31}$, $R^{32}$—CO—N(R)—$R^{31}$ or $R^{32}(R)N$—CO—$R^{31}$. Very particularly preferably, $R^{30}$ is $R^{32}(R)N$—CO—N(R)—$R^{31}$ or $R^{32}(R)N$—CS—N(R)—$R^{31}$, especially preferably $R^{32}(R)N$—CO—N(R)—$R^{31}$, in particular $R^{32}NH$—CO—NH—$R^{31}$.

$R^{32}$ is preferably hydrogen, $(C_1-C_8)$-alkyl which can optionally be substituted by 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical. Particularly preferably, $R^{32}$ is hydrogen, $(C_1-C_6)$-alkyl which can optionally be substituted by 1 to 6 fluorine atoms, $(C_2-C_6)$-alkenyl, $(C_2-C_6)$-alkynyl, $(C_5-C_6)$-cycloalkyl, $(C_5-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl or heteroaryl-$(C_1-C_6)$-alkyl optionally substituted in the heteroaryl radical. Very particularly preferably, $R^{32}$ is hydrogen, $(C_1-C_6)$-alkyl which can optionally be substituted by 1 to 6 fluorine atoms, $(C_2-C_6)$-alkenyl, $(C_2-C_6)$-alkynyl, $(C_5-C_6)$-cycloalkyl, $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl or heteroaryl-$(C_1-C_4)$-alkyl optionally substituted in the heteroaryl radical. A specifically preferred radical representing $R^{32}$ is optionally substituted $(C_6-C_{10})$-aryl, in particular unsubstituted phenyl or phenyl which is substituted by one or more identical or different substituents of the substituents on aromatics indicated above. If the radical $R^{32}$ is bonded to a sulfur atom, it preferably has a meaning other than hydrogen.

$R^{33}$ is preferably a direct bond or a divalent $(C_1-C_4)$-alkylene radical, particularly preferably a direct bond or a divalent $(C_1-C_2)$-alkylene radical, very particularly preferably a direct bond.

$R^{34}$ is preferably a divalent radical selected from the group of $(C_1-C_8)$-alkylene, $(C_5-C_{10})$-cycloalkylene, $(C_6-C_{12})$-bicycloalkylene, optionally substituted $(C_6-C_{14})$-arylene and optionally substituted heteroarylene, particularly preferably a divalent radical selected from the group of $(C_1-C_6)$-alkylene, $(C_5-C_6)$-cycloalkylene, optionally substituted $(C_6-C_{12})$-arylene and optionally substituted heteroarylene, very particularly preferably a divalent radical from the group consisting of $(C_1-C_6)$-alkylene, optionally substituted $(C_6-C_{10})$-arylene and optionally substituted heteroarylene, moreover preferably a divalent radical selected from the group of $(C_1-C_4)$-alkylene and optionally substituted $(C_6-C_{10})$-arylene.

$R^{35}$ is preferably a direct bond or a divalent $(C_1-C_4)$-alkylene radical, particularly preferably a direct bond or a divalent $(C_1-C_2)$-alkylene radical, in particular a direct bond or methylene or ethylene (1,2-ethylene), very particularly preferably $(C_1-C_2)$-alkylene (methylene or ethylene).

$R^{36}$ is preferably a direct bond.

$R^{31}$ is preferably a divalent radical —$R^{33}$—$R^{34}$—$R^{35}$—$R^{36}$—, in which one or more of the radicals $R^{33}$, $R^{34}$, $R^{35}$ and $R^{36}$ have preferred meanings. Particularly preferably, $R^{31}$ is a divalent radical selected from the group of $(C_1-C_8)$-alkylene, $(C_5-C_6)$-cycloalkylene, $(C_5-C_6)$-cycloalkylene-$(C_1-C_6)$-alkyl, optionally substituted $(C_6-C_{10})$-arylene, $(C_6-C_{10})$-arylene-$(C_1-C_6)$-alkyl optionally substituted in the arylene radical, optionally substituted heteroarylene, heteroarylene-$(C_1-C_6)$-alkyl optionally substituted in the heteroarylene radical, $(C_1-C_8)$-alkylene-CO, optionally substituted $(C_6-C_{10})$-arylene-CO, $(C_6-C_{10})$-arylene-$(C_1-C_6)$-alkyl-CO optionally substituted in the arylene radical, optionally substituted heteroarylene-CO, heteroarylene-$(C_1-C_6)$-alkyl-CO optionally substituted in the heteroarylene radical, optionally substituted $(C_6-C_{10})$-arylene-S(O)$_n$, $(C_6-C_{10})$-arylene-$(C_1-C_6)$-alkyl-S(O)$_n$ optionally substituted in the arylene radical, optionally substituted heteroarylene-S(O)$_n$ and heteroarylene-$(C_1-C_6)$-alkyl-S(O)$_n$ optionally substituted in the heteroarylene radical, in which n is 1 or 2, and where the CO group and the S(O)$_n$ group are bonded to the nitrogen atom in the imidazolidine ring in the formula I and, in the case of the radicals cycloalkylenealkyl, arylenealkyl and heteroarylenealkyl, the allyl group is bonded to the nitrogen atom in the imidazolidine ring in the formula I. Very particularly preferably, $R^{31}$ is a divalent radical selected from the group of $(C_1-C_6)$-alkylene, optionally substituted $(C_6-C_{10})$-arylene and $(C_6-C_{10})$-arylene-$(C_1-C_4)$-alkyl optionally substituted in the aryl radical, where in the case of the arylenealkyl radical, the alkyl group is bonded to the nitrogen atom in the imidazolidine ring in the formula I. Moreover, $R^{31}$ is preferably a divalent radical selected from the group of $(C_1-C_6)$-alkylene and $(C_6-C_{10})$-arylene-$(C_1-C_4)$-alkyl optionally substituted in the aryl radical, in particular $(C_6-C_{10})$-arylene-$(C_1-C_2)$-alkyl, where in the case of the arylenealkyl radical, the alkyl group is bonded to the nitrogen atom in the imidazolidine ring in the formula I. Especially preferably, $R^{31}$ is the divalent radical phenylenemethyl-$C_6H_4$—$CH_2$—, in particular the radical -1,4-phenylenemethyl-, in which the methyl group is bonded to the nitrogen atom in the imidazolidine ring in the formula I.

If $R^3$ is hydrogen or one of the radicals $(C_1-C_{10})$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-cycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, COOR$^{21}$, CON(CH$_3$)R$^4$, CONHR$^4$, COOR$^{15}$, CON(CH$_3$)R$^{15}$ or CONHR$^{15}$, e is preferably 0 and h is preferably 1. If $R^3$ is $R^{11}$NH, e is preferably 1 and h is preferably 0. Compounds of the formula I in which e is 0 and h is 1 form a preferred group of compounds. In these preferred compounds, the group —NR—[C(R)(R)]$_h$—C(R$^2$)(R$^3$)—[C(R)(R)]$_h$—E in the formula I is particularly preferably the group —NH—CH(R$^3$)—CH$_2$—E.

Preferred compounds of the formula I are those compounds in which one or more of the radicals have preferred meanings or one specific of the preferred meanings mentioned, all combinations of preferred meanings of radicals being a subject of the present invention.

A particularly preferred group of compounds are compounds of the formula I in which W is a divalent radical selected from the group of $R^1$—A—C(R$^{13}$), $R^1$—A—C(R$^{13}$)=C,

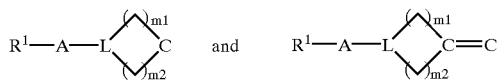

where the ring systems

can contain one or two identical or different heteroatoms selected from the group of N, O and S, can be saturated or monounsaturated or polyunsaturated and can be substituted by 1, 2 or 3 identical or different substituents $R^{13}$ and/or by one or two doubly bonded oxygen atoms and/or sulfur atoms, and where L is C(R$^{13}$) or N and where m1 and m2 independently of one another are one of the numbers 0, 1, 2, 3, 4, 5 and 6, the sum m1+m2, however, is one of the numbers 1, 2, 3, 4, 5 or 6;

Y is a carbonyl group, thiocarbonyl group or methylene group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl or a divalent radical of a 5-membered or 6-membered, saturated or unsaturated heterocycle which can contain one or two nitrogen atoms and can be monosubstituted or disubstituted by $(C_1-C_6)$-alkyl or doubly bonded oxygen or sulfur, where in the radicals phenylenealkyl and phenylenealkenyl, the radical $R^1$ is bonded to the phenylene group;

B is a divalent radical selected from the group of $(C_1-C_6)$-alkylene, $(C_2-C_6)$-alkenylene, phenylene, phenylene-$(C_1-C_3)$-alkyl, $(C_1-C_3)$-alkylenephenyl and $(C_1-C_3)$-alkylenephenyl-$(C_1-C_3)$-alkyl, where the $(C_1-C_6)$-alkylene radical and the $(C_2-C_6)$-alkenylene radical are unsubstituted or are substituted by one or more identical or different radicals selected from the group of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is tetrazolyl, (R$^8$O)$_2$P(O), R$^{10}$OS(O)$_2$, R$^9$NHS(O)$_2$, R$^6$CO, R$^7$CO or R$^{10}$CO;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl, where all radicals R are independent of one another and the radicals R can be identical or different;

$R^1$ is hydrogen, $(C_1-C_{10})$-alkyl, which can optionally be monosubstituted or polysubstituted by fluorine, $(C_3-C_{12})$-cycloalkyl, $(C_3-C_{12})$-cycloalkyl-$(C_1-C_8)$-alkyl, $R^{21}$—(($C_6-C_{14}$)-aryl) optionally substituted in the aryl radical, $(R^{21}$—(($C_6-C_{14}$)-aryl))—$(C_1-C_8)$-alkyl optionally substituted in the aryl radical, the radical Het-, Het-$(C_1-C_8)$-alkyl or one of the radicals X—NH—C(=NH)—R$^{20}$—, X$^1$—NH—R$^{20}$—, $R^{21}O-R^{20}-$, $R^{21}N(R^{21})-R^{20}-$, $R^{21}C(O)-$, $R^{21}O-C(O)-$, $R^{22}N(R^{21})-C(O)-$, $R^{22}C(O)-N(R^{21})-$, $R^{21}O-N=$, $O=$ and $S=$;

X is hydrogen, $(C_1-C_6)$-alkyl, $(C_1-C_6)$-alkylcarbonyl, $(C_1-C_6)$-alkoxycarbonyl, $(C_1-C_{10})$-alkycarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, cyano, hydroxyl, $(C_1-C_6)$-alkoxy, $(C_6-C_{14})$-aryl-$(C_1-C_6)$-alkoxy which can also be substituted in the aryl radical, or amino;

$X^1$ has one of the meanings of X or is R'—NH—C(=N—R"), where R' and R" independently of one another have the meanings of X;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{21}$, $COOR^{15}$, $CON(CH_3)R^{15}$ or $CONHR^{15}$;

$R^4$ is hydrogen or $(C_1-C_{10})$-alkyl which is unsubstituted or monosubstituted or polysubstituted by identical or different radicals selected from the group of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{10})$-alkyl)-aminocarbonyl, $(C_6-C_{14})$-aryl-$(C_1-C_8)$-alkoxycarbonyl, which can also be substituted in the aryl radical, $(C_1-C_8)$-alkoxycarbonyl, $R^6$—CO, $R^7$—CO, tetrazolyl and trifluoromethyl;

$R^5$ is optionally substituted $(C_6-C_{14})$-aryl, $(C_6-C_{14})$-aryl-$(C_1-C_8)$-alkyl optionally substituted in the aryl radical or a radical of an optionally substituted monocyclic or bicyclic, 5-membered to 12-membered heterocyclic ring, which can be aromatic, partially saturated or completely saturated and which can contain one, two or three identical or different heteroatoms selected from the group of nitrogen, oxygen and sulfur;

$R^6$ is the radical of a natural or unnatural amino acid, imino acid, optionally N—$(C_1-C_8)$-alkylated or N-$((C_6-C_{14})$-aryl-$(C_1-C_8)$-alkylated) azaamino acid, which can also be substituted in the aryl radical, or the radical of a dipeptide, tripeptide or tetrapeptide as well as their esters and amides, where free functional groups can be protected by protective groups customary in peptide chemistry and where the nitrogen atoms in the amide bonds in the group $R^6$—CO can carry a radical R as a substituent;

$R^7$ is the radical of a 5-membered to 10-membered, saturated monocyclic or polycyclic heterocycle bonded via a nitrogen atom, which can contain one, two, three or four identical or different additional ring heteroatoms selected from the group of oxygen, nitrogen and sulfur and which can optionally be substituted on carbon atoms and on additional ring nitrogen atoms, where additional ring nitrogen atoms can carry identical or different radicals selected from the group of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^8$ is hydrogen, $(C_1-C_{10})$-cycloalkyl, optionally substituted $(C_6-C_{14})$-aryl or $(C_6-C_{14})$-aryl-$(C_1-C_8)$-alkyl which can also be substituted in the aryl radical, where the radicals $R^8$ are independent of one another:

$R^9$ is hydrogen, aminocarbonyl, $(C_1-C_{10})$-alkylaminocarbonyl, $(C_3-C_8)$-cycloalkylaminocarbonyl, optionally substituted $(C_6-C_{14})$-arylaminocarbonyl, $(C_1-C_{10})$-alkyl, optionally substituted $(C_6-C_{14})$-aryl or $(C_3-C_6)$-cycloalkyl;

$R^{10}$ is hydroxyl, $(C_1-C_{10})$-cycloalkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy optionally substituted in the aryl radical, amino or mono- or di-$((C_1-C_{10})$-alkyl)-amino;

$R^{11}$ is hydrogen, $R^{12a}$, $R^{12a}$—CO, H—CO, $R^{12a}$—O—CO, $R^{12b}$—CO, $R^{12b-CS}$, $R^{12a}$—$S(O)_2$ or $R^{12b}$—$S(O)_2$;

$R^{12a}$ is $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-$((C_1-C_{10})$-alkyl)-amino or $R^{12a}$—NH:

$R^{13}$ is hydrogen, $(C_1-C_6)$-alkyl which can optionally be monosubstituted or polysubstituted by fluorine, optionally substituted $(C_6-C_{14})$-aryl, $(C_6-C_{14})$-aryl-$(C_1-C_6)$-alkyl optionally substituted in the aryl radical, $(C_3-C_8)$-cycloalkyl or $(C_3-C_8)$-cyclo-$(C_1-C_6)$-alkyl;

$R^{15}$ is $R^{16}$—$(C_1-C_6)$-alkyl or $R^{16}$;

$R^{16}$ is a 6-membered to 24-membered bicyclic or tricyclic radical which is saturated or partially unsaturated and which can also contain one, two, three or four identical or different heteroatoms selected from the group of nitrogen, oxygen and sulfur and which can also be substituted by one or more identical or different substituents from the group consisting of $(C_1-C_4)$-alkyl and oxo;

$R^{20}$ is a direct bond or a divalent $(C_1-C_6)$-alkylene radical;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl, optionally substituted in the aryl radical, the radical Het- or Het-$(C_1-C_8)$-alkyl, where alkyl radicals can be monosubstituted or polysubstituted by fluorine and the radicals $R^{21}$, if they occur more than once, are independent of one another and can be identical or different;

$R^{22}$ is $R^{21}$—, $R^{21}O$—, $R^{21}N(R^{21})$—, $R^{21}C(O)$—, $R^{21}O$—C(O)—, $R^{21}N(R^{21})$—C(O)—, $R^{21}N(R^{21})$—C(=N(R^{21}))— or $R^{21}C(O)$—N(R^{21})—;

$R^{30}$ is one of the radicals $R^{32}(R)N$—CO—N(R)—$R^{31}$, $R^{32}(R)N$—CS—N(R)—$R^{31}$, $R^{32}(R)N$—$S(O)_n$—N(R)—$R^{31}$, $R^{32}$—CO—N(R)—$R^{31}$, $R^{32}$—CS—N(R)—$R^{31}$, $R^{32}$—$S(O)_n$—N(R)—$R^{31}$, $R^{32}(R)N$—CO—$R^{31}$, $R^{32}(R)N$—CS—$R^{31}$, $R^{32}(R)N$—$S(O)_n$—$R^{31}$, $R^{32}$—CO—$R^{31}$, $R^{32}$—CS—$R^{31}$ or $R^{32}$—$S(O)_n$—$R^{31}$, where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_1$–$C_8$)-alkyl which can optionally be substituted by 1 to 8 fluorine atoms, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical;

$R^{33}$ is a direct bond or a divalent ($C_1$–$C_6$)-alkylene radical;

$R^{34}$ is a divalent radical selected from the group of ($C_1$–$C_8$)-alkylene, ($C_3$–$C_{12}$)-cycloalkylene, ($C_6$–$C_{12}$)-bicycloalkylene, ($C_6$–$C_{12}$)-tricycloalkylene, optionally substituted ($C_6$–$C_{14}$)-arylene and optionally substituted heteroarylene;

$R^{35}$ is a direct bond or a divalent ($C_1$–$C_8$)-alkylene radical;

$R^{36}$ is a direct bond, the group —CO— or the group —S(O)$_n$—;

Het is a radical of a monocyclic or polycyclic 4-membered to 14-membered, aromatic or nonaromatic ring which contains 1, 2, 3 or 4 identical or different heteroatoms from the group consisting of N, O and S as ring members and which can optionally be substituted by one or more identical or different substituents;

e and h independently of one another are 0 or 1;

n is 1 or 2, where the numbers n, if they occur more than once, are independent of one another and can be identical or different;

in all their stereoisomeric forms and mixtures thereof in all ratios, and their physiologically tolerable salts.

A further particularly preferred group of compounds is formed by compounds of the formula I in which W is a divalent radical selected from the group of $R^1$—A—C($R^{13}$), $R^1$—A—C($R^{13}$)=C,

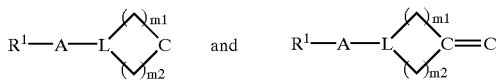

in which the ring systems

can contain one or two identical or different heteroatoms selected from the group of N and O, can be saturated or monounsaturated and can be substituted by 1 or 2 identical or different substituents $R^{13}$ and/or by one or two doubly bonded oxygen atoms, and in which L is C($R^{13}$) or N and in which m1 and m2 independently of one another are one of the numbers 0, 1, 2, 3, 4 and 5, the sum m1+m2, however, is one of the numbers 1, 2, 3, 4 and 5;

Y is a carbonyl group or thiocarbonyl group;

A is a direct bond, one of the divalent radicals ($C_1$–$C_6$)-alkylene, ($C_3$–$C_7$)-cycloalkylene, phenylene, phenylene-($C_1$–$C_6$)-alkyl, phenylene-($C_2$–$C_6$)-alkenyl or a divalent radical of a 5-membered or 6-membered, saturated or unsaturated heterocycle which can contain one or two nitrogen atoms and can be monosubstituted or disubstituted by ($C_1$–$C_6$)-alkyl or doubly bonded oxygen or sulfur, where in the radicals phenylenealkyl and phenylenealkenyl the radical $R^1$ is bonded to the phenylene group;

B is a divalent methylene radical or ethylene radical, where the methylene radical and the ethylene radical are unsubstituted or are substituted by one or more identical or different radicals selected from the group of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

E is tetrazolyl, $R^{10}$CO, $R^8$O—$CH_2$, $R^8$CO—O—$CH_2$ or ($R^8$O)$_2$P(O)—O—($CH_2$;

R is hydrogen, ($C_1$–$C_8$)-alkyl, ($C_3$–$C_{10}$)-cycloalkyl, ($C_3$–$C_{10}$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl or heteroaryl-($C_1$–$C_6$)-alkyl optionally substituted in the heteroaryl radical, where all radicals R are independent of one another and the radicals R can be identical or different;

$R^1$ is hydrogen, ($C_1$–$C_{10}$)-alkyl, which can optionally be monosubstituted or polysubstituted by fluorine, ($C_3$–$C_{10}$)-cycloalkyl, ($C_3$–$C_{10}$)-cycloalkyl-($C_1$–$C_6$)-alkyl, $R^{21}$—(($C_6$–$C_{14}$)-aryl) optionally substituted in the aryl radical, ($R^{21}$—(($C_6$–$C_{14}$)-aryl))—($C_1$–$C_8$)-alkyl optionally substituted in the aryl radical, the radical Het-, Het-($C_1$–$C_8$)-alkyl or one of the radicals X—NH—C(=NH)—$R^{20}$—, $X^1$—NH—$R^{20}$—, $R^{21}$O—$R^{20}$—, $R^{22}$C(O)—N($R^{21}$)—, $R^{22}$N($R^{21}$)—C(O)—, $R^{21}$O—N=, O= and S=;

X is hydrogen, ($C_1$–$C_6$)-alkyl, ($C_1$–$C_6$)-alkylcarbonyl, ($C_1$–$C_6$)-alkoxycarbonyl, ($C_1$–$C_{10}$)-alkylcarbonyloxy-($C_1$–$C_6$)-alkoxycarbonyl, optionally substituted ($C_6$–$C_{14}$)-arylcarbonyl, optionally substituted ($C_6$–$C_{14}$)-aryloxycarbonyl, ($C_6$–$C_{14}$)-aryl-($C_1$–$C_6$)-alkoxycarbonyl which can also be substituted in the aryl radical, hydroxyl, ($C_1$–$C_6$)-alkoxy, ($C_6$–$C_{14}$)-aryl-($C_1$–$C_6$)-alkoxy which can also be substituted in the aryl radical, or amino;

$X^1$ has one of the meanings of X or is R'—NH—C(=N—R"), in which R' and R" independently of one another have the meanings of X;

$R^2$ is hydrogen, ($C_1$–$C_8$)-alkyl, optionally substituted ($C_6$–$C_{10}$)-aryl or ($C_6$–$C_{10}$)-aryl-($C_1$–$C_8$)-alkyl optionally substituted in the aryl radical;

$R^3$ is hydrogen, ($C_1$–$C_8$)-alkyl which can optionally be substituted by 1 to 8 fluorine atoms, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, ($C_3$–$C_8$)-cycloalkyl, ($C_3$–$C_8$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)- tricycloalkyl-($C_1$–$C_8$)-alkyl, ($C_2$–$C_8$)-alkenyl, ($C_2$–$C_8$)-alkynyl, $R^{11}$NH, COOR$^{21}$, CON(CH$_3$)R$^4$, CONHR$^4$, COOR$^{15}$, CON(CH$_3$)R$^{15}$ or CONHR$^{15}$;

$R^4$ is hydrogen or ($C_1$–$C_8$)-alkyl which is unsubstituted or monosubstituted or polysubstituted by identical or different radicals selected from the group of hydroxyl, ($C_1$–$C_8$)-alkoxy, $R^5$, optionally substituted ($C_3$–$C_8$)-cycloalkyl, hydroxycarbonyl, aminocarbonyl, mono- or di-(($C_1$–$C_{10}$)-alkyl)-aminocarbonyl, ($C_6$–$C_{14}$)-aryl-($C_1$–$C_8$)-alkoxycarbonyl which can also be substituted in the aryl radical, ($C_1$–$C_8$)-alkoxycarbonyl, $R^6$—CO, $R^7$—CO, tetrazolyl and trifluoromethyl;

$R^5$ is optionally substituted ($C_6$–$C_{14}$)-aryl, ($C_6$–$C_{14}$)-aryl-($C_1$–$C_8$)-alkyl optionally substituted in the aryl radical or a radical of an optionally substituted monocyclic or bicyclic, 5-membered to 12-membered heterocyclic ring, which can be aromatic, partially saturated or completely saturated and which can contain one, two or three identical or different heteroatoms selected from the group of nitrogen, oxygen and sulfur;

$R^6$ is the radical of a natural or unnatural amino acid, imino acid, optionally N—($C_1$–$C_8$)-alkylated or N—(($C_6$–$C_{14}$)-aryl-($C_1$–$C_8$)-alkylated) azaamino acid, which can also be substituted in the aryl radical, or the radical of a dipeptide, tripeptide or tetrapeptide, as well as their esters and amides, in which free functional groups can be protected by protective groups customary in peptide chemistry and in which the nitrogen atoms in the amide bonds in the group $R^6$—CO can carry a radical R as a substituent;

$R^7$ is the radical of a 5-membered to 10-membered, saturated monocyclic or polycyclic heterocycle bonded via a nitrogen atom, which can contain one, two, three or four identical or different additional ring heteroatoms selected from the group of oxygen, nitrogen and sulfur and which can optionally be substituted on carbon atoms and on additional ring nitrogen atoms, in which additional ring nitrogen atoms can carry identical or different radicals selected from the group of hydrogen, $R^h$, HCO, $R^h$CO, $R^h$O—CO, HO—CO—($C_1$–$C_4$)-alkyl and $R^h$O—CO—($C_1$–$C_4$)-alkyl as substituents and $R^h$ is ($C_1$–$C_8$)-alkyl, ($C_3$–$C_8$)-cycloalkyl, ($C_3$–$C_8$)-cycloalkyl-($C_1$–$C_8$)-alkyl, optionally substituted ($C_6$–$C_{14}$)-aryl or ($C_6$–$C_{14}$)-aryl-($C_1$–$C_8$)-alkyl optionally substituted in the aryl radical;

$R^8$ is hydrogen, ($C_1$–$C_6$)-alkyl, optionally substituted ($C_6$–$C_{10}$)-aryl or ($C_6$–$C_{10}$)-aryl-($C_1$–$C_6$)-alkyl which can also be substituted in the aryl radical;

$R^{10}$ is hydroxyl, ($C_1$–$C_8$)-alkoxy, ($C_6$–$C_{12}$)-aryl-($C_1$–$C_8$)-alkoxy which can also be substituted in the aryl radical, optionally substituted ($C_6$–$C_{12}$)-aryloxy, ($C_1$–$C_8$)-alkylcarbonyloxy-($C_1$–$C_6$)-alkoxy, ($C_6$–$C_{12}$)-aryl-($C_1$–$C_6$)-alkylcarbonyloxy-($C_1$–$C_6$)-alkoxy optionally substituted in the aryl radical, ($C_1$–$C_8$)-alkoxycarbonyloxy-($C_1$–$C_6$)-alkoxy, ($C_6$–$C_{12}$)-aryl-($C_1$–$C_6$)-alkoxycarbonyloxy-($C_1$–$C_6$)-alkoxy optionally substituted in the aryl radical, amino, mono- or di-(($C_1$–$C_8$)-alkyl)-amino, aminocarbonyl-($C_1$–$C_6$)-alkoxy, (mono- or di-(($C_1$–$C_8$)-alkyl)-amino)carbonyl-($C_1$–$C_6$)-alkoxy, (mono- or di-(($C_6$–$C_{12}$)-aryl-($C_1$–$C_6$)-alkyl))-amino)-carbonyl-($C_1$–$C_6$)-alkoxy or (N-(($C_1$–$C_8$)-alkyl)-N-(($C_6$–$C_{12}$)-aryl-($C_1$–$C_6$)-alkyl)-amino)-carbonyl-($C_1$–$C_6$)-alkoxy both optionally substituted in the aryl radical;

$R^{11}$ is hydrogen, $R^{12a}$, $R^{12a}$—CO, $R^{12a}$—O—CO, $R^{12b}$—CO, $R^{12b}$—CS or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, or the radical $R^{15}$;

$R^{12b}$ is amino, di-(($C_1$–$C_{10}$)-alkylamino or $R^{12a}$—NH;

$R^{13}$ is hydrogen or ($C_1$–$C_6$)-alkyl;

$R^{15}$ is $R^{16}$($C_1$–$C_6$)-alkyl or $R^{16}$;

$R^{16}$ is a 6-membered to 14-membered, bicyclic or tricyclic radical which is saturated or partially unsaturated and which can also contain one, two, three or four identical or different heteroatoms selected from the group of nitrogen, oxygen and sulfur and which can also be substituted by one or more identical or different substituents selected from the group of ($C_1$–$C_4$)-alkyl and oxo;

$R^{20}$ is a direct bond or ($C_1$–$C_4$)-alkylene;

$R^{21}$ is hydrogen, ($C_1$–$C_8$)-alkyl, ($C_3$–$C_{10}$)-cycloalkyl, ($C_3$–$C_{10}$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, the radical Het- or Het-($C_1$–$C_6$)-alkyl, where alkyl radicals can be monosubstituted or polysubstituted by fluorine and the radicals $R^{21}$, if they occur more than once, can be identical or different;

$R^{22}$ is one of the radicals $R^{21}$—, $R^{21}$N($R^{21}$)—, $R^{21}$C(O)—, $R^{21}$O—C(O)— or $R^{21}$N($R^{21}$)—C(=N($R^{21}$))—;

$R^{30}$ is one of the radicals $R^{32}$(R)N—CO—N(R)—$R^{31}$, $R^{32}$(R)N—CS—N(R)—$R^{31}$, $R^{32}$(R)N—S(O)$_n$—N(R)—$R^{31}$, $R^{32}$—CO—N(R)—$R^{31}$, $R^{32}$—S(O)$_n$—N(R)—$R^{31}$, $R^{32}$(R)N—CO—$R^{31}$, $R^{32}$(R)N—S(O)$_n$—$R^{31}$, $R^{32}$—CO—$R^{31}$, $R^{32}$—S(O)$_n$—$R^{31}$ or $R^{12a}$—O—CO—N(R)—$R^{31}$, where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_1$–$C_8$)-alkyl which can optionally be substituted by 1 to 8 fluorine atoms, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical;

$R^{33}$ is a direct bond or a divalent ($C_1$–$C_6$)-alkylene radical;

$R^{34}$ is a divalent radical selected from the group of ($C_1$–$C_8$)-alkylene, ($C_5$–$C_{10}$)-cycloalkylene, ($C_6$–$C_{12}$)-bicycloalkylene, optionally substituted ($C_6$–$C_{14}$)-arylene and optionally substituted heteroarylene:

$R^{35}$ is a direct bond or a divalent ($C_1$–$C_8$)-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1, 2, 3 or 4 identical or different heteroatoms selected from the group of N and O as ring members and which can optionally be substituted by one or more, identical or different substituents;

e and h independently of one another are 0 or 1;

n is 1 or 2, where the numbers n, if they occur more than once, are independent of one another and can be identical or different;

in all their stereoisomeric forms and mixtures thereof in all ratios, and their physiologically tolerable salts.

Very particularly preferred compounds of the formula are those compounds in which W is a divalent radical selected from the group of $R^1$—A—$C(R^{13})$ and

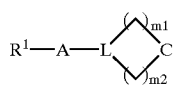

in which the ring systems

can contain one or two identical or different heteroatoms selected from the group of N and O, can be saturated or monounsaturated and can be substituted by 1 or 2 identical or different substituents $R^{13}$ and/or by one or two doubly bonded oxygen atoms, and in which L is $C(R^{13})$ or N and in which m1 and m2 independently of one another are one of the numbers 0, 1, 2, 3 and 4, the sum m1+m2, however, is one of the numbers 1, 2, 3 and 4;

Y is a carbonyl group or thiocarbonyl group;

A is a direct bond, one of the divalent radicals $(C_1-C_6)$-alkylene, $(C_5-C_6)$-cycloalkylene, phenylene, phenylene-$(C_1-C_4)$-alkyl or a divalent radical of a 5-membered or 6-membered, saturated or unsaturated heterocycle which can contain one or two nitrogen atoms and can be monosubstituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent methylene radical or ethylene radical where the methylene radical and the ethylene radical are unsubstituted or are substituted by one or two identical or different radicals selected from the group of $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^{10}CO$, HO—$CH_2$ or $R^8CO$—O—$CH_2$;

R is hydrogen or $(C_1-C_8)$-alkyl, where all radicals R are independent of one another and the radicals R can be identical or different;

$R^1$ is hydrogen, $(C_1-C_{10})$-alkyl, which can optionally be monosubstituted or polysubstituted by fluorine, $R^{21}$—$((C_6-C_{10})$-aryl) optionally substituted in the aryl radical, $(R^{21}$—$((C_6-C_{10})$-aryl-$(C_1-C_6)$-alkyl option-ally substituted in the aryl radical, the radical Het-, Het-$(C_1-C_6)$-alkyl or one of the radicals X—NH—C$(=NH)$—$R^{20}$, $X^1$—NH—$R^{20}$—, $R^{22}N(R^{21})$—C(O)—, O= and S=;

X is hydrogen, $(C_1-C_6)$-alkyl, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl, optionally substituted $(C_6-C_{10})$-arylcarbonyl, optionally substituted $(C_6-C_{10})$-aryloxycarbonyl, $(C_6-C_{14})$-aryl-$(C_1-C_6)$-alkoxycarbonyl which can also be substituted in the aryl radical, hydroxyl, $(C_1-C_6)$-alkoxy, or amino;

$X^1$ has one of the meanings of X or is R'—NH—C(=N—R''), in which R' and R'' independently of one another have the meanings of X;

$R^2$ is hydrogen or $(C_1-C_8)$-alkyl;

$R^3$ is hydrogen, $(C_1-C_8)$-alkyl, which can optionally be substituted by 1 to 6 fluorine atoms, optionally substituted $(C_6-C_{10})$-aryl, $(C_6-C_{10})$-aryl-$(C_1-C_6)$-alkyl optionally substituted in the aryl radical, optionally substituted heteroaryl, heteroaryl-$(C_1-C_6)$-alkyl optionally substituted in the heteroaryl radical, $(C_3-C_8)$-cycloalkyl, $(C_3-C_8)$-cycloalkyl-$(C_1-C_6)$-alkyl, $(C_6-C_{12})$-bicycloalkyl, $(C_6-C_{12})$-bicycloalkyl-$(C_1-C_6)$-cycloalkyl, $(C_6-C_{12})$-tricycloalkyl, $(C_6-C_{12})$-tricycloalkyl-$(C_1-C_6)$-alkyl, $(C_2-C_8)$-alkenyl, $(C_2-C_8)$-alkynyl, $R^{11}NH$, $COOR^{21}$, $CON(CH_3)R^4$, $CONHR^4$, $CON(CH_3)R^{15}$ or $CONHR^{15}$;

$R^4$ is $(C_1-C_8)$-alkyl which is unsubstituted or monosubstituted or disubstituted by identical or different radicals selected from the group of hydroxyl, $(C_1-C_8)$-alkoxy, $R^5$, optionally substituted $(C_3-C_8)$-cycloalkyl, hydroxycarbonyl, aminocarbonyl, $(C_6-C_{10})$-aryl-$(C_1-C_4)$-alkoxycarbonyl which can also be substituted in the aryl radical, $(C_1-C_6)$-alkoxycarbonyl, $R^6$—CO, $R^7$—CO, tetrazolyl and trifluoromethyl;

$R^5$ is optionally substituted $(C_6-C_{12})$-aryl, $(C_6-C_{12})$-aryl-$(C_1-C_8)$-alkyl optionally substituted in the aryl radical or a radical of an optionally substituted monocyclic or bicyclic, 5-membered to 12-membered heterocyclic ring, which can be aromatic, partially saturated or completely saturated and which can contain one, two or three identical or different heteroatoms selected from the group of nitrogen, oxygen and sulfur;

$R^6$ is the radical of a natural or unnatural amino acid, imino acid, optionally N-$(C_1-C_8)$-alkylated or N-$((C_6-C_{12})$-aryl-$(C_1-C_8)$-alkylated) azaamino acid, which can also be substituted in the aryl radical, or the radical of a dipeptide or tripeptide, as well as their esters and amides, in which free functional groups can be protected by protective groups customary in peptide chemistry and in which the nitrogen atoms in the amide bonds in the group $R^6$—CO can carry a radical R as a substituent;

$R^7$ is the radical of a 5-membered to 7-membered, saturated monocyclic or bicyclic heterocycle bonded via a nitrogen atom, which can contain one, two, three or four identical or different additional ring heteroatoms selected from the group of oxygen, nitrogen and sulfur and which can optionally be substituted on carbon atoms and on additional ring nitrogen atoms, in which additional ring nitrogen atoms can carry identical or different radicals selected from the group of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_6)$-alkyl, $(C_3-C_8)$-cycloalkyl, $(C_3-C_8)$-cycloalkyl-$(C_1-C_8)$-alkyl, optionally substituted ($C_6$–$C_{10}$)-aryl or ($C_6$–$C_{10}$)-aryl-($C_1$–$C_4$)-alkyl optionally substituted in the aryl radical;

$R^8$ is hydrogen, ($C_1$–$C_6$)-alkyl or phenyl-($C_1$–$C_4$)-alkyl optionally substituted in the phenyl radical, $R^{10}$ is hydroxyl, ($C_1$–$C_8$)-alkoxy, ($C_6$–$C_{10}$)-aryl-($C_1$–$C_6$)-alkoxy which can also be substituted in the aryl radical, optionally substituted ($C_6$–$C_{10}$)-aryloxy, ($C_1$–$C_6$)-alkylcarbonyloxy($C_1$–$C_6$)-alkoxy, ($C_1$–$C_6$)-alkoxycarbonyloxy-($C_1$–$C_6$)-alkoxy, amino, mono- or di-(($C_1$–$C_6$)-alkyl)-amino, aminocarbonyl-($C_1$–$C_6$)-alkoxy or (mono- or di-(($C_1$–$C_6$)-alkyl)-amino)-carbonyl-($C_1$–$C_6$)-alkoxy;

$R^{11}$ is hydrogen, $R^{12a}$, $R^{12a}$—CO, $R^{12a}$—O—CO, $R^{12b}$—CO or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, or the radical $R^{15}$;

$R^{12b}$ is amino, di-(($C_1$–$C_{10}$)-alkyl)-amino or $R^{12a}$—NH;

$R^{13}$ is hydrogen or ($C_1$–$C_6$)-alkyl;

$R^{15}$ is $R^{16}$—($C_1$–$C_6$)-alkyl or $R^{16}$;

$R^{16}$ is a 6-membered to 14-membered, bicyclic or tricyclic radical which is saturated or partially unsaturated and which can also contain one, two, three or four identical or different heteroatoms selected from the group of nitrogen, oxygen and sulfur and which can also be substituted by one or more identical or different substituents selected from the group of ($C_1$–$C_4$)-alkyl and oxo;

$R^{20}$ is a direct bond or ($C_1$–$C_2$)-alkylene;

$R^{21}$ is hydrogen, ($C_1$–$C_6$)-alkyl, ($C_3$–$C_6$)-cycloalkyl, ($C_3$–$C_6$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, the radical Het- or Het-($C_1$–$C_4$)-alkyl, where alkyl radicals can be monosubstituted or polysubstituted by fluorine and the radicals $R^{21}$, if they occur more than once, can be identical or different;

$R^{22}$ is one of the radicals $R^{21}$—, $R^{21}N(R^{21})$— or $R^{21}N(R^{21})$—C(=N($R^{21}$))—;

$R^{30}$ is one of the radicals $R^{32}(R)N$—CO—N(R)—$R^{31}$, $R^{32}(R)N$—CS—N(R)—$R^{31}$, $R^{32}$—CO—N(R)—$R^{31}$ or $R^{32}(R)N$—CO—$R^{31}$, where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_1$–$C_6$)-alkyl which can optionally be substituted by 1 to 6 fluorine atoms, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl or heteroaryl-($C_1$–$C_6$)-alkyl optionally substituted in the heteroaryl radical;

$R^{33}$ is a direct bond or a divalent ($C_1$–$C_4$)-alkylene radical;

$R^{34}$ is a divalent radical selected from the group of ($C_1$–$C_6$)-alkylene, ($C_5$–$C_6$)-cycloalkylene, optionally substituted ($C_6$–$C_{10}$)-arylene and optionally substituted heteroarylene;

$R^{35}$ is a direct bond or a divalent ($C_1$–$C_4$)-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1 or 2 identical or different heteroatoms selected selected from the group of N and O as ring members and which can optionally be substituted by one or more, identical or different substituents;

e and h independently of one another are 0 or 1;

n is 1 or 2;

in all their stereoisomeric forms and mixtures thereof in all ratios, and their physiologically tolerable salts.

Additionally preferred compounds of the formula I are those in which

W is the divalent radical $R^1$—A—C($R^{13}$),

Y is a carbonyl group;

A is a direct bond, one of the divalent radicals ($C_1$–$C_6$)-alkylene, phenylene, phenylene-($C_1$–$C_2$)-alkyl or a divalent radical of a 5-membered or 6-membered, saturated or unsaturated heterocycle which can contain one or two nitrogen atoms and can be monosubstituted or disubstituted by ($C_1$–$C_6$)-alkyl or doubly bonded oxygen or sulfur, where in the radicals phenylenealkyl and phenylenealkenyl the radical $R^1$ is bonded to the phenylene group;

B is a divalent methylene radical or ethylene radical where the methylene radical and the ethylene radical are unsubstituted or are substituted by a radical selected from the group of ($C_1$–$C_8$)-alkyl, ($C_2$–$C_8$)-alkenyl, ($C_2$–$C_8$)-alkynyl, ($C_3$–$C_6$)-cycloalkyl, ($C_3$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

E is $R^{10}$CO, HO—CH$_2$ or $R^8$CO—O—CH$_2$.

R is hydrogen or ($C_1$–$C_8$)-alkyl where all radicals R are independent of one another and the radicals R can be identical or different;

$R^1$ is hydrogen, ($C_1$–$C_{10}$)-alkyl, which can optionally be monosubstituted or polysubstituted by fluorine, $R^{21}$(($C_6$–$C_{10}$)-aryl) optionally substituted in the aryl radical, ($R^{21}$(($C_6$–$C_{10}$)-aryl)-($C_1$–$C_6$)-alkyl optionally substituted in the aryl radical, the radical Het-, Het-($C_1$–$C_4$)-alkyl or one of the radicals X—NH—C(=NH)—$R^{20}$—, $X^1$—NH—$R^{20}$—, and O=;

X is hydrogen, ($C_1$–$C_6$)-alkyl, ($C_1$–$C_6$)-alkylcarbonyl, ($C_1$–$C_6$)-alkoxycarbonyl, ($C_1$–$C_6$)-alkylcarbonyloxy-($C_1$–$C_6$)-alkoxycarbonyl, optionally substituted ($C_6$–$C_{10}$)-arylcarbonyl, optionally substituted ($C_6$–$C_{10}$)-aryloxycarbonyl, ($C_6$–$C_{14}$)-aryl-($C_1$–$C_6$)-alkoxycarbonyl which can also be substituted in the aryl radical, hydroxyl, ($C_1$–$C_6$)-alkoxy or amino;

$X^1$ has one of the meanings of X or is R'—NH—C(=N—R"), in which R' and R" independently of one another have the meanings of X;

$R^2$ is hydrogen or ($C_1$–$C_6$)-alkyl;

$R^3$ is hydrogen, ($C_1$–$C_8$)-alkyl, which can optionally be substituted by 1 to 6 fluorine atoms, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, $(C_3-C_8)$-alkyl, $(C_3-C_8)$-cycloalkyl-$(C_1-C_4)$-alkyl, $(C_6-C_{12})$-bicycloalkyl, $(C_6-C_{12})$-bicycloalkyl-$(C_1-C_4)$-alkyl, $(C_6-C_{12})$-tricycloalkyl, $(C_6-C_{12})$-tricycloalkyl-$(C_1-C_4)$-alkyl, $(C_2-C_8)$-alkenyl, $(C_2-C_8)$-alkynyl, $R^{11}NH$, $COOR^{21}$, $CON(CH_3)R^4$, $CONHR^4$, $CON(CH_3)R^{15}$ or $CONHR^{15}$;

$R^4$ is $(C_1-C_6)$-alkyl which is unsubstituted or monosubstituted or disubstituted by identical or different radicals selected from the group of hydroxyl, $(C_1-C_8)$-alkoxy, $R^5$, optionally substituted $(C_3-C_8)$-cycloalkyl, hydroxycarbonyl, aminocarbonyl, $(C_6-C_{10})$-aryl-$(C_1-C_4)$-alkoxycarbonyl, which can also be substituted in the aryl radical, $(C_1-C_6)$-alkoxycarbonyl, $R^6$—CO, $R^7$—CO, tetrazolyl and trifluoromethyl;

$R^5$ is optionally substituted $(C_6-C_{10})$-aryl, $(C_6-C_{10})$-aryl-$(C_1-C_4)$-alkyl optionally substituted in the aryl radical or a radical of an optionally substituted monocyclic or bicyclic, 5-membered to 12-membered heterocyclic ring, which can be aromatic, partially saturated or completely saturated and which can contain one, two or three identical or different heteroatoms selected from the group of nitrogen, oxygen and sulfur;

$R^6$ is a radical of a natural or unnatural amino acid or the radical of a dipeptide or tripeptide, as well as their esters and amides, in which free functional groups can be protected by protective groups customary in peptide chemistry and in which the nitrogen atoms in the amide bonds in the group $R^6$—CO can carry a radical R as a substituent;

$R^7$ is the radical of a 5-membered to 7membered, saturated monocyclic heterocycle bonded via a nitrogen atom, which can contain one or two identical or different additional ring heteroatoms selected from the group of oxygen, nitrogen and sulfur and which can optionally be substituted on carbon atoms and on additional ring nitrogen atoms, in which additional ring nitrogen atoms can carry identical or different radicals selected from the group of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_4)$-alkyl, optionally substituted $(C_6-C_{10})$-aryl or $(C_6-C_{10})$-aryl-$C_1-C_4$)-alkyl optionally substituted in the aryl radical;

$R^8$ is hydrogen, $(C_1-C_6)$-alkyl or phenyl-$(C_1-C_4)$-alkyl optionally substituted in the phenyl radical, $R^{10}$ is hydroxyl, $(C_1-C_8)$-alkoxy, $(C_6-C_{10})$-aryl-$(C_1-C_6)$-alkoxy which can also be substituted in the aryl radical, optionally substituted $(C_6-C_{10})$-aryloxy, $(C_1-C_6)$-alkylcarbonyloxy-$(C_1-C_6)$-alkoxy, $(C_1-C_6)$-alkoxycarbonyloxy-$(C_{1-C6})$-alkoxy, amino, mono- or di-(($C_1-C_6)$-alkyl)-amino, aminocarbonyl-$(C_1-C_6)$-alkoxy or (mono- or di-(($C_1-C_6)$-alkyl)-amino)-carbonyl)-$(C_1-C_6)$-alkoxy;

$R^{11}$ is hydrogen $R^{12a}$, $R^{12a}$—CO, $R^{12a}$—O—CO, $R^{12b}$—CO, or $R^{12a}$—S(O)$_2$;

$R^{12a}$ is $(C_1-C_8)$-alkyl, $(C_2-C_8)$-alkenyl, $(C_2-C_8)$-alkynyl, $(C_5-C_6)$-cycloalkyl, $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl, heteroaryl-$(C_1-C_4)$-alkyl optionally substituted in the heteroaryl radical, or the radical $R^{15}$;

$R^{12b}$ is amino, di-(($C_1-C_8)$-alkyl)-amino or $R^{12a}$—NH;

$R^{13}$ is hydrogen or $(C_1-C_6)$-alkyl;

$R^{15}$ is $R^{16}$—$(C_1-C_6)$-alkyl or $R^{16}$;

$R^{16}$ is a 6-membered to 12-membered, bicyclic or tricyclic radical which is saturated or partially unsaturated and which can also contain one, two, three or four identical or different heteroatoms selected from the group of nitrogen, oxygen and sulfur and which can also be substituted by one or more identical or different substituents selected from the group of $(C_1-C_4)$-alkyl and oxo;

$R^{20}$ is a direct bond or methylene;

$R^{21}$ is hydrogen, $(C_1-C_6)$-alkyl, optionally substituted $(C_6-C_{10})$-aryl, $(C_6-C_{10})$-aryl-$(C_1-C_2)$-alkyl optionally substituted in the aryl radical, the radical Het- or Het-$(C_1-C_2)$-alkyl, where alkyl radicals can be monosubstituted to tetrasubstituted by fluorine and the radicals $R^{21}$, if they occur more than once can be identical or different;

$R^{30}$ is one of the radicals $R^{32}(R)N$—CO—N(R)—$R^{31}$ or $R^{32}(R)N$—CS—N(R)—$R^{31}$, $R^{31}$ is a divalent radical selected from the group of $(C_1-C_6)$-alkylene, optionally substituted $(C_6-C_{10})$-arylene, $(C_6-C_{10})$-arylene-$(C_1-C_4)$-alkyl optionally substituted in the arylene radical, $(C_5-C_6)$-cycloalkylene, $(C_5-C_6)$-cycloalkylene-$(C_1-C_4)$-alkyl, optionally substituted heteroarylene or heteroarylene-$(C_1-C_4)$-alkyl optionally substituted in the heteroarylene radical, where in the case of the arylenealkyl radical, of the cycloalkylenealkyl radical and of the heteroarylenealkyl radical the alkyl group is bonded to the nitrogen atom in the imidazolidine ring in the formula I;

$R^{32}$ is hydrogen, $(C_1-C_6)$-alkyl which can optionally be substituted by 1 to 6 fluorine atoms, $(C_2-C_6)$-alkenyl, $(C_2-C_6)$-alkynyl, $(C_5-C_6)$-cycloalkyl, $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl or heteroaryl-$(C_1-C_4)$-alkyl optionally substituted in the heteroaryl radical;

Het is a radical of a monocyclic or polycyclic, 5-membered to 10-membered, aromatic or nonaromatic ring which contains 1 or 2 identical or different heteroatoms from the group consisting of N and O as ring members and which can optionally be substituted by one or more, identical or different substituents;

e and h independently of one another are 0 or 1;

in all their stereoisomeric forms and mixtures thereof in all ratios, and their physiologically tolerable salts.

A series of especially preferred compounds includes those compounds of the formula I in which B is unsubstituted methylene or methylene which is substituted by a $(C_1-C_8)$-alkyl radical, in all their stereoisomeric forms and mixtures thereof in all ratios, and their physiologically tolerable salts. Particularly especially preferred in this series are compounds of the formula I in which B is methylene which is substituted by a $(C_1-C_8)$-alkyl radical, in all their stereoisomeric forms and mixtures thereof in all ratios, and their physiologically tolerable salts.

A further series of especially preferred compounds includes those compounds of the formula I in which $R^{30}$ is a radical selected from the group of $R^{32}(R)N$—CO—N(R)—$R^{31}$ and $R^{32}(R)N$—CS—N(R)—$R^{31}$ and $R^{31}$ is a divalent radical selected from the group of $(C_1-C_6)$-alkylene and $(C_6-C_{10})$-arylene-$(C_1-C_4)$-alkyl optionally substituted in the arylene radical, where in the case of the arylenealkyl radical the alkyl group is bonded to the nitrogen atom in the imidazolidine ring in the formula I, in all their stereoisomeric forms and mixtures thereof in all ratios, and their physiologically tolerable salts. In this series, additionally preferred compounds of the formula I are those in which $R^{30}$ is the radical $R^{32}NH$—CO—NH—$R^{31}$ and therein $R^{32}$ is optionally substituted phenyl and $R^{31}$ is the divalent radical 1,4-phenylenemethyl (i.e. —(1,4-$C_6H_4$)—$CH_2$—), in which the methyl group is bonded to the nitrogen atom in the imidazolidine ring in the formula I, in all their stereoisomeric forms and mixtures thereof in all ratios, and their physiologically tolerable salts.

A further series of especially preferred compounds includes those compounds of the formula I in which $R^{13}$ is hydrogen or methyl, in all their stereoisomeric forms and mixtures thereof in all ratios, and their physiologically tolerable salts. Particularly especially preferred in this series are compounds of the formula I in which the group $R^1$—A— is not hydrogen and at the same time the group $R^{13}$ is also not hydrogen, i.e. compounds in which W is not $CH_2$, in all their stereoisomeric forms and mixtures thereof in all ratios, and their physiologically tolerable salts, where it is very particularly especially preferred if, in these compounds, $R^{13}$ is methyl, i.e., if compounds are present in which W is the divalent radical $R^1$—A—$C(CH_3)$ and therein $R^1$—A— has a meaning other than hydrogen.

A further series of especially preferred compounds includes those compounds of the formula I in which at the same time the radicals $R^{13}$ and $R^1$—A— are other than hydrogen, $R^{30}$ is the radical $R^{32}$—NH—CO—NH—(1,4-$C_6H_4$)—$CH_2$, in which the group —(1,4-$C_6H_4$)— is a phenylene radical linked via the positions 1 and 4, and $R^{32}$ is optionally substituted phenyl, in all their stereoisomeric forms and mixtures thereof in all ratios, and their physiologically tolerable salts.

A further series of especially preferred compounds includes those compounds of the formula I in which at the same time the radicals $R^{13}$ and $R^1$—A— are other than hydrogen, $R^{30}$ is the radical $R^{32}$—NH—CO—NH—(1,4-$C_6H_4$)—$CH_2$, $R^{32}$ is optionally substituted phenyl and B is a divalent methylene radical which is unsubstituted or—in a preferred form—is substituted by ($C_1$–$C_6$)-alkyl or ($C_3$–$C_6$)-cycloalkyl-($C_1$–$C_2$)-alkyl, in all their stereoisomeric forms and mixtures thereof in all ratios, and their physiologically tolerable salts.

A further series of especially preferred compounds includes those compounds of the formula I in which at the same time the radicals $R^{13}$ and $R^1$—A— are other than hydrogen, $R^{30}$ is the radical $R^{32}$—NH—CO—NH—(1,4-$C_6H_4$)—$CH_2$, $R^{32}$ is optionally substituted phenyl, B is a divalent methylene radical which is unsubstituted or—in a preferred form—is substituted by ($C_1$–$C_6$)-alkyl or ($C_3$–$C_6$)-cycloalkyl-($C_1$–$C_2$)-alkyl, and the radical —N(R)—[C(R)(R)]$_e$—C($R^2$)($R^3$)—[C(R)(R)]$_h$—E in the formula I is the radical —NH—CH($R^3$)—$CH_2$—E, in all their stereoisomeric forms and mixtures thereof in all ratios, and their physiologically tolerable salts.

A further series of especially preferred compounds includes those compounds of the formula I in which at the same time W is one of the divalent radicals 1,1-cyclopropylidene, 1,1-cyclopentylidene and 1,1-cyclohexylidene, which are explained in greater detail above, where the radicals derived from the 5-membered ring and from the 6-membered ring can in each case carry a doubly bonded oxygen atom as substituents, $R^{30}$ is the radical $R^{32}$—NH—CO—NH—(1,4-$C_6H_4$)—$CH_2$ and $R^{32}$ is optionally substituted phenyl, in all their stereoisomeric forms and mixtures thereof in all ratios, and their physiologically tolerable salts.

A further series of especially preferred compounds includes those compounds of the formula I in which at the same time W is one of the divalent radicals 1,1-cyclopropylidene, 1,1-cyclopentylidene and 1,1-cyclohexylidene, $R^{30}$ is the radical $R^{32}$—NH—CO—NH—(1,4-$C_6H_4$)—$CH_2$, $R^{32}$ is optionally substituted phenyl and B is a divalent methylene radical which is unsubstituted or—in a preferred form—is substituted by ($C_1$–$C_6$)-alkyl or ($C_3$–$C_6$)-cycloalkyl-($C_1$–$C_2$)-alkyl, in all their stereoisomeric forms and mixtures thereof in all ratios, and their physiologically tolerable salts.

A further series of especially preferred compounds includes those compounds of the formula I in which at the same time W is one of the divalent radicals 1,1-cyclopropylidene, 1,1-cyclopentylidene and 1,1-cyclohexylidene, $R^{30}$ is the radical $R^{32}$—NH—CO—NH—(1,4-$C_6H_4$)-$CH_2$, $R^{32}$ is optionally subs d phenol, B is a divalent methylene radical which is unsubstituted or—in a preferred form—is substituted by ($C_1C_6$)-alkyl or ($C_3$–$C_6$)-cycloalkyl-($C_1$–$C_2$)-alkyl, and the radical —N(R)—[C(R)(R)]$_e$—C($R^2$)($R^3$)—[C(R)(R)]$_h$—E in the formula I is the radical —NH—CH($R^3$)—$CH_2$—E, in all their stereoisomeric forms and mixtures thereof in all ratios, and their physiologically tolerable salts.

A further series of especially preferred compounds includes those compounds of the formula I in which in the radical —N(R)—[(R)(R)]$_e$—C($R^2$)($R^3$)—[C(R)(R)]$_h$—E which is linked to the group —B—CO— by an amide bond, the chain of carbon atoms between the group N(R) and the first group bonded to this chain which is an acid group such as a carboxylic acid group, sulfonic acid group, phosphonic acid group or tetrazolyl group or a derivative thereof such as an ester or an amide, comprises two or more than two carbon atoms, in all their stereoisomeric forms and mixtures thereof in all ratios, and their physiologically tolerable salts. This first acid group (or the derivative thereof) which, starting from the group N(R), is bonded to this chain of carbon atoms can be the group E or can be the group $R^3$, if the latter is, for example, $COOR^{21}$, $CONHR^4$, $COR^6$, $COR^7$ etc. Particularly especially preferred compounds in this series are those of the formula I in which, in the radical —N(R)—[C(R)(R)]$_e$—C($R^2$)($R^3$)—[C(R)(R)]$_h$—E, the chain of carbon atoms between the group N(R) and the first group bonded to this chain, which is an acid group or a derivative thereof, comprises exactly two carbon atoms, in all their stereoisomeric forms and mixtures thereof in all ratios, and their physiologically tolerable salts. Particularly especially preferred compounds of the formula I of this type can be, for example, compounds in which e is 1, i.e., compounds which contain the group —N(R)—C(R)(R)—C($R^2$)($R^3$)—[C(R)(R)]$_h$—E, where in the case of these compounds h can be 1 or 0 and where it is preferred in the case of these compounds if $R^3$ is $R^{11}NH$ and at the same time h is 0, in all their stereoisomeric forms and mixtures thereof in all ratios, and their physiologically tolerable salts. Particularly especially preferred compounds of the formula I of this type can also be, for example, compounds in which e is 0, h is 1 and $R^3$ is not an acid group or a derivative thereof, in all their stereoisomeric forms and mixtures thereof in all ratios, and their physiologically tolerable salts, i.e. compounds which contain a radical —N(R)—C($R^2$)($R^{3a}$)—C(R)(R)—E, in which $R^{3a}$ is defined as $R^3$, but cannot be a carboxylic acid group or a derivative thereof such as an ester or an amide. Preferably, in these compounds, $R^{3a}$ is hydrogen, ($C_1$–$C_8$)-alkyl which can optionally be substituted by 1 to 6 fluorine atoms, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl (C$_1$–C$_8$)-alkyl optionally substituted in the heteroaryl radical, (C$_3$–C$_8$)-cycloalkyl, (C$_3$–C$_8$)-cycloalkyl-(C$_1$–C$_8$)-alkyl, (C$_6$–C$_{12}$)-bicycloalkyl, (C$_6$–C$_{12}$)-bicycloalkyl-(C$_1$–C$_8$)-alkyl, (C$_6$–C$_{12}$)-tricycloalkyl, (C$_6$–C$_{12}$)-tricycloalkyl-(C$_1$–C$_8$)-alkyl, (C$_2$–C$_8$)-alkenyl or (C$_2$–C$_8$)-alkynyl. Particularly preferably, in these compounds, R$^{3a}$ is hydrogen, (C$_1$–C$_6$)-alkyl which can optionally be substituted by 1 to 6 fluorine atoms, optionally substituted (C$_6$–C$_{10}$)-aryl, (C$_6$–C$_{10}$)-aryl-(C$_1$–C$_4$)-alkyl optionally substituted in the aryl radical, optionally substituted heteroaryl, heteroaryl-(C$_1$–C$_4$)-alkyl optionally substituted in the heteroaryl radical, (C$_5$–C$_6$)-cycloalkyl, (C$_5$–C$_6$)-cycloalkyl-(C$_1$–C$_4$)-alkyl, (C$_{10}$–C$_{12}$)-tricycloalkyl or (C$_{10}$–C$_{12}$)-tricycloalkyl-(C$_1$–C$_4$)-alkyl. It is furthermore preferred in the compounds of this series if the group —N(R)— in the radical —N(R)—[C(R)(R)]$_e$—C(R$^2$)(R$^3$—[C(R)(R)]$_h$—E is the group —NH—.

A further series of especially preferred compounds includes those compounds of the formula I in which in the radical —N(R)—[C(R)(R)]$_e$—C(R$^2$)(R$^3$)—[C(R)(R)]$_h$—E the chain of carbon atoms between the group N(R) and the first group bonded to this chain, which is an acid group or a derivative thereof, only comprises one carbon atom, in all their stereoisomeric forms and mixtures thereof in all ratios and their physiologically tolerable salts, where, however, in these compounds the first acid group or the derivative thereof which, starting from the group N(R), is bonded to the chain of carbon atoms, must fulfil the following condition: a) the first acid group or the derivative thereof is an amide group which, however, in an alkyl substituent on the amide nitrogen does not contain a carboxylic acid group (or a derivative thereof such as an ester group or an amide group) bonded to this alkyl substituent, or b) the first acid group is a free acid group (or a salt thereof), or c) the first acid group or the derivative thereof is an ester group. Compounds of this series can be, for example, compounds of the formula I in which e is 0 and R$^3$ is COOR$^{21}$, COOR$^{15}$, CONHR$^{15}$ or CON(CH$_3$)R$^{15}$, preferably CONHR$^{15}$, and h is 0 or 1, preferably 1. Compounds of this series can also be, for example, compounds of the formula I in which e is 0, h is 0 or 1, preferably 1, and R$^3$ is CON(CH$_3$)R$^4$ or CONHR$^4$, but in which a (C$_1$–C$_{10}$)-alkyl radical representing R$^4$ cannot be substituted by a carboxylic acid group or a derivative thereof such as an ester or an amide, i.e., for example, compounds in which R$^4$ is hydrogen or in particular (C$_1$–C$_{10}$)-alkyl which is unsubstituted or substituted by one or more identical or different radicals from the group consisting of hydroxyl, (C$_1$–C$_8$)-alkoxy, R$^5$, optionally substituted (C$_3$–C$_8$)-cycloalkyl, tetrazolyl and trifluoromethyl. In the compounds of this series, E is preferably an acid group or a derivative thereof.

Generally, compounds of the formula I are preferred which have a uniform configuration at one chiral centers or uniform configurations at more than one chiral centers, for example, when appropriately substituted, at the carbon atom carrying the radicals R$^2$ and R$^3$ and/or at the center W in the imidazolidine ring in the formula I. That means, compounds are preferred which are present in a uniform or essentially uniform configuration, either in R configuration or in S configuration, at one or more chiral centers and which are not present at such centers as an R/S mixture. The individual chiral centers in these compounds of the formula I can, however, independently of one another, have the R configuration or the S configuration and can have identical or different configurations.

The compounds of the formula I can be prepared, for example, by fragment condensation of a compound of the formula II

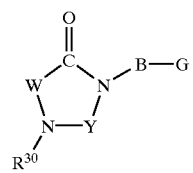
(II)

with a compound of the formula III,

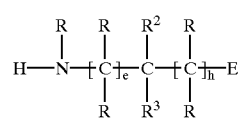
(III)

where, in the formulae II and III, the groups W, Y, B, E, R, R$^2$, R$^3$, R$^{30}$ as well as e and h are defined as indicated above or alternatively functional groups can be contained in protected form or in the form of precursors in these groups, and where G is hydroxycarbonyl, (C$_1$–C$_6$)-alkoxycarbonyl or activated carboxylic acid derivatives such as acid chlorides or active esters. If compounds of the formula I are to be prepared in which, for example, R$^3$ in the formula I is a carboxylic acid derivative or contains such a group, it is also possible that in the compounds of the formula III the radical R$^3$ initially is a hydroxycarbonyl group present in protected form or contains such a group, and that then the desired final group R$^3$ is synthesized in one or more further steps only after the condensation of the compounds of the formulae II and III. Precursors of functional groups are groups which can be converted into the desired functional group according to the customary synthesis processes known to the person skilled in the art. For example, a nitro group can be converted into an amino group by reduction, for example by catalytic hydrogenation, and can be designated as a precursor for an amino group or a group obtainable therefrom by further reactions. A cyano group, which can be converted into an aminomethyl group by reduction or into an acid amide group or a carboxylic acid group by hydrolysis, can be designated as a precursor for these groups. An alcohol group, which can be oxidized to an aldehyde group or a ketone group, can be designated as a precursor for these groups. A precursor for a group, however, can also be a group from which a relatively large part of the target molecule is synthesized in several reaction steps carried out later. Examples of protective groups which are introduced into the molecule before carrying out a reaction or a reaction sequence and are later removed again, are mentioned above.

For the condensation of the compounds of the formula II with those of the formula III, the coupling methods of peptide chemistry well known per se to the person skilled in the art are advantageously used (see, for example, Houben-Weyl, Methoden der Organischen Chemie [Methods of Organic Chemistry], Volume 15/1 and 15/2, Georg Thieme Verlag, Stuttgart, 1974); incorporated by reference herein its entirety. Possible condensing agents or coupling reagents are, for example, carbonyldiimidazole, carbodiimides such as dicyclohexylcarbodiimide (DCC) or diisopropylcarbodiimide, O-((cyano(ethoxy-carbonyl)-methylene)amino)-N,N,N',N'-tetramethyluronium tetrafluoroborate (TOTU) or propylphosphonic anhydride (PPA).

The condensation can be carried out under the standard conditions well known to the person skilled in the art. Often, it is necessary in the condensation to protect nonreacting amino groups present by reversible protective groups. The same applies to carboxyl groups not involved in the reaction, which are preferably present during the condensation as $(C_1-C_6)$-alkyl esters, benzyl esters or tert-butyl esters. Amino group protection is unnecessary if the amino groups are still present in the form of precursors, for example as nitro groups or cyano groups, and are only formed after condensation, for example by hydrogenation. After condensation, the protective groups present are removed in a suitable manner. For example, $NO_2$ groups (guanidino protection in amino acids), benzyloxycarbonyl groups and benzyl groups in benzyl esters can be removed by hydrogenation. The protective groups of the tert-butyl type are removed under acidic conditions, while the 9-fluorenylmethyloxycarbonyl radical is removed by secondary amines. The compounds of the formula I can also be prepared, for example, by synthesizing the compounds stepwise on a solid phase according to customary methods, where the individual structural elements of the molecule can be introduced in a different sequence.

Compounds of the formula II in which W is $R^1$—A—C($R^{13}$) and Y is a carbonyl group can be prepared, for example, by first reacting compounds of the formula IV

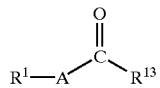

(IV)

in a Bucherer reaction, for example with ammonium carbonate and potassium cyanide, to give compounds of the formula V

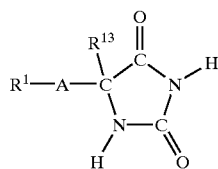

(V)

(H. T. Bucherer, V. A. Lieb, J. Prakt. Chem. 141(1934), 5), where in the formulae IV and V the groups $R^1$, $R^{13}$ and A are defined as indicated above. Compounds of the formula VI

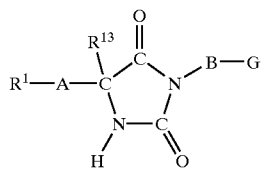

(VI)

in which $R^1$, $R^{13}$, A, B and G are defined as indicated above, can then be obtained by first reacting the compounds of the formula V, for example, with an alkylating reagent which introduces the radical —B—G into the molecule. The reaction of compounds of the formula VI with a second reagent of the formula $R^{30}$—LG, in which $R^{30}$ has the meanings indicated above and LG is a nucleophilically substitutable leaving group, for example halogen, in particular chlorine or bromine. sulfonyloxy such as tosyloxy, methylsulfonyloxy or trifluoromethylsulfonyloxy, $(C_1-C_4)$-alkoxy, optionally substituted phenoxy or a heterocyclic leaving group such as, for example, imidazolyl, then leads to the corresponding compounds of the formula II.

Generally, depending on the meanings of the radical $R^{30}$ and other radicals, it can also be advantageous not to introduce the final radical $R^{30}$ into the molecule by means of the reagent $R^{30}$—LG, but after linking a precursor of the group $R^{30}$ to the imidazolidine ring, to synthesize the radical $R^{30}$ on the imidazolidine ring. This can be carried out, for example, at the stage of a compound of the formula VI or the compound of the formula II prepared therefrom or at the stage of another intermediate of the synthesis. For example, this procedure is shown below on compounds in which $R^{30}$ is the urea group $R^{32}(R)N$—CO—N(R)—$R^{31}$. Compounds of the formula II, in which $R^{30}$ is $R^{32}(R)N$—CO—N(R)—$R^{31}$, can be prepared by this procedure, for example, by first reacting a compound of the formula VI with a reagent of the formula PG—N(R)—$R^{31}$—LG, in which LG again a nucleophilically substitutable leaving group, to give a compound of the formula VII

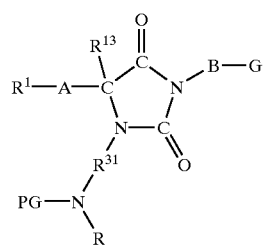

(VII)

where PG is an amino protective group, for example tert-butoxycarbonyl or benzyloxycarbonyl, and where the meanings indicated above otherwise apply. After removing the protective group PG, compounds of the formula II in which $R^{30}$ is $R^{32}NH$—CO—N(R)—$R^{31}$ are then obtained by reaction of the resulting amino group HNR— with, for example, an isocyanate of the formula $R^{32}$—N=C=O. By reaction, for example, with a carbamoyl chloride of the formula $R^{32}(R)N$—CO—Cl, compounds of the formula II are obtained in which $R^{30}$ is $R^{32}(R)N$—CO—N(R)—$R^{31}$. Correspondingly, with isothiocyanates and thiocarbamoyl chlorides the analogous thiourea derivatives are obtainable; by reaction of the amino groups with reactive carboxylic acid derivatives, thiocarboxylic acid derivatives, sulfonic acid derivatives, sulfinic acid derivatives and sulfamoyl chlorides, respectively, (thio)acylamines, sulfonylamines, sulfinylamines and sulfamides are obtainable. Like compounds of the formula VII, also compounds can also be prepared and employed into the synthesis in which in the formula VII the group PG—N(R)— is replaced by a group which is a precursor for an amino group and which is then converted into an amino group in a further reaction step. For example, a compound of the formula VI can first be reacted with a nitro compound of the formula $O_2N$—$R^{31}$—LG or a cyano compound of the formula NC—$R^{31}$—LG to give a compound corresponding to the compound of the formula VII, then the nitro group or the cyano group can be converted into the amino group, for example by catalytic hydrogenation, and then the amino group can be converted into the desired target group, for example using an isocyanate of the formula $R^{32}$—N=C=O to give a urea derivative in which $R^{30}$ is $R^{32}NH$—CO—NH—$R^{31}$, or using other compounds. According to this procedure, numerous further compounds of the formula I can be synthesized, the reactions to be carried out always being standard processes which are familiar to the person skilled in the art.

Very generally, the individual steps in the preparation of the compounds of the formula I can be carried out according to or analogously to known methods familiar to the person skilled in the art. Depending on the individual case, it may be appropriate here, as already explained, in all steps in the synthesis of the compounds of the formula I to temporarily block functional groups which could lead to secondary reactions or undesired reactions by a protective group strategy suited to the synthesis problem, which is known to the person skilled in the art.

The explained procedure of not directly introducing functional groups into the molecule in the final form, but first introducing precursors into the molecule and then synthesizing the final functional group at the stage of an intermediate can correspondingly also be used, as already mentioned, for other parts of the molecule of the formula I, for example for the group $R^1$ or the group $R^3$.

Compounds of the formula II in which W is

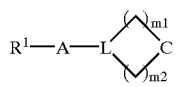

and Y is a carbonyl group, can be prepared, for example, by reacting compounds of the formula VIII

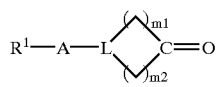
(VIII)

in which $R^1$, A, L, m1 and m2 are defined as indicated above, in a Bucherer reaction as described above for the preparation of the compounds of the formula V, to give compounds of the formula IX

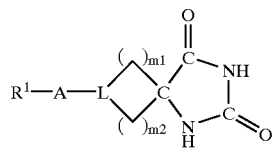
(IX)

and converting these using a reagent which introduces the radical —B—G into the molecule, as described above for the preparation of the compounds of the formula VI, into compounds of the formula X

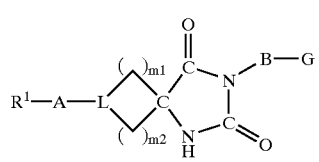
(X)

where in the compounds of the formulae IX and X the groups $R^1$, A, B, G and L and also m1 and m2 have the meanings indicated above. The compounds of the formula X can then be reacted in turn, correspondingly to the reactions of the compounds of the formula VI described above, with a reagent of the formula $R^{30}$—LG or a reagent of the formula PG—N(R)—$R^{31}$—LG.

If W is $R^1$—A—C($R^{13}$)=C or the radical

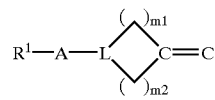

this structural element can be introduced, for example, by condensing the corresponding aldehyde or the corresponding ketone with a dioxo- or thioxooxoimidazolidine, which contains an unsubstituted methylene group in the position which corresponds to the group W, analogously to known methods.

The amino compounds of the formula III are commercially available or can be synthesized from starting compounds which are commercially available or are obtainable according to or analogously to literature procedures according to or analogously to well known standard processes.

Compounds of the formula I in which W is $R^1$—A—C($R^{13}$) can also be obtained as follows:

By reaction of α-amino acids or N-substituted α-amino acids obtainable according to standard processes, or preferably their esters, for example the methyl ester, ethyl ester, tert-butyl ester or benzyl ester, for example of compounds of the formula XI,

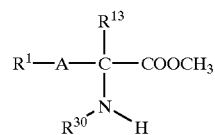
(XI)

in which $R^1$, $R^{13}$, $R^{30}$ and A are defined as indicated above, with an isocyanate or isothiocyanate, for example of the formula XII,

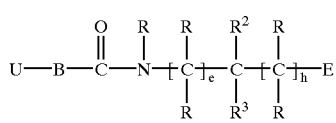
(XII)

in which B, E, R, $R^2$, $R^3$, e and h are defined as indicated above and U is isocyanato or isothiocyanato, urea derivatives or thiourea derivatives are obtained, for example of the formula XIII,

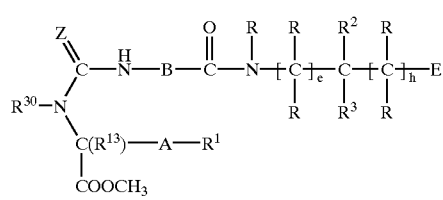
(XIII)

for which the definitions indicated above apply and in which Z is oxygen or sulfur. The compounds of the formula XIII can be cyclized by heating with acid to give compounds of the formula Ia

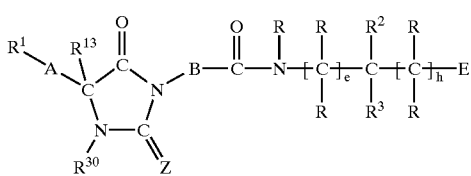

(Ia)

for which the meanings indicated above apply. The cyclization of the compounds of the formula XIII to the compounds of the formula Ia can also be carried out by treatment with bases in inert solvents, for example by treatment with sodium hydride in an aprotic solvent such as dimethylformamide. During the cyclization, functional groups can in turn be present in protected form.

Compounds of the formula I in which W is $R^1$—A—C($R^{13}$) can also be obtained by reacting a compound of the formula XI with an isocyanate or isothiocyanate of the formula XIV

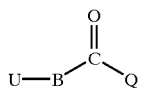

(XIV)

in which B and U are defined as indicated above for the formula XII and Q is an alkoxy group, for example a ($C_1$–$C_4$)-alkoxy group such as methoxy, ethoxy or tert-butoxy, a ($C_6$–$C_{14}$)-aryloxy group, for example phenoxy, or a ($C_6$–$C_{14}$)-aryl-($C_1$–$C_4$)-alkoxy group, for example benzyloxy. In this case, a compound of the formula XV

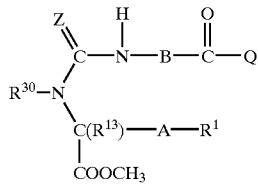

(XV)

is obtained, in which Z is oxygen or sulfur and A, B, Q, $R^1$, $R^{13}$ and $R^{30}$ are defined as indicated above for the formulae XI and XIV, which is then cyclized under the influence of an acid or of a base, as described above for the cyclization of the compounds of the formula XIII, to a compound of the formula XVI

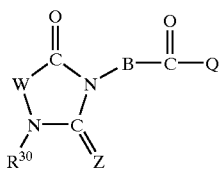

(XVI)

in which W is $R^1$—A—C($R^{13}$) and Z, B, Q and $R^{30}$ are defined as indicated above. Starting from the compound of the formula XVI, a compound of the formula Ia can then be obtained, for example, by hydrolysis of the group CO—Q to the carboxylic acid COOH and subsequent coupling to a compound of the formula III, as described above for the coupling of the compounds of the formulae II and III. In this synthesis process, too, functional groups can again be present in protected form or in the form of precursors.

A further method for the preparation of compounds of the formula Ia is, for example, the reaction of compounds of the formula XVII,

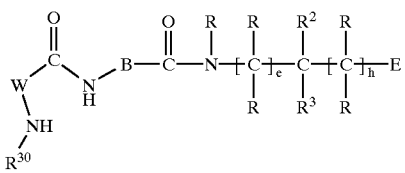

(XVII)

in which W is $R^1$—A—C($R^{13}$) and for which the definitions indicated above otherwise apply, with phosgene or thiophosgene or corresponding equivalents (analogously to S. Goldschmidt and M. Wick, Liebigs Ann. Chem. 575 (1952), 217–231 and C. Tropp, Chem. Ber. 61 (1928), 1431–1439).

Compounds of the formula Ia in which Z is oxygen can also be prepared by first coupling a compound of the formula XVIII

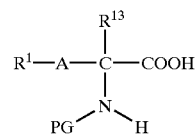

(XVIII)

in which $R^1$, $R^{13}$ and A have the meanings indicated above and PG is an amino protective group such as, for example, a benzyloxycarbonyl group, to a compound of the formula XIX,

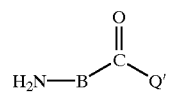

(XIX)

in which B has the meanings indicated above and Q' is a protected carboxylic acid hydroxyl group, for example an alkoxy group such as tert-butoxy, to give a compound of the formula XX

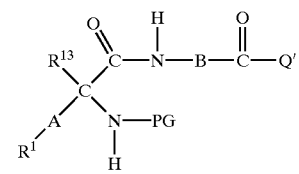

(XX)

in which $R^1$, $R^{13}$, A, B, PG and Q' have the meanings indicated above. In the compound of the formula XX, the protective group PG can then be selectively removed from the amino group, for example by hydrogenation in the case of a benzyloxycarbonyl group, and by introduction of a CO group a ring closure can be carried out to give a compound of the formula XXI

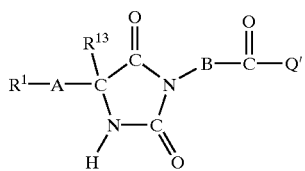

(XXI)

in which $R^1$, $R^{13}$, A, B and Q' have the meanings indicated above. For introduction of the carbonyl group, phosgene, for example, or a phosgene equivalent can be used (compare the reaction of the compounds of the formula XVII explained above). An intermediate which can occur or which can specifically be prepared in the conversion of the compound of the formula XX into that of the formula XXI is, for example, an isocyanate. The conversion of the compound of the formula XX into that of the formula XXI can be carried out in one or more steps. For example, the cyclization can be carried out separately in the presence of a base such as sodium hydride after introduction of the carbonyl group, like the cyclizations described above. Compounds of the formula XX in which PG is a benzyloxycarbonyl group can also be converted directly into compounds of the formula XXI without a buidling block such as phosgene being employed for the introduction of the carbonyl group. If compounds of the formula XX in which PG is benzyloxycarbonyl are treated with a base such as sodium hydride, the compounds of the formula XXI can be obtained directly.

In the compounds of the formula XXI, the radical $R^{30}$— or the radical PG—NR—$R^{31}$— can then be introduced onto the NH group as explained above for the compounds of the formula VI and, after cleavage of the protective group CO—Q' to the carboxylic acid group COOH as described above for the compounds of the formulae VII and II, the desired compound of the formula Ia (where Z=oxygen) can be synthesized. In this synthesis process, too, functional groups can again be present in protected form or in the form of precursors.

A guanidino group contained in the radical $R^1$ can be obtained, for example, from an amino group, which is in turn obtainable, for example, from a nitro group or a cyano group by reduction, using the following reagents:
1. O-Methylisourea (S. Weiss and H. Krommer, Chemiker-Zeitung 98 (1974), 617–618)
2. S-Methylisothiourea (R. F. Borne, M. L Forrester and I. W. Waters, J. Med. Chem. 20 (1977), 771–776)
3. Nitro-S-methylisothiourea (L. S. Hafner and R. E Evans, J. Org. Chem. 24(1959) 57)
4. Formamidinosulfonic acid (K. Kim, Y.-T. Lin and H. S. Mosher, Tetrah. Lett 29 (1988), 3183–3186)
5. 3,5-Dimethyl-1-pyrazolylformamidinium nitrate (F. L. Scott, D. G. O'Donovan and J. Reilly, J. Amer. Chem. Soc. 75(1953), 4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, Arzneim. Forsch./Drug Res. 34 (1984), 531–542).

Amidines can be prepared from the corresponding cyano compounds by addition of alcohols, for example methanol or ethanol, in acidic anhydrous medium, for example dioxane, methanol or ethanol, and subsequent aminolysis, for example treatment with ammonia in alcohols such as, for example, isopropanol, methanol or ethanol (G. Wagner, P. Richter and Ch. Garbe, Pharmazie 29 (1974), 12–55). A further method of preparing amidines is the addition of hydrogen sulfide to the cyano group, followed by a methylation of the resulting thioamide and subsequent reaction with ammonia (GDR Patent No. 235 866). Hydroxylamine can furthermore be added to the cyano group, N-hydroxyamidines being formed which, if desired, can likewise be converted into the amidines, for example by hydrogenation.

With respect to the preparation of the compounds of the formula I, the contents of WO-A-95/14008, EP-A-796 855 and the applications corresponding to it, as well as of WO-A-96/33976 are incorporated herein by reference in their entirety. For example, with respect to the preparation of the compounds of the formulae V and VI in racemic form and in enantiomerically pure form, reference is made to the corresponding details in WO-A-96/33976, which is also incorporated by reference in its entirety.

The compounds of the formula I are valuable pharmaceutical active compounds which are suitable, for example, for the therapy and prophylaxis of inflammatory disorders, allergic disorders or asthma. The compounds of the formula I and their physiologically tolerable salts and derivatives can be administered according to the invention to animals, preferably to mammals, and in particular to humans, as pharmaceuticals for therapy or prophylaxis. They can be administered per se, in mixtures with one another or in the form of pharmaceutical preparations which permit enteral or parenteral administration and which as active constituent contain an efficacious dose of at least one compound of the formula I and/or its physiologically tolerable salts and derivatives in addition to customary pharmaceutically innocuous excipients and/or additives.

The present invention therefore also relates to the compounds of the formula I and/or their physiologically tolerable salts and derivatives for use as pharmaceuticals, the use of the compounds of the formula I and/or their physiologically tolerable salts and derivatives for the production of pharmaceuticals for the therapy and prophylaxis of the diseases described above or below, for example for the therapy and prophylaxis of inflammatory disorders, and the use of the compounds of the formula I and/or their physiologically tolerable salts and derivatives in the therapy and prophylaxis of these diseases. The present invention furthermore relates to pharmaceutical preparations which contain an efficacious dose of at least one compound of the formula I and/or its physiologically tolerable salts and derivatives and a pharmaceutically innocuous carrier, i.e., customary pharmaceutically innocuous excipients and/or additives.

The pharmaceuticals can be administered systemically or locally. They can be administered, for example, in the form of pills, tablets, film-coated tablets, sugar-coated tablets, granules, hard and soft gelatin capsules, powders, solutions, syrups, emulsions, suspensions or in other pharmaceutical forms. However, administration can also be carried out vaginally or rectally, for example in the form of suppositories, or parenterally or by implantation, for example in the form of injection solutions or infusion solutions, microcapsules or rods, or topically or percutaneously, for example in the form of ointments, solutions or tinctures, or in another way, for example in the form of nasal sprays or aerosol mixtures. If solutions are parenterally administered they can be aministered, for example, intravenously, intramuscularly, subcutaneously, intraarticularly, intrasynovially or in another manner.

The pharmaceutical preparations according to the invention can be prepared in a manner known per se, it being possible to use pharmaceutically inert inorganic and/or organic excipients in addition to the compound(s) of the formula I and/or its/their physiologically tolerable salts and derivatives. For the preparation of pills, tablets, sugar-coated tablets and hard gelatin capsules, it is possible to use, for example, lactose, cornstarch or derivatives thereof, talc, stearic acid or its salts etc. Excipients for soft gelatin capsules and suppositories are, for example, fats, waxes, semisolid and liquid polyols, polyethylene glycols, natural or hardened oils etc. Suitable excipients for the preparation of solutions, for example injection solutions, or of emulsions or syrups are, for example, water, alcohols, glycerol, diols, polyols, sucrose, invert sugar, glucose, vegetable oils etc. Suitable excipients for microcapsules, implants or rods are, for example, copolymers of glycolic acid and lactic acid. The pharmaceutical preparations normally contain approximately 0.5 to 90% by weight of the compounds of the formula I and/or their physiologically tolerable salts and derivatives.

In addition to the active compounds and excipients, the pharmaceutical preparations can additionally contain auxiliaries or additives, such as, for example, fillers, disintegrants, binders, lubricants, wetting agents, stabilizers, emulsifiers, preservatives, sweeteners, colorants, flavorings or aromatizers, thickeners, diluents, buffer substances, solvents or solubilizers, means for achieving a depot effect, salts for altering the osmotic pressure, coating agents or antioxidants. They can also contain two or more compounds of the formula I and/or their physiologically tolerable salts and derivatives. Furthermore, they can also contain one or more other therapeutically or prophylactically active substances in addition to at least one compound of the formula I and/or its physiologically tolerable salts and derivatives, for example substances having antiinflammatory action. The pharmaceutical preparations normally contain 0.2 to 500 mg, preferably 1 to 100 mg, of active compound of the formula I and/or its physiologically tolerable salts and derivatives per dose.

If the compounds of the formula I or pharmaceutical preparations containing them are administered as aerosols, for example as nasal aerosols or by inhalation, this can be effected, for example, using a spray, an atomizer, a pump atomizer, an inhalation apparatus, a metered inhaler or a dry powder inhaler. Pharmaceutical forms for administration of the compounds of the formula I as an aerosol can be prepared by the process well known to the person skilled in the art For their preparation, for example, solutions or dispersions of the compounds of the formula I in water, water-alcohol mixtures or suitable saline solutions using customary additives, for example benzyl alcohol or other suitable preservatives, absorption enhancers for increasing the bioavailability, solubilizers, dispersants and others, and, if appropriate, customary propellants, for example chlorofluorohydrocarbons and/or fluorohydrocarbons are suitable.

The compounds of the formula I have the ability to inhibit cell-cell interaction processes and cell-matrix interaction processes in which interactions between VLA-4 with its ligands play a part The efficacy of the compounds of the formula I can be demonstrated, for example, in an assay in which the binding of cells which contain the VLA-4 receptor, for example of leucocytes, to ligands of this receptor is measured, for example to VCAM-1, which for this purpose can advantageously also be prepared by genetic engineering. Details of such an assay are described further below. In particular, the compounds of the formula I are able to inhibit the adhesion and the migration of leucocytes, for example the adhesion of leucocytes to endothelial cells which—as explained above—is controlled via the VCAM-1/VLA-4 adhesion mechanism. Besides as antiinflammatory agents, the compounds of the formula I and their physiologically tolerable salts and derivatives are therefore generally suitable for the therapy and prophylaxis of diseases which are based on the interaction between the VLA-4 receptor and its ligands or can be affected by an inhibition of this interaction, and in particular they are suitable for the therapy and prophylaxis of diseases which are caused at least partially by an undesired extent of leucocyte adhesion and/or leucocyte migration or are associated therewith, and for whose prevention, alleviation or cure the adhesion and/or migration of leucocytes should be decreased.

The present invention therefore also relates to the compounds of the formula I and their physiologically tolerable salts and derivatives for the inhibition of the adhesion and/or migration of leucocytes or for the inhibition of the VLA-4 receptor and the use of the compounds of the formula I for the production of pharmaceuticals for this purpose, i.e., of pharmaceuticals for the therapy or prophylaxis of diseases in which leucocyte adhesion and/or leucocyte migration exhibits an undesired extent, or for the therapy or prophylaxis of diseases in which VLA-4dependent adhesion processes play a part, and also the use of the compounds of the formula I and/or their physiologically tolerable salts and derivatives in the therapy and prophylaxis of diseases of this type.

The compounds of the formula I can be employed as antiinflammatories in the case of inflammatory symptoms of very different cause in order to prevent, to decrease or to suppress the undesired or harmful consequences of inflammation. They are used, for example, for the therapy or prophylaxis of arthritis, of rheumatoid arthritis, of polyarthritis, of inflammatory bowel disease (ulcerative colitis), of systemic lupus erythematosus, for the therapy or prophylaxis of inflammatory disorders of the central nervous system such as, for example, multiple sclerosis, or for the therapy or prophylaxis of asthma or of allergies, for example allergies of the delayed type (type IV allergy). They are furthermore suitable for the therapy or prophylaxis of cardiovascular disorders, arteriosclerosis, of restenoses, of diabetes, of damage to organ transplants, of immune disorders, of autoimmune disorders, of tumor growth or formation of tumor metastases in various malignancies, of malaria as well as of other diseases in which blocking of the integrin VLA-4 and/or influencing of the leucocyte activity appears appropriate for prevention, alleviation or cure.

The dose when using the compounds of the formula I can vary within wide limits, and as customary it is to be tailored to the individual conditions in each individual case, as is known to the physician. It depends, for example, on the nature and severity of the disease to be treated, on the compound employed or whether an acute or chronic disease state is treated or prophylaxis is conducted or on whether further active compounds are administered in addition to the compounds of the formula I. In general, in the case of oral administration, a daily dose of approximately 0.01 to 100 mg/kg, preferably 0.1 to 10 mg/kg, in particular 0.3 to 2 mg/kg (in each case per kg of body weight) is appropriate in an adult to achieve effective results. In the case of intravenous administration, the daily dose is in general approximately 0.01 to 50 mg/kg, preferably 0.01 to 10 mg/kg of body weight. In particular when relatively large amounts are administered, the daily dose can be divided into a number, for example 2, 3 or 4, of part administrations. If appropriate, depending on individual behavior, it may be necessary to deviate upward or downward from the indicated daily dose.

Apart from as pharmaceutical active compounds in human medicine and veterinary medicine, the compounds of the formula I and their salts and derivatives which are suitable for the use concerned, can furthermore be employed for diagnostic purposes, for example in in-vitro diagnoses of cell samples or tissue samples, and as auxiliaries or as a scientific tool in biochemical investigations in which VLA-4 blockage or an effect on cell-cell or cell-matrix interactions is intended. Furthermore, the compounds of the formula I and their salts can be used as intermediates for the preparation of other compounds, in particular of other pharmaceutical active compounds which are obtainable from compounds of the formula I, for example, by modification or introduction of radicals or functional groups, for example by esterification, reduction, oxidation or other conversions of functional groups.

The invention is illustrated by the following examples. The examples are for illustrative purposes only and do not limit the scope of the invention.

EXAMPLES

The products were identified by means of mass spectra (MS) and/or NMR spectra. Basic compounds which were purified by chromatography using an eluent which contained, for example, acetic acid or trifluoroacetic acid and were then freeze-dried, or which were treated with an acid, for example trifluoroacetic acid, and which for working up were freeze-dried, for example, sometimes still contained the acid used, depending on how the freeze drying or working up was carried out, and were thus obtained partially or completely in the form of a salt of the add used, for example in the form of the acetic acid salt or trifluoroacetic acid salt.

The abbreviations have the following meanings:

| | | | | | |
|---|---|---|---|---|---|
| MTBE | methyl tert-butyl ether | | | | |
| DMF | N,N-dimethylformamide | | | | |
| THF | tetrahydrofuran | | | | |
| DMAP | 4-dimethylaminopyridine | | | | |
| DCC | N,N'-dicyclohexylcarbodiimide | | | | |
| TOTU | O-((cyano(ethoxycarbonyl)methylene)amino)-N,N,N', N'-tetramethyluronium tetrafluoroborate | | | | |
| HOBT | 1-hydroxybenzotriazole | | | | |
| DIPEA | N,N-diisopropytethylamine | | | | |
| TFA | trifluoroacetic acid | | | | |
| DCM | dichloromethane | | | | |
| Me | methyl | $CH_3$— | Et | ethyl | $CH_3$—$CH_2$— |
| nPr | n-propyl | $CH_3CH_2CH_2$— | iPr | iso-propyl | $(CH_3)_2CH$— |
| nBu | n-butyl | $CH_3CH_2CH_2CH_2$— | iBu | iso-butyl | $(CH_3)_2CHCH_2$— |
| tBu | tert-butyl | $(CH_3)_3C$— | Ph | phenyl | $C_6H_5$— |
| Fmoc | 9-fluorenylmethoxycarbonyl | | | | |

The compounds of the examples were partly prepared according to the general procedures which are described below and are shown in the schemes. Radicals in the formulae in the schemes which have the same designations as the corresponding radicals in the formula I have the meanings indicated for the formula I. The meanings of other radicals are indicated in each case. The meaning of the radicals for a specific example substance and likewise the starting compounds which are to be employed in the individual steps of the synthesis of a specific example substance follow from the structure of the example substance.

A) General Procedure According to Scheme 1

To prepare the intermediate of the formula VIa. either an α-amino acid alkyl ester substituted in the α-position by the groups $R^{13}$ and $R^1$—A— was reacted with a tert-butyl isocyanatocarboxylate to give the urea and this was cyclized using sodium hydride (Steps A and B), or a hydantoin substituted in the 4-position by the groups $R^{13}$ and $R^1$—A— was alkylated with a tert-butyl bromocarboxylate (Step C). Either in situ or after prior isolation and, optionally, chromatographic purification the intermediate of the formula VIa was alkylated with 4-nitrobenzyl bromide to give the 3-(4-nitrobenzyl)hydantoin derivative (Step D). The nitro group was reduced by catalytic hydrogenation to the amino group (Step E), which was then reacted with an isocyanate of the formula $R^{32}$—N=C=O to give the urea (Step F). After conversion of the tert-butyl ester group into the carboxylic acid group using TFA (Step G), the intermediate of the formula IIa was coupled with an amino compound of the formula III in which carboxylic acid groups present were protected as esters (Step H). By removal of the ester protective groups, the compound of the formula I was finally obtained (Step J). Alk in Scheme 1 is methyl or ethyl. The individual steps were carried out as follows.

General Procedure for the Preparation of 3-(4-Nitrobenzyl)hydantoin Derivatives; Steps A, B, D (Method 1)

The α-amino acid alkyl ester was dissolved in DMF (about 2 ml per mmol of ester) and treated with 1 equivalent of the tert-butyl isocyanatocarboxylate (prepared analogously to J. S. Nowick et al., J. Org. Chem. 1996, 61, 3929). The mixture was stirred at room temperature for 12 hours. The solution of the resulting urea in DMF was employed in the further reaction without further purification and working up.

Scheme 1

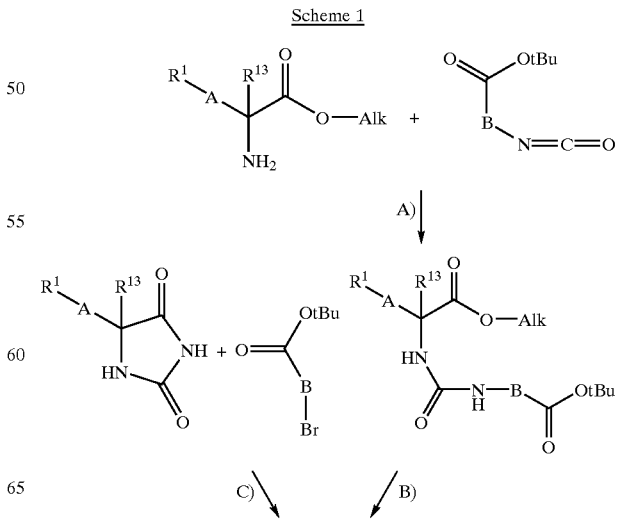

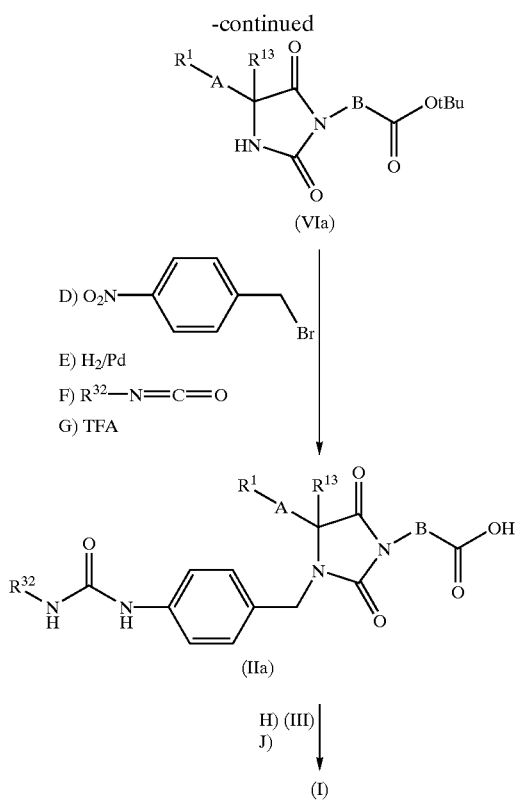

To cyclize the urea to the hydantoin, the urea solution was cooled to 0° C. and treated with 1.2 equivalents (based on the urea) of sodium hydride. The mixture was stirred at 0° C. for 15 minutes and then at room temperature for 2 hours. 1.1 equivalents (based on the urea) of 4-nitrobenzyl bromide were then added and the mixture was stirred at room temperature for 3 hours. If conversion was incomplete, a further 0.1 equivalent of sodium hydride was added and the mixture was stirred at room temperature for a further 3 hours. The reaction mixture was quenched by addition of water and the solvent was stripped off on a rotary evaporator. The oily residue was taken up in ethyl acetate and the solution was washed with water. The organic phase was dried over magnesium sulfate and the solvent was removed in vacuo. The residue was purified by flash chromatography (hexane/MTBE). The product fractions were combined.

General Procedure for the Preparation of 3-(4-Nitrobenzyl)hydantoin Derivatives; Steps A, B, D (Method 2)

Steps A and B were carried out as described above in the section Steps A, B, D (Method 1). In Method 2, before carrying out Step D, the intermediate of the formula VIa was first purified by chromatography on silica gel using heptane/MTBE. The product fractions were combined and the solvent was removed in vacuo. The residue was dissolved in DMF (2.5 ml per mmol of compound of the formula VIa), 1 equivalent of 4-nitrobenzyl bromide and 1.2 equivalents of cesium carbonate were added and the mixture was stirred at room temperature for about 5 hours and then allowed to stand at room temperature overnight. After filtration, the solvent was removed in vacuo and the residue was chromatographed on silica gel using heptane/MTBE. The product fractions were concentrated and employed in Step E.

General Procedure for the Preparation of 3-(4-nitrobenzyl)hydantoin Derivatives; Steps C, D (Method 1)

The hydantoin (16 mmol) was dissolved in DMF (about 7.5 ml per mmol of hydantoin) and treated with 1.2 equivalents of sodium hydride. The mixture was stirred at room temperature for 4 hours. After addition of 1.7 equivalents of the tert-butyl bromocarboxylate, stirring was continued overnight at room temperature. The solvent was removed on a rotary evaporator. The residue was purified by flash chromatography (heptane/MTBE). The alkylated hydantoin of the formula VIa was obtained.

The alkylated hydantoin of the formula VIa was dissolved in DMF (about 4 ml per mmol of hydantoin) and treated with 1.1 equivalents of sodium hydride. The mixture was stirred at room temperature for 1 hour. After addition of 1.1 equivalents of 4-nitrobenzyl bromide, the mixture was stirred at room temperature for a further 2–3 hours. The reaction mixture was quenched by addition of water and the solvent was stripped off on a rotary evaporator. The oily residue was taken up in ethyl acetate and washed with water. The organic phase was dried over magnesium sulfate and the solvent was removed in vacuo.

The residue was purified by flash chromatography (hexane/MTBE). The product fractions which contained the 3-(4-nitrobenzyl)hydantoin derivative were combined.

General Procedure for the Preparation of 3-(4-Nitrobenzyl)hydantoin Derivatives; Steps C, D (Method 2)

Step C was carried out as described above in the section Steps C, D (Method 1). In Method 2, in Step C, the intermediate of the formula VIa was reacted with 4-nitrobenzyl bromide and cesium carbonate (analogously to the process described above for Steps A, B, D (Method 2)) and the crude product obtained was purified by chromatography as described for Steps C, D (Method 1).

General Procedure for the Catalytic Reduction of the Nitro Compounds; Step E

The 3-(4-nitrobenzyl)hydantoin derivative was dissolved in methanol (about 10 ml per mmol of hydantoin derivative) and hydrogenated with palladium/carbon in a hydrogen atmosphere until reaction was complete. The catalyst was filtered off and the solvent was removed on a rotary evaporator. The 3-(4-aminobenzyl)hydantoin derivative was obtained.

General Procedure for the Preparation of the Ureas; Step F

The 3-(4-aminobenzyl)hydantoin derivative was dissolved in THF (about 4 ml per mmol of hydantoin derivative) and treated with 1 equivalent of the isocyanate of the formula $R^{32}$—N=C=O. The mixture was heated under reflux until reaction was complete. The solvent was removed in vacuo. The residue was purified by flash chromatography (hexane/MTBE). After concentrating the product fractions, the corresponding urea was obtained.

General Procedure for the Conversion of the tert-Butyl Esters into the Carboxylic Acids; Step G To cleave the tert-butyl ester group, the urea obtained in Step F was stirred at room temperature for 1 hour in TFA (about 10 ml per mmol). After removing the TFA on a rotary evaporator, the residue was freeze-dried. The carboxylic acid of the formula IIa was obtained.

General Procedure for Coupling the Carboxylic Acids to Amino Compounds; Step H (Method 1)

The carboxylic acid of the formula IIa was dissolved in DMF (about 5 ml per mmol of carboxylic acid) and treated with 1 equivalent of the amino compound to be coupled of the formula III, in which carboxylic acid groups that were present were protected as esters, and treated with 1 equivalent of HOBT. The mixture was cooled to 0° C., treated with 1 equivalent of DCC and stirred at 0° C. for 1 hour. It was then stirred at room temperature for 4 hours. The mixture was filtered and the solvent was removed in vacuo. Purification of the residue by flash chromatography afforded the coupling product.

General Procedure for Coupling the Carboxylic Acids to Amino Compounds; Step H (Method 2).

The carboxylic acid of the formula IIa and 1 equivalent of the amino compound to be coupled of the formula III were dissolved in DMF (about 5 ml per mmol of carboxylic acid). 1 equivalent of TOTU and 1 equivalent of DIPEA were added successively to the solution (if the amino compound of the formula III was employed as the hydrochloride, 2 equivalents of DIPEA were added). The mixture was stirred at room temperature. After reaction was complete, the solvent was removed in vacuo, the residue was taken up in ethyl acetate and the ethyl acetate phase was washed successively twice with saturated sodium hydrogencarbonate solution, potassium hydrogen sulfate/potassium sulfate solution and saturated sodium chloride solution. The phases were separated and the organic phase was dried over sodium sulfate. After filtration, the solvent was removed in vacuo and the residue was purified by chromatography on silica gel. In the cases in which the compound of the formula III contained one or more carboxylic acid group(s) protected as tert-butyl esters, methyl esters or ethyl esters, the ester was either first purified by chromatography on silica gel or the ester groups were first cleaved (see Step J) and the final product (the carboxylic acid) was then purified.

General Procedure for the Cleavage of tert-Butyl Ester Protective Groups: Step J (Method 1)

To cleave tert-butyl ester protective groups, the coupling product from Step H was dissolved in TFA (about 10 ml per mmol) and stirred at room temperature for 1 hour. The solvent was removed on a rotary evaporator. The residue was freeze-dried, in some cases after addition of acetic acid/water, or purified by chromatography and subsequently freeze-dried. The corresponding acid of the formula I was obtained.

General Procedure for the Cleavage of Methyl Ester and Ethyl Ester Protective Groups; Step J (Method 2)

To cleave methyl ester or ethyl ester protective groups, the coupling product from Step H was dissolved in methanol (about 15 ml per mmol) and the solution was treated with 3 equivalents of a 1N aqueous lithium hydroxide solution. The mixture was allowed to stand at room temperature overnight and then adjusted to a pH of 1 using 1N hydrochloric acid. Ethyl acetate was added, the phases were separated, the organic phase was washed with water and the solvent was removed in vacuo. The residue was freeze-dried after addition of acetic acid and water.

B) General Procedure According to Scheme 2

Scheme 2

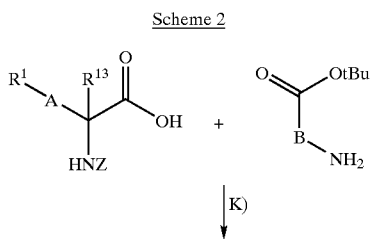

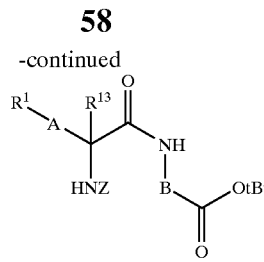

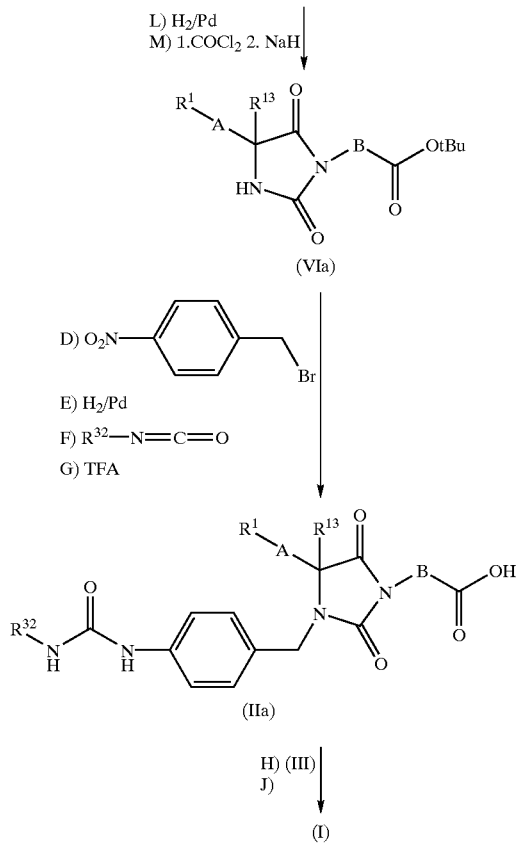

To prepare the intermediate of the formula VIa, an N-benzyloxycarbonyl-α-amino acid was coupled to an amino acid tert-butyl ester (Step K) and the coupling product was cyclized, after removal of the benzyloxycarbonyl group (=group Z) by catalytic hydrogenation (Step L) and introduction of a CO group on the free amino function obtained, to the compound of the formula VIa (Step M). This was alkylated to the 3-(4-nitrobenzyl)hydantoin derivative with 4-nitrobenzyl bromide analogously to the procedure according to Scheme 1, reacted to give the compound of the formula IIa, and the compound of the formula IIa was converted into the compound of the formula I by coupling with an amino compound of the formula III in which carboxylic acid groups were present in protected form as esters, and removal of the protective groups (Steps D–J). The individual steps were carried out as follows.

General Procedure for the Preparation of 3-(4-Nitrobenzyl)hydantoin Derivatives; Steps K, L, M, D In Step K, the N-benzyloxycarbonyl-α-amino acid and the amino acid tert-butyl ester were coupled as described for the procedure according to Scheme 1, Step H (Method 2). In Step L, the coupling product was hydrogenated on palladium/carbon as described for Scheme 1, Step E. In Step M, analogously to J. S. Nowick et al., J. Org. Chem. 1996, 61, 3929, the H$_2$N-group was then first converted into the isocyanate using phosgene in toluene. The isocyanate obtained was dissolved in DMF (2.5 ml per mmol of isocyanate). 1.2 equivalents of sodium hydride were added to the solution at 0° C. and the mixture was stirred at room temperature for 1.5 hours. The solvent was removed in vacuo, the residue was taken up in ethyl acetate and the mixture was washed twice with water. The phases were separated, the ethyl acetate phase was dried over sodium sulfate and, after filtration, the solvent was removed in vacuo. The compound of the formula VIa was obtained, which was reacted with 4-nitrobenzyl bromide in Step D either directly or after prior chromatographic purification according to the procedure described for Scheme 1, Steps C, D (Method 2). The following steps E, F and G, the coupling to the compound of the formula III carried out in Step H using TOTU and, if the coupling product from Step H contained ester protective groups, Step J were carried out analogously to the procedure according to Scheme 1, Steps E, F, G, H (Method 2) and J.

C) General Procedure According to Scheme 3

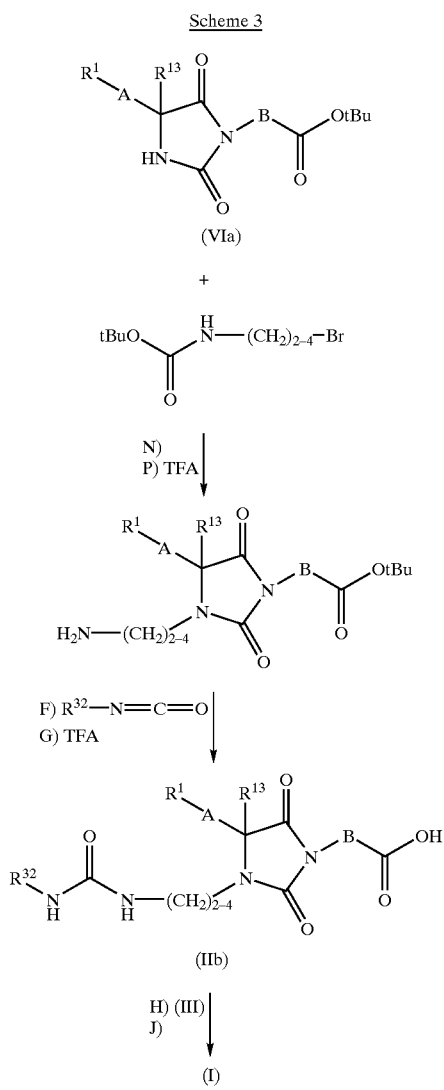

Starting from a compound of the formula VIa (preparation see above), by introduction of the N-Boc-protected aminoalkyl side chain (Step N) and subsequent selective cleavage of the N-Boc group (Step P) an aminoalkyl hydantoin derivative was prepared, which was then reacted to give the compound of the formula IIb analogously to the procedure according to Scheme 1 (Steps F, G). The compound of the formula IIb was then converted into the compound of the formula I by coupling with an amino compound of the formula III, in which carboxylic acid groups were present in protected form as esters, and removal of the protective groups (Steps H, J). The individual steps were carried out as follows.

General Procedure for the Preparation of 3-(4-aminoalkyl)hydantoin Derivatives; Steps N, P In Step N, the hydantoin derivative of the formula VIa was dissolved in DMF (about 3 ml per mmol of hydantoin derivative), the solution was treated with N-Boc-aminoalkyl bromide and 1.05 equivalents of cesium carbonate and the mixture was heated at 60° C. for 8–16 hours. The solvent was removed in vacuo and the residue was filtered through silica gel using heptane/MTBE. The product fractions were combined. After removing the solvent in vacuo. in Step P the residue was dissolved in a mixture of TFA/DCM (1:1)(about 8.5 ml per mmol) and poured into ice-cold sodium hydrogencarbonate solution (about 70 ml per mmol) after 4 minutes. The aqueous phase was extracted twice with DCM. The combined organic phases were dried over sodium sulfate. After filtration and removal of the solvent in vacuo, the 3-(aminoalkyl)hydantoin derivative was obtained.

The following Steps F, G and H (using TOTU) and, if the coupling product from Step H contained ester protective groups, Step J were carried out as described for Scheme 1, Steps F, G, H (Method 2) and J.

Racemic β-amino acids which were employed as amino compounds of the formula III in Step H in the procedures described above were prepared as described below for the procedure according to Scheme 5. Enantiomerically pure or highly enriched 3-substituted 3-aminopropionic acid esters were commercially available or were prepared analogously to S. G. Davis et al., Tetrahedron Asymmetry 1991, 2(3), 183–186. The procedure here was as follows.

General Procedure for the Preparation of 3-Substituted tert-Butyl 3-Aminopropionates The corresponding 3-substituted acrylic acid (0.1 mol) was dissolved in 100 ml of dichloromethane with 1.1 equivalents of oxalyl chloride. The mixture was stirred at room temperature for 4 hours. The solvent was removed on a rotary evaporator. The residue was taken up in 100 ml of tert-butanol and the mixture was stirred at room temperature for 2 hours. Alter reaction was complete, the solvent was removed on a rotary evaporator. The residue was dissolved in diethyl ether and washed with water, sodium hydrogencarbonate solution and again with water. The organic phase was dried over magnesium sulfate and the solvent was removed in vacuo. The 3-substituted tert-butyl acrylate was obtained in a yield of >80%.

To introduce the amino group, 0.95 equivalent of n-butyllithium (in n-hexane) was added dropwise to a solution of (R)—(+)-N-benzyl-N-(1-phenylethyl)amine (60 mmol) in 100 ml of THF at −70° C. over the period of 1 hour. The mixture was stirred at this temperature for 1 hour, then a solution of the 3-substituted tert-butyl acrylate (0.9 equivalents) in 75 ml of THF was added dropwise over the period of 1 hour. The mixture was stirred at −70° C. for 2 hours. After removing the cooling, 115 ml of 5% strength citric acid solution were added dropwise. The solution was stirred for 1 hour, treated with ethyl acetate and washed with water. The organic phase was washed with sodium hydrogencarbonate solution and water and dried over magnesium sulfate. The solvent was removed in vacuo. The residue was purified by flash chromatography (heptane/ethyl acetate, 9:1). The 3-substituted tert-butyl 3-(N-benzyl-N-(1-phenylethyl)amino)propionate was obtained in a yield of about 50% as a yellow oil. To remove the benzyl group and the phenylethyl group, the substance (about 30 mmol) was dissolved in 200 ml of a mixture of ethyl acetate and acetic acid (4:1) and treated with 1.5 g of palladium hydroxide. It was hydrogenated at room temperature for 8 hours under a hydrogen atmosphere. The catalyst was filtered off and the filtrate was concentrated on a rotary evaporator. The residue was taken up in ether/water. The aqueous phase was neutralized with sodium hydrogencarbonate and extracted several times with ether. The combined organic phases were dried over magnesium sulfate and carefully concentrated on a rotary evaporator. The 3-substituted tert-butyl 3-aminopropionate was obtained as a highly liquid, readily volatile oil in a yield of >50%.

Analogously to the reactions in solution described above, reactions for the preparation of the compounds of the formula I can also be carried out on solid phase, i.e. using resin-bound components. Individual synthesis steps or several synthesis steps can be carried out on the solid phase. In particular, couplings of compounds of the formulae IIa or IIb can also be carried out with resin-bound amino compounds of the formula III instead of with amino compounds of the formula III. Processes for the preparation of compounds of the formula I using solid-phase reactions are described below and shown in Schemes 4 and 5.

The quantitaties specified in the procedures for the solid-phase syntheses always relate to the respective resin loading which was determined by UV photometry after removal of the Fmoc protective group (see, for example "The Combinatorial Chemistry Catalog", Novabiochem).

D) General Procedure According to Scheme 4

Preparation of Compounds of the Formula I Which Contain an Aspartic Acid Unit by Solid-phase Synthesis For linkage to the polymeric support an orthogonally protected aspartic acid structural unit was employed. Fmoc-Asp(OH)-Oallyl was reacted with Wang polystyrene resin (Wang-PS) in the presence of a coupling reagent and the allyl ester protective group was then removed on the resin (Step Q). The free C terminus was then reacted with an amino acid tert-butyl ester (Step R) in the presence of a coupling reagent. After removal of the Fmoc protective group, the reaction at the N terminus was then carried out by coupling with a hydantoincarboxylic acid, which was prepared as described above (Step S). After removal of protective groups and removal from the resin, the compound of the formula I was obtained (Step T). Radicals in the formulae in Scheme 4, which have the same designations as the corresponding radicals in the formula I, have the meanings indicated for formula I. $R^{41}$, together with the CH group to which the radical $R^{41}$ is bonded and with the group COOtBu bonded to the CH group, corresponds to the group $R^4$ in the definition of the compounds of the formula I, which represents alkyl which is substituted by the substituents indicated in the definition of $R^4$. The individual steps were carried out as follows.

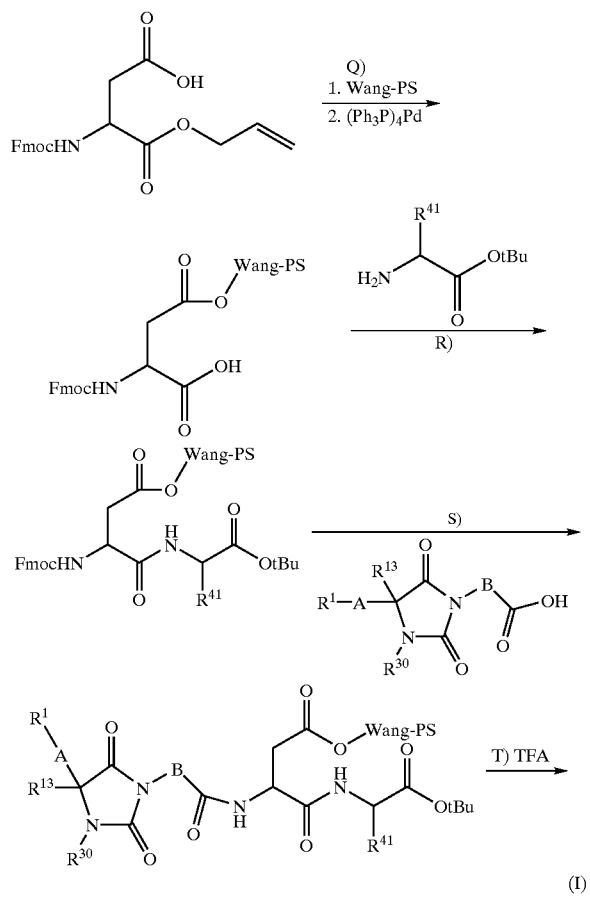

Scheme 4

Preparation of Fmoc-Asp(OH)-Oallyl 40 g (88.7 mmol) of Fmoc-Asp(OtBu)-Oallyl were treated with 25 ml of TFA and the mixture was stirred at room temperature for 30 minutes. The solvent was stripped off on a rotary evaporator. The residue was dried in vacuo. Fmoc-Asp(OH)-Oallyl was obtained as yellow oil in a yield of 33.9 g (97%). ES(+)-MS: 395.2 (M+H)⁺

Linkage to the polymeric support and removal of the allyl ester protective group on the polymeric support; Step Q 40 g of Wang polystyrene resin (1,1 mmol/g; Bachem) were preswollen at room temperature for 5 minutes with 20 ml of DMF. After addition of a solution of 26.0 g (1.5 equivalents) of Fmoc-Asp(OH)-Oallyl, 34.3 g (1.5 equivalents) of 1benzo-triazolyoxytripyrrolidinophosphonium hexafluorophosphate (PyBOP) and 1.5 equivalents of DIPEA in 120 ml of DMF, the mixture was shaken at 40° C. for 10 hours (TOTU/HOBT can also be employed as a coupling reagent with the same results). After reaction was complete, the solution was filtered off with suction and the resin was washed with DMF (5×20 ml). After addition of a solution of acetic anhydride (10 ml) and DIPEA (1.5 equivalents) in 40 ml of DMF, the mixture was again shaken at room temperature for 30 minutes. The solution was filtered off with suction and the resin was washed successively with 40 ml of DMF, methanol and DCM three times in each case. The resin was then dried in vacuo. Determination of the loading by the Fmoc method showed a loading of 0.6 mmol/g.

To remove the allyl ester protective group, the resin was preswollen in DMF at room temperature for 5 minutes under argon. After addition of tetrakis(triphenyl-phosphine)

palladium (0.1 equivalent) and N-methylaniline (10 equivalents), the mixture was shaken at 40° C. for 6 hours under argon. After reaction was complete, the solution was filtered off with suction and the resin was washed successively with DMF, methanol, toluene and DCM three times in each case and then dried.

General Procedure for Coupling to Amino Compounds on the Polymeric Support; Step R The resin having a free carboxyl function obtained in Step Q was preswollen at room temperature in DMF for 5 minutes. After addition of a solution of HOBT (1.2 equivalents), TOTU (1.2 equivalents) and DIPEA (1.2 equivalents) in DMF, the mixture was shaken at room temperature for 30 minutes. The amino compound (amino acid tert-butyl ester) (1.2 equivalents) was added as a solution in DMF. The suspension was shaken at room temperature until reaction was complete (HPLC checking). After reaction was complete, the solution was filtered off with suction and the resin was washed successively three times in each case with DMF, methanol, toluene and DCM and then dried.

General Procedure for Removal of the Fmoc Protective Group on the Polymeric Support and Coupling to Hydantoincarboxylic Acids; Step S 5 ml of a 20% strength solution of piperidine in DMF were added to 100 mg of the resin obtained in Step R and the mixture was shaken at room temperature for 20 minutes. The resin was filtered off with suction and the process was repeated a further time. The resin was then carefully washed several times with DMF and DCM. For the coupling, a solution of 2 equivalents each of HOBT, TOTU, DIPEA and the hydantoincarboxylic acid in DMF (10 ml/g of resin) was added to the resin and the mixture was shaken at room temperature for 12 hours. The resin was filtered off and washed three times with 10 ml each of DMF, once with 10 ml of toluene once with 10 ml of methanol and three times with 10 ml of DCM.

General Procedure for Removal From the Resin; Step T

A mixture of TFA and DCM (1:1) was added to the resin obtained in Step S. The suspension was shaken for 1 hour. The resin was filtered off and the solution was concentrated in vacuo. The residue was purified by chromatography on silica gel (DCM and ethyl acetate)

E) General Procedure According to Scheme 5

Preparation of Compounds of the Formula I Which Contain a β-amino Acid Unit by Solid-phase Synthesis The racemic β-amino acids employed were prepared from the corresponding aldehydes by reaction with malonic acid and ammonium acetate. After protection of the amino function by introduction of an Fmoc group, the acid was reacted with trityl chloride-polystyrene resin (PS-Trt-Cl) (Step U). According to Scheme 5, Variant A, the Fmoc protective group was then removed on the polymeric support, and then in the presence of a coupling reagent coupling to a hydantoincarboxylic acid which was prepared as described above was carried out (Step V). After removal from the resin, the compound of the formula I was obtained (Step W).

According to Scheme 5, Variant B, after removal of the Fmoc protective group, the compound was coupled on the polymeric support in the presence of a coupling reagent with a hydantoin building block which contained the group Fmoc-NH instead of the group $R^{32}$—NH—CO—NH contained in the compound of the formula IIa in Scheme 1 (Step Y). This hydantoin structural unit was prepared in solution by the procedure according to Scheme 1, where, after the hydrogenation in Step E, the aminobenzyl group obtained was converted into the N-Fmoc-aminobenzyl group. In the coupling product obtained on the polymeric support in Step Y, the Fmoc protective group was then removed. The free amino group obtained in the benzyl substituent on N-3 of the hydantoin was then reacted with isocyanates, isothiocyanates or carboxylic acids to give ureas, thioureas or amides, or it was reacted with a reactive carbonic acid derivative and alcohols or amines to give carbamic acid esters or ureas (Step Z). After removal from the resin, the compound of the formula I was finally obtained (Step W). The individual steps were carried out as follows.

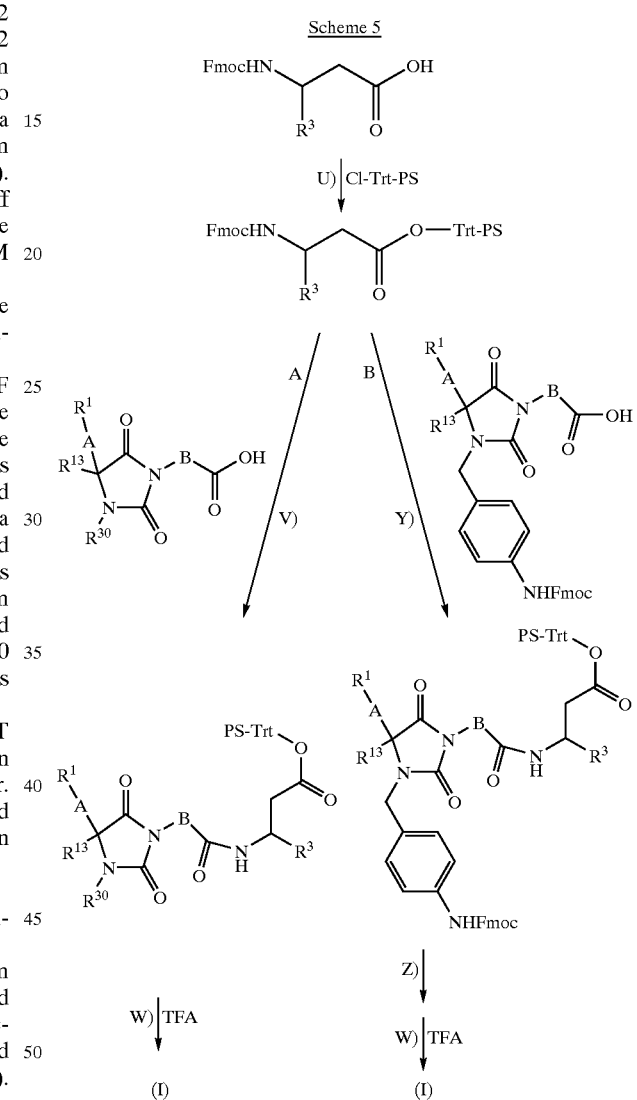

General Procedure for the Preparation of Racemic β-amino Acids of the Formula $H_2N$—$CH(R^3)$—$CH_2$—COOH 625 mg (6.0 mmol) of malonic acid, 789 mg (10.2 mmol) of ammonium acetate and 4.0 mmol of the respective aldehyde of the formula $R^3$—CHO were suspended in 10 ml of ethanol. The mixture was stirred at 90° C. for 6 hours. The precipitate was filtered off with suction and washed twice with 5 ml of ethanol each time.

General Procedure for the Introduction of the Fmoc Protective Group into β-amino Acids 4.0 mmol of the β-amino acid and 0.66 g (8.0 mmol) of sodium hydrogencarbonate were treated with 7 ml of water. A solution of 1.5 g (4.0 mmol) of N-(9-fluorenylmethoxycarbonyloxy)succinimide in 15 ml of dioxane was added by pipette and the mixture was stirred at room temperature for 6 hours. The mixture was then filtered and the residue was washed with 5 ml of ethyl acetate. The residue was taken up in 20 ml of 1N hydrochloric acid and extracted twice with 20 ml of ethyl acetate. The combined organic phases were dried over sodium sulfate, filtered and concentrated.

General Procedure for Coupling the N-Fmoc-β-amino Acids to the Polymeric Support; Step U The Fmoc-protected β-amino acids were suspended in 6 ml of DCM with trityl chloride-polystyrene resin and 0.5 ml of DIPEA. The mixture was shaken at room temperature for 6 hours. 1 ml of methanol was added to the mixture and it was shaken for a further 30 minutes at room temperature. The resin was filtered off with suction and washed carefully several times with DMF and DCM. Identity and purity of the compounds were checked by HPLC and MS. The determination of the loading according to the Fmoc method showed a loading of 0.2–0.3 mmol/g of support.

Variant A

General Procedure for Removal of the Fmoc Protective Group on the Polymeric Support and for Coupling to Hydantoincarboxylic Acids; Step V 5 ml of a 20% strength solution of piperidine in DMF were added to 100 mg of the resin obtained in Step U and the mixture was shaken at room temperature for 20 minutes. The resin was filtered off with suction and the process was repeated a further time. The resin was then carefully washed several times with DMF and DCM. A solution of 12.2 mg (0.09 mmol) of HOBT, 29.5 mg (0.09 mmol) of TOTU, 16 μl (0.09 mmol) of DIPEA and 0.09 mmol of the hydantoincarboxylic acid in 5 ml of DMF was then added to 100 mg of the resin which was loaded with the β-amino acid, and the mixture was shaken at room temperature for 12 hours. The resin was filtered off and washed three times with 10 ml each of DMF, once with 10 ml of toluene, once with 10 ml of methanol and three times with 10 ml of DCM.

General Procedure for Removal From the Polymeric Support; Step W

For the removal, the resin was suspended in 3 ml of TFA/DCM and shaken for 1 hour. The resin was filtered off and washed with 1 ml of DCM. The combined solutions were concentrated in a rotary evaporator. The residue was taken up in DCM and chromatographed on silica gel using DCM and ethyl acetate.

Variant B

General Procedure for Removal of the Fmoc Protective Group on the Polymeric Support and for Coupling to N-Fmoc-aminobenzylhydantoincarboxylic Acids; Step Y 5 ml of a 20% strength solution of piperidine in DMF were added to 100 mg of the resin obtained in Step U and the mixture was shaken at room temperature for 20 minutes. The resin was filtered off with suction and the process was repeated a further time. The resin was then washed carefully several times with DMF and DCM. A solution of 2 equivalents each of HOBT, TOTU. DIPEA and the N-Fmoc-aminobenzylhydantoincarboxylic acid in DMF (10 ml/g of resin) was then added to the resin obtained and the mixture was shaken at room temperature for 12 hours. The resin was filtered off and washed three times with 10 ml each of DMF, once with 10 ml of toluene, once with 10 ml of methanol and three times with 10 ml of DCM.

General Procedure for Removal of the Fmoc Protective Group on the Polymeric Support and for Derivatization of the Amino Group; Step Z 5 ml of a 20% strength solution of piperidine in DMF were added to 100 mg of the resin loaded with the N-Fmoc-aminobenzylhydantoincarboxylic acid and the mixture was shaken at room temperature for 20 minutes. The resin was filtered off with suction and the process was repeated a further time. The resin was then carefully washed several times with DMF and DCM. The free amino group obtained was then derivatized on the resin.

For the preparation of amides, the resulting free amino group was coupled with carboxylic acids. To do this, a solution of 0.027 mmol of HOBT, 0.027 mmol of TOTU, 0.027 mmol of DIPEA and 0.027 mmol of the carboxylic acid in 5 ml of DMF was added to 100 mg of the resin loaded with the aminobenzylhydantoin and the mixture was shaken at room temperature for 12 hours. The resin was filtered off and washed three times with 10 ml each of DMF, once with 10 ml of toluene, once with 10 ml of methanol and three times with 10 ml of DCM.

For the preparation of thioureas, the resulting free amino group was reacted with isothiocyanates. To do this, a solution of 0.027 mmol of the isothiocyanate and a catalytic amount of 1 mg of DMAP in 5 ml of DMF were added to 100 mg of the resin loaded with the aminobenzylhydantoin and the mixture was shaken at room temperature for 8 hours. The resin was filtered off and washed three times with 10 ml each of DMF, once with 10 ml of toluene, once with 10 ml of methanol and three times with 10 ml of DCM.

For the preparation of ureas, the resulting free amino group was reacted with isocyanates. To do this, a solution of 0.027 mmol of the isocyanate and a catalytic amount of 1 mg of DMAP in 5 ml of DMF were added to 100 mg of the resin loaded with the aminobenzylhydantoin and the mixture was shaken at room temperature for 8 hours. The resin was filtered off and washed three times with 10 ml each of DMF, once with 10 ml of toluene, once with 10 ml of methanol and three times with 10 ml of DCM.

For the preparation of N,N-disubstituted ureas, the resulting free amino group was first reacted with di(N-succinimidyl) carbonate and then with a secondary amine. To do this, a 10-fold excess of di(N-succinimidyl) carbonate and DIPEA were added to 100 mg of the resin loaded with the aminobenzylhydantoin and the mixture was shaken at 40° C. for 5 hours. The solution was filtered off with suction. A 10-fold excess of the amine in DMF was added to the resin. The mixture was shaken at room temperature for 8 hours. The resin was filtered off and washed three times with 10 ml each of DMF, once with 10 ml of toluene, once with 10 ml of methanol and three times with 10 ml of DCM.

For the preparation of carbamates, the corresponding alcohol was first reacted with di(N-succinimidyl) carbonate and the intermediate was then reacted with the resulting free amino group. To do this, the alcohols (0.027 mmol) were shaken at 40° C. for 5 hours with equivalent amounts of each of di(N-succinimidyl) carbonate and DIPEA. The solution was added to 100 mg of the resin loaded with the aminobenzylhydantoin and the mixture was shaken at room temperature for 8 hours. The resin was filtered off and washed three times with 10 ml each of DMF, once with 10 ml of toluene, once with 10 ml of methanol and three times with 10 ml of DCM.

The removal from the polymeric support (Step W) in Variant B was carried out as in Variant A.

F) General Procedure for the Preparation of Compounds of the Formula I Which Contain a Peptide Unit, by Solid-phase Synthesis Compounds of the formula I which contain a peptide unit can be prepared by first linking the C-terminal N-Fmoc-α-amino acid to the polymeric support and removing the Fmoc protective group. The liberated amino function is then coupled to a further N-Fmoc-amino acid and the Fmoc protective group is removed. This linkage of further amino acid units is repeated until the desired peptide unit has been synthesized. Finally, using a coupling reagent, a hydantoincarboxylic acid is linked, the product is removed from the resin and protective groups which may be present are removed. The individual steps are carried out as follows.

General Procedure for Coupling N-Fmoc-α-amino Acids to the Polymeric Support

The Fmoc-protected α-amino acid (1.5 equivalents) is suspended in DCM (5 ml/g of support) with trityl chloride polystyrene resin (1.2 mmol/g) and DIPEA (2 equivalents). The mixture is shaken at room temperature for 6 hours. 1 ml of methanol is added to the mixture and it is shaken at room temperature for a further 30 minutes. The resin is filtered off with suction and carefully washed several times with DMF and DCM. Identity and purity of the compounds are checked by HPLC and MS.

General Procedure for Removal of the Fmoc Protective Group on the Polymeric Support 5 ml of a 20% strength solution of piperidine in DMF are added to 100 mg of the resin loaded with the N-Fmoc-α-amino acid and the mixture is shaken at room temperature for 20 minutes. The resin is filtered off with suction and the process is repeated a further time. The resin is then carefully washed several times with DMF and DCM.

General Procedure for Coupling the β-amino Acids to the Polymeric Support with N-Fmoc-α-amino Acids A solution of 12.2 mg (0.09 mmol) of HOBT, 29.5 mg (0.09 mmol) of TOTU, 16 μl (0.09 mmol) of DIPEA and 0.09 mmol of the N-Fmoc-α-amino acid in 5 ml of DMF is added to 100 mg of the resin loaded with the α-amino acid and the mixture is shaken at room temperature for 12 hours. The resin is filtered off and washed three times with 10 ml each of DMF, once with 10 ml of toluene, once with 10 ml of methanol and three times with 10 ml of DCM.

To introduce further amino acids into the peptide unit the two above steps (removal of the Fmoc protective group and coupling to a further N-Fmoc-α-amino add) are correspondingly repeated.

General Procedure for Removal of the Fmoc Protective Group on the Polymeric Support and for Coupling the Peptide Unit to the Polymeric Support With Hydantoincarboxylic Acids The Fmoc group of the peptide unit synthesized on the resin is removed as described above. A solution of 12.2 mg (0.09 mmol) of HOBT, 29.5 mg (0.09 mmol) of TOTU, 16 μl (0.09 mmol) of DIPEA and 0.09 mmol of the hydantoincarboxylic acid in 5 ml of DMF is then added to 100 mg of the resin loaded with the peptide unit and the mixture is shaken at room temperature for 12 hours. The resin is filtered off and washed three times with 10 ml each of DMF, once with 10 ml of toluene, once with 10 ml of methanol and three times with 10 ml of DCM.

General Procedure for Removal From the Resin

To remove the compound from the resin, a mixture of TFA and DCM (1:9) is added to the resin. The suspension is shaken for 1 hour. The resin is filtered off. The solution which remains is concentrated in vacuo and the residue is purified by silica gel chromatography.

G) General Procedure for the Preparation of Unsubstituted Carboxamides on the Solid Phase For the conversion of compounds of the formula I which contain a carboxylic acid group —COOH into the corresponding compounds having an unsubstituted carboxamide group —CONH$_2$, the carboxylic acid group was linked to Rink amide resin using a coupling reagent. The linkage to the amino function in the resin was carried out analogously to the procedure for the linkage of carboxylic acids to Wang resin (see process according to Scheme 4). Removal with TFA then afforded the unsubstituted amides.

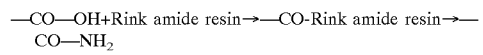

In detail, 0.5 g of the carboxylic acid of the formula I was reacted with 0.35 g of TOTU, 0.15 ml of DIPEA and 2 g of Rink amide resin in 10 ml of DMF. The suspension was shaken at room temperature for 1 hour. The resin was filtered off with suction and carefully washed with DMF and DCM. The removal was then performed using 5 ml of TFA/DCM (1:1). After removing the solvent, the residue was purified.

EXAMPLE 1

((RS)-2-((RS)-4-Phenyl-3-(4-(3-phenylureido) benzyl)-4-methyl-2,5-dioxoimidazolidin-1-yl)-2-(2-methylpropyl)acetyl)-L-aspartyl-L-phenylglycine

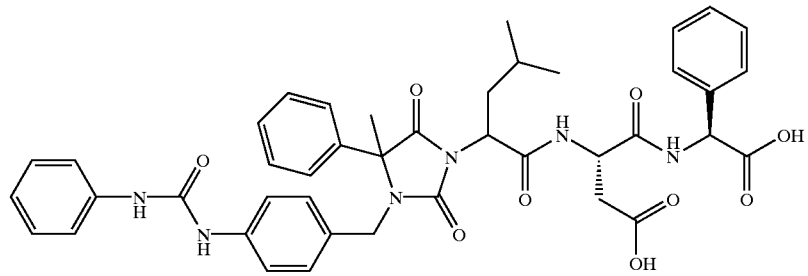

The compound was prepared by the process according to Scheme 1, Steps C, D (Method 1) E, F, G, H (Method 1), J (Method 1). In Step H (batch size 0.3 mmol), the amino compound of the formula III employed was H-Asp(OtBu)-Phg-OtBu (hydrochloride; Asp=aspartyl, Phg=phenylglycyl). Yield: 52 mg.

ES(+)-MS: 777.9 (M+H)⁺

EXAMPLE 2

((RS)-2-((RS)-4-Phenyl-3-(4-(3-(2-methylphenyl)ureido)benzyl)-4-methyl-2,5-dioxoimidazolidin-1-yl)-2-(2-methylpropyl)acetyl)-L-aspartyl-L-phenylglycine

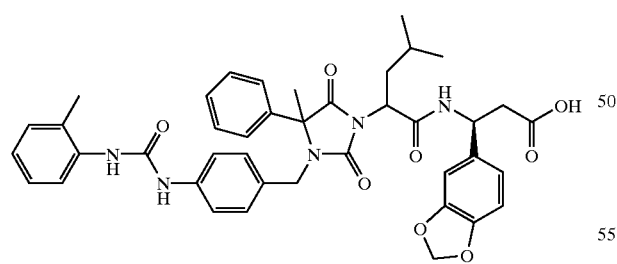

The compound was prepared by the process according to Scheme 1, Steps C, D (Method 1), E, F, G, H (Method 1). J (Method 1). In Step H (batch size 0.184 mmol), the amino compound of the formula III employed was H-Asp(OtBu)-Phg-OtBu (hydrochloride). Yield: 59 mg.

ES(+)-MS: 791.9 (M+H)⁺

EXAMPLE 3

(S)-3-((RS)-2-((RS)-4-Phenyl-3-(4-(3-(2-methylphenyl)ureido)benzyl)-4-methyl-2,5-dioxoimidazolidin-1-yl)-2-(2-methylpropyl)acetylamino)-3-(3,4-methylenedioxy-phenyl)propionic Acid

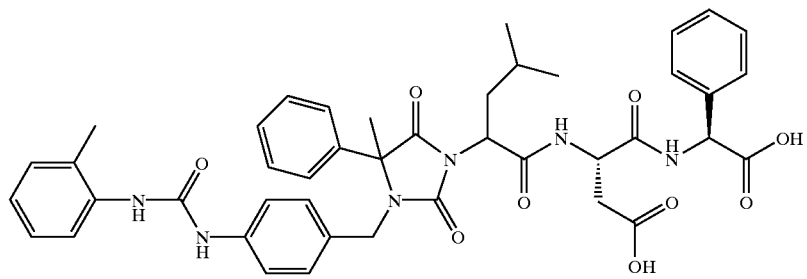

The compound was prepared by the process according to Scheme 1, Steps C, D (Method 1), E, F, G, H (Method 1), J (Method 1). In Step H (batch size 0.184 mmol), the amino compound of the formula III employed was tert-butyl (S)-3-amino-3-(3,4-methylenedioxyphenyl)propionate. Yield: 92 mg.

ES(+)-MS: 734.9 (M+H)⁺

EXAMPLE 4

(R)-3-((RS)-2-((RS)-4-Phenyl-3-(4-(3-(2-methylphenyl)ureido)benzyl)-4-methyl-2,5-dioxoimidazolidin-1-yl)-2-(2-methylpropyl)acetylamino)-3-methylpropionic Acid

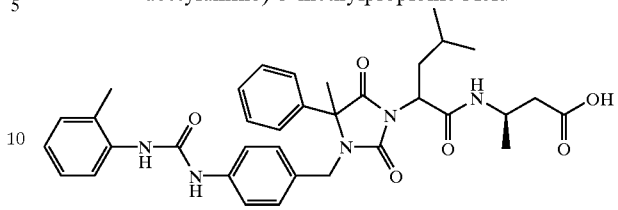
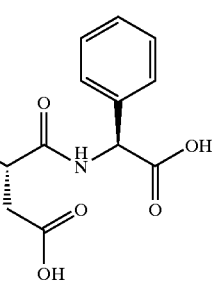

The compound was prepared by the process according to Scheme 1, Steps C, D (Method 1), E, F, G, H (Method 1), J (Method 1). In Step H (batch size 0.184 mmol), the amino compound of the formula III employed was tert-butyl (R)-3-amino-3-methyl-propionate. Yield: 109 mg.

ES(+)-MS: 628.4 (M+H)⁺

EXAMPLE 5

(S)-3-((S)-2-(4,4-Dimethyl-3-(4-(3-phenylureido)benzyl)-2,5-dioxoimidazolidin-1-yl)-2-(2-methylpropyl)acetylamino)-3-(3,4-methylenedioxyphenyl)propionic Acid

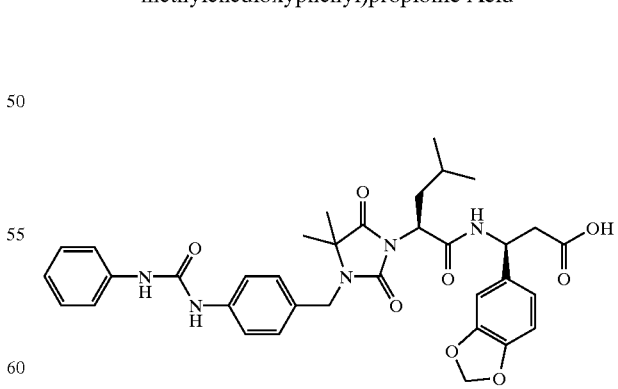

The compound was prepared by the process according to Scheme 1, Steps A, B, D (Method 1), E, F, G, H (Method 1), J (Method 1). In Step H (batch size 2.6 mmol), the amino compound of the formula III employed was tert-butyl (S)-3amino-3-(3,4-methylenedioxyphenyl)propionate. Yield: 284 mg.

ES(+)-MS: 658.7 (M+H)+

(R)-3-((S)-2-(4,4-Dimethyl-3-(4-(3-phenylureido)benzyl)2,5-dioxoimidazolidin-1-yl)-2-(2-methylpropyl)acetylamino)-3-methylpropionic Acid

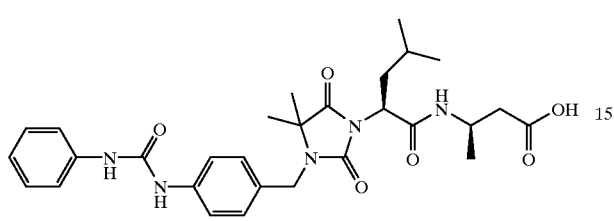

The compound was prepared by the process according to Scheme 1, Steps A, B, D (Method 1), E, F, G, H (Method 1), J (Method 1). In Step H (batch size 2.6 mmol), the amino compound of the formula III employed was tert-butyl (R)-3-amino-3-methylpropionate. Yield: 451 mg.

ES(+)-MS: 552.6 (M+H)+

The compound of Example 6 was also prepared by the process according to Scheme 1 Steps A, B, D (Method 2), E, F, G, H (Method 1), J (Method 1).

The compound of Example 6 was also prepared by the process according to Scheme 2.

EXAMPLE 7

(S)-3-((S)-2-(4,4-Dimethyl-3-(4-(3-(2-methylphenyl)ureido)benzyl)-2,5-dioxoimidazolidin-1-yl)-(2-methylpropyl)acetylamino)-3-(3,4-methylenedioxyphenyl)propionic Acid

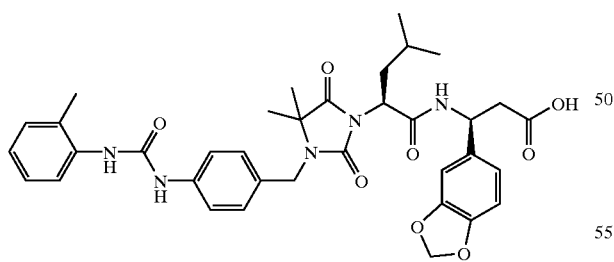

The compound was prepared by the process according to Scheme 1, Steps A, B, D (Method 1), E, F, G, H (Method 1), J (Method 1). In Step H (batch size 2.3 mmol), the amino compound of the formula III employed was tert-butyl (S)-3-amino-3-(3,4-methylenedioxyphenyl)propionate. Yield: 453 mg.

ES(+)-MS: 672.7 (M+H)+

EXAMPLE 8

(R)-3-((S)-2-(4,4-Dimethyl-3-(4-(3-(2-methylphenyl)ureido)benzyl)-2,5-dioxoimidazolidin-1-yl)-2-(2-methylpropyl)acetylamino)-3-methylpropionic Acid

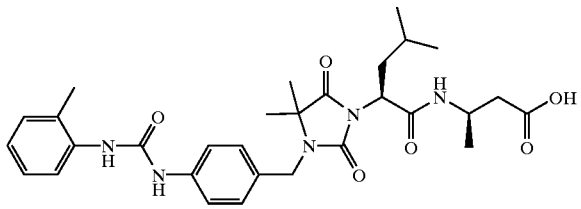

The compound was prepared by the process according to Scheme 1, Steps A, B, D (Method 1), E, F, G, H (Method 1), J (Method 1). In Step H (batch size 2.3 mmol), the amino compound of the formula III employed was tert-butyl (R)-3-amino-3-methylpropionate. Yield: 420 mg.

ES(+)-MS: 566.7 (M+H)+

EXAMPLE 9

(R)-3-(2-(4,4-Dimethyl-3-(4-(3-(2-methylphenyl)ureido)benzyl)-2,5-dioxoimidazolidin-1-yl)acetylamino)-3-methylpropionic Acid

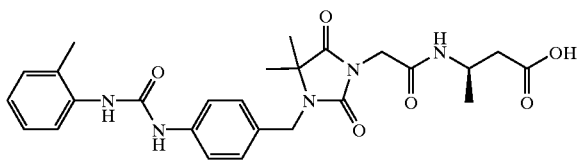

The compound was prepared by the process according to Scheme 1, Steps C, D (Method 1), E, F, G, H (Method 2), J (Method 1). In Step H (batch size 1.5 mmol), the amino compound of the formula III employed was tert-butyl (R)-3-amino-3-methyl-propionate. Yield: 440 mg.

ES(+)-MS: 510.6 (M+H)+

EXAMPLE 10

2-((S)-2-(4,4-Dimethyl-3-(4-(3-(2-methylphenyl)ureido)benzyl)-2,5-dioxoimidazolidin-1-yl)-2-(2-methylpropyl)acetylamino)acetic Acid

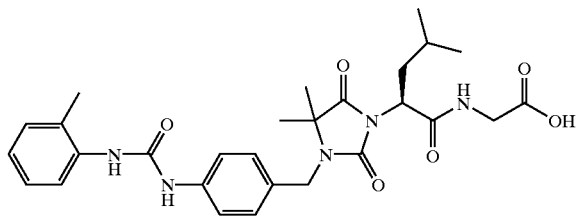

The compound was prepared by the process according to Scheme 1, Steps A, B, D (Method 1), E, F, G, H (Method 2), J (Method 2). In Step H (batch size 0.21 mmol), the amino compound of the formula III employed was glycine methyl ester. Yield: 26 mg. ES(+)-MS: 538.4 (M+H)+

EXAMPLE 11

(S)-3-(2-(4,4-Dimethyl-3-(4-(3-(2-methylphenyl)ureido)benzyl)2,5-dioxoimidazolidin-1-yl)acetylamino)-3-phenylpropionic Acid

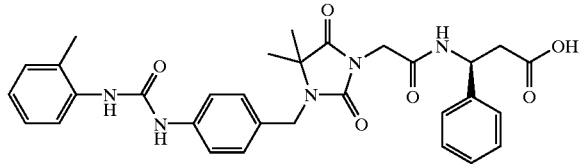

The compound was prepared by the process according to Scheme 1, Steps C, D (Method 1), E, F, G, H (Method 2), J (Method 2). In Step H (batch size 1.41 mmol), the amino compound of the formula III employed was ethyl (S)-3-amino-3-phenylpropionate. Yield: 534 mg.

ES(+)-MS: 572.4 (M+H)$^+$

The compound of Example 11 was also prepared by the process according to Scheme 1, Steps C, D (Method 2), E, F, G, H (Method 2), J (Method 2).

EXAMPLE 12

(R)-3-((S)-2-(4,4-Dimethyl-3-(2-(3-(2-methylphenyl)ureido)ethyl)-2,5-dioxoimidazolidin-1-yl)-2-(2-methylpropyl)acetylamino)-3-methylpropionic Acid

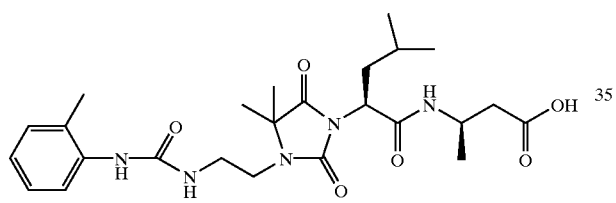

The compound was prepared by the process according to Scheme 3 (Step J according to Method 1). The preparation of the compound of the formula VIa was carried out according to Scheme 1, Steps A, B. In Step H (batch size 0.19 mmol), the amino compound of the formula III employed was tert-butyl (R)-3-amino-3-methylpropionate. Yield: 58 mg.

ES(+)-MS: 504.4 (M+H)$^+$

EXAMPLE 13

(R)-3-((S)-2-(4,4-Dimethyl-3-(3-(3-(2-methylphenyl)ureido)propyl)-2,5-dioxoimidazolidin-1-yl)-2-(2-methylpropyl)acetylamino)-3-methylpropionic Acid

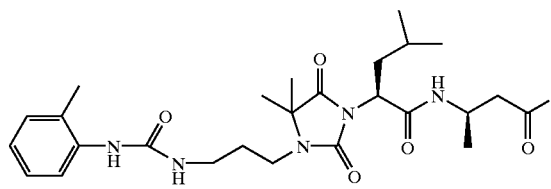

The compound was prepared by the process according to Scheme 3 (Step J according to Method 1). The preparation of the compound of the formula VIa was carried out according to Scheme 1, Steps A, B. In Step H (batch size 0.25 mmol), the amino compound of the formula III employed was tert-butyl (R)-3-amino-3-methylpropionate. Yield: 54 mg.

ES(+)-MS: 518.4 (M+H)$^+$

EXAMPLE 14

(R)3-(2-(4,4-Dimethyl-3-(4-(3-(2-fluorophenyl)ureido)benzyl)-2,5-diaxoimidazolidin-1-yl)acetylamino)-3-methylpropionic Acid

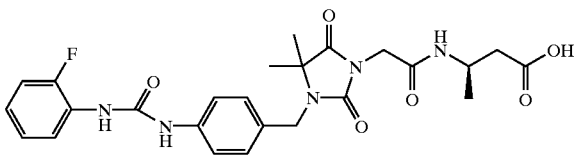

The compound was prepared by the process according to Scheme 1, Steps C, D (Method 1), E, F, G, H (Method 2), J (Method 1). In Step H (batch size 1.94 mmol), the amino compound of the formula III employed was tert-butyl (R)-3-amino-3-methypropionate. Yield: 414 mg.

ES(+)-MS: 514.3 (M+H)$^+$

EXAMPLE 15

3-(2-(4,4-Dimethyl-3-(4-(3-(2-methylphenyl)ureido)benzyl)-2,5-dioxoimidazolidin-1-yl)acetylamino)propionic Acid

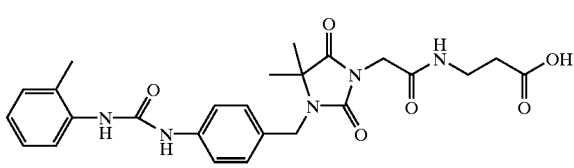

The compound was prepared by the process according to Scheme 1, Steps C, D (Method 1), E, F, G, H (Method 2), J (Method 2). In Step H (batch size 0.47 mmol), the amino compound of the formula III employed was methyl 3-aminopropionate. Yield: 136 mg.

ES(+)-MS: 496.2 (M+H)$^+$

EXAMPLE 16

3-((S)-2-(4,4-Dimethyl-3-(4-(3-(2-methylphenyl)ureido)benzyl)-2,5-dioxoimidazolidin-1-yl)-2-(2-methylpropyl)acetylamino)propionic Acid

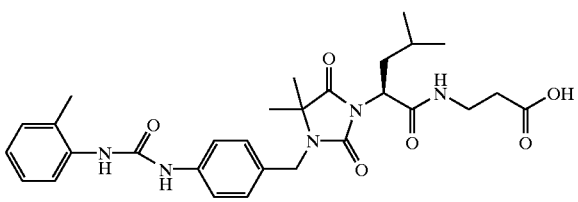

The compound was prepared by the process according to Scheme 1, Steps A, B, D (Method 1), E, F, G, H (Method 1), J (Method 2). In Step H (batch size 0.21 mmol), the amino compound of the formula III employed was methyl 3-aminopropionate. Yield: 23 mg.

ES(+)-MS: 552.3 (M+H)$^+$

EXAMPLE 17

(S)-3-((S)-2-(4,4-Dimethyl-3-(4-(3-(2-methylphenyl)ureido)benzyl)-2,5-dioxoimidazolidin-1-yl)-2-(2-methylpropyl)acetylamino)-3-phenylpropionic Acid

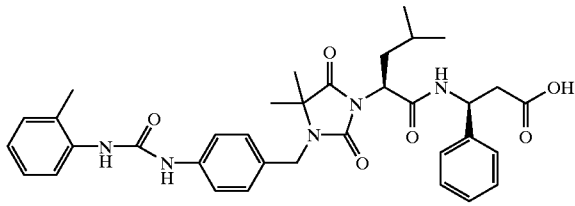

The compound was prepared by the process according to Scheme 1, Steps A, B, D (Method 1), E, F, G, H (Method 2), J (Method 2). In Step H (batch size 0.208 mmol), the amino compound of the formula III employed was ethyl (S)-3-amino-3-phenylpropionate. Yield: 66 mg.

ES(+)-MS: 628.4 (M+H)$^+$

EXAMPLE 18

3-(2-(4,4-Dimethyl-3-(4-(3-(2-fluorophenyl)ureido)benzyl)-2,5-dioxoimidazolidin-1-yl)acetylamino)propionic Acid

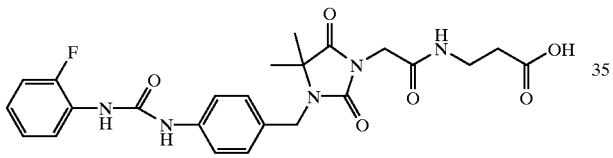

The compound was prepared by the process according to Scheme 1, Steps C, D (Method 1), E, F, G, H (Method 2), J (Method 2). In Step H (batch size 1.94 mmol), the amino compound of the formula III employed was ethyl 3-aminopropionate hydrochloride. Yield: 368 mg.

ES(+)-MS: 500.2 (M+H)$^+$

EXAMPLE 19

(S)-3-((S)-2-(4,4-Dimethyl-3-(4-(3-phenyl)ureido)benzyl)-2,5-dioxoimidazolidin-1-yl)-2-(2-methylpropyl)acetylamino)-3-phenylpropionic Acid

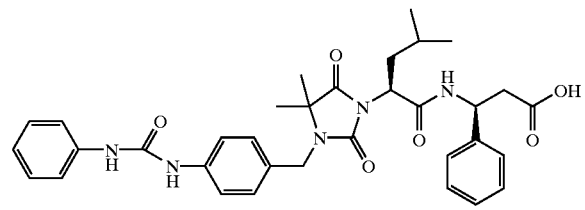

The compound was prepared by the process according to Scheme 1, Steps A, B, D (Method 1), E, F, G, H (Method 2), J (Method 2). In Step H (batch size 4.11 mmol), the amino compound of the formula III employed was ethyl (S)-3-amino-3-phenylpropionate. Yield: 1 g.

ES(+)-MS: 614.3 (M+H)$^+$

EXAMPLE 20

(2-(3-(4-(3-(2-Methylphenyl(ureido)benzyl)-2,5-dioxoimidazolidin-1-yl)acetyl)-N-methyl-L-(2-adamantyl)aspartamide

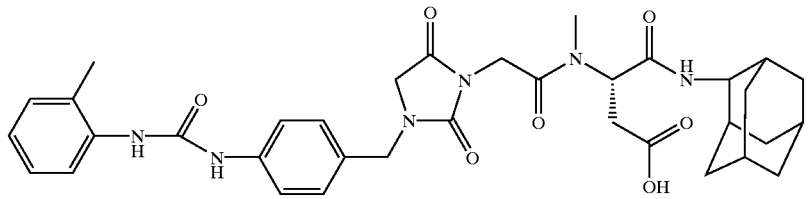

The compound was prepared by the process according to Scheme 1, Steps C, D (Method 1), E, F, G, H (Method 2), J (Method 1). In Step H (batch size 1.26 mmol), the amino compound of the formula III employed was tert-butyl N-methyl-L-(2-adamantyl)aspartamidate hydrochloride. Yield: 617 mg.

ES(+)-MS: 659.4 (M+H)⁺

EXAMPLE 21

(2-(3-(4-(3-(2-Methylphenyl)ureido)benzyl)-2,5-dioxoimidazolidin-1-yl)acetyl)-L-2-adamantyl)aspartamide

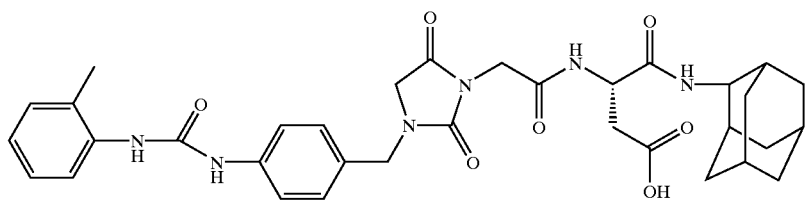

The compound was prepared by the process according to Scheme 1, Steps C, D (Method 1), E, F, G, H (Method 2), J (Method 1). In Step H (batch size 0.882 mmol), the amino compound of the formula III employed was tert-butyl L-(2-adamantyl)aspartamidate. Yield: 470 mg.

ES(+)-MS: 645.4 (M+H)⁺

EXAMPLE 22

(2-(4,4-Dimethyl-3-(4-(3-(2-methylphenyl)ureido)benzyl)-2,5-dioxoimidazolidin-1-yl)-acetyl)-N-methyl-L-(2-adamantyl)aspartamide

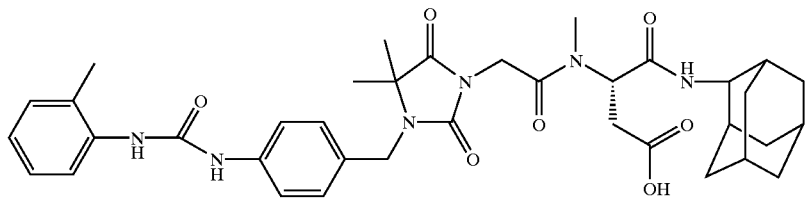

The compound was prepared by the process according to Scheme 1, Steps C, D (Method 1), E, F, G, H (Method 2), J (Method 1). In Step H (batch size 0.942 mmol), the amino compound of the formula III employed was tert-butyl N-methyl-L-(2-adamantyl)aspartamidate hydrochloride. Yield: 535 mg.

ES(+)-MS: 687.4 (M+H)⁺

EXAMPLE 23

(2-(4,4-Dimethyl-3-(4-(3-phenyl)ureido)benzyl)-2,5-dioxoimidazolidin-1-yl)-acetyl)-N-methyl-L-(2-adamantyl)aspartamide

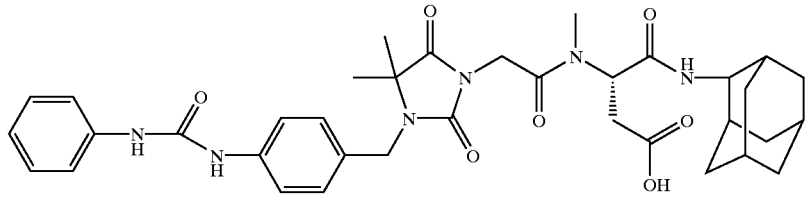

The compound was prepared by the process according to Scheme 1, Steps C, D (Method 1), E, F, G, H (Method 2), J (Method 1). In Step H (batch size 1.41 mmol), the amino compound of the formula III employed was tert-butyl N-methyl-L-2-adamantyl)aspartamidate hydrochloride. Yield: 599 mg.

ES(+)-MS: 673.4 (M+H)$^+$

EXAMPLE 24

(2-(4,4-Dimethyl-3-(4-(3-phenylureido)benzyl)-2,5-dioxoimidazolidin-1-yl)-acetyl)-L-(2-adamantyl)aspartamide

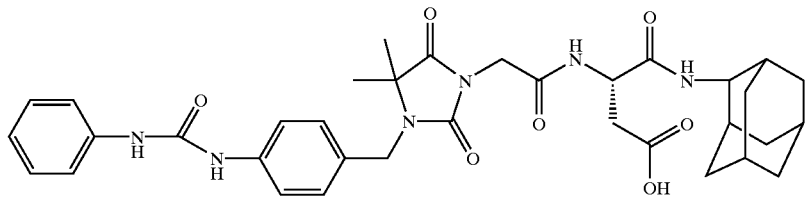

The compound was prepared by the process according to Scheme 1, Steps C, D (Method 1), E, F, G, H (Method 2), J (Method 1). In Step H (batch size 0.974 mmol), the amino compound of the formula III employed was tert-butyl L-(2-adamantyl)aspartamidate. Yield: 410mg.

ES(+)-MS: 659.4 (M+H)$^+$

EXAMPLE 25

((S)-2-(4,4-Dimethyl-3-(4-(3-phenylureido)benzyl)-2,5-dioxoimidazolidin-1-yl)-2-L-(2-adamantyl)aspartamide

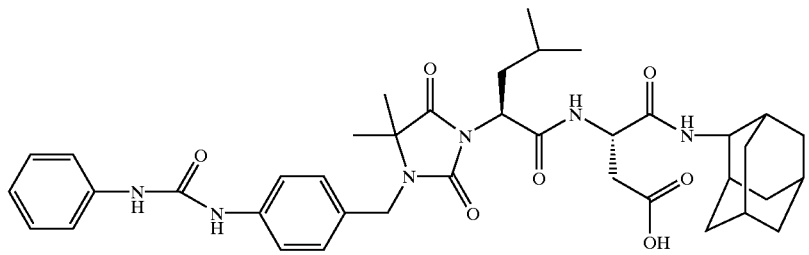

The compound was prepared by the process according to Scheme 1, Steps A, B, D (Method 1), E, F, G, H (Method 2), J (Method 1). In Step H (batch size 1.28 mmol), the amino compound of the formula III employed was tert-butyl L-(2-adamantyl)-aspartamidate. Yield: 576 mg.

ES(+)-MS: 715.5 (M+H)+

EXAMPLE 26

(R)-3-(2-(3-(4-(3-(2-Methylphenyl)ureido)benzyl)-2,5-dioxoimidazolidin-1-yl)-acetylamino)-3-methylpropionic Acid

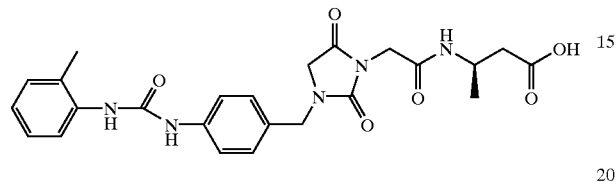

The compound was prepared by the process according to Scheme 1, Steps C, D (Method 1), E, F, G, H (Method 2), J (Method 1). In Step H (batch size 1.5 mmol), the amino compound of the formula III employed was tert-butyl (R)-3-amino-3-methylpropionate. Yield: 7 mg.

ES(+)-MS: 482.3 (M+H)+

EXAMPLE 27

((S)-2-(4,4Dimethyl-3-(4-(3-(2-methylphenyl)ureido)benzyl)-2,5-dioxoimidazolidin-1-yl)-2-(2-methylpropyl)acetyl)-L-aspartic Acid

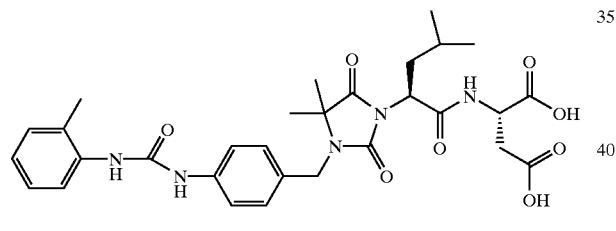

The compound was prepared by the process according to Scheme 1, Steps A, B, D (Method 1), E, F, G, H (Method 2), J (Method 1). In Step H (batch size 4.2 mmol), the amino compound of the formula III employed was di-tert-butyl L-aspartate hydrochloride. Yield: 692 mg.

ES(+)-MS: 596.4 (M+H)+

EXAMPLE 28

(2-(4,4-Dimethyl-3-(4-(3-(2-methylphenyl)ureido)benzyl)-2,5-dioxoimidazolidin-1-yl)-acetyl)-N-methyl-L-aspartic Acid

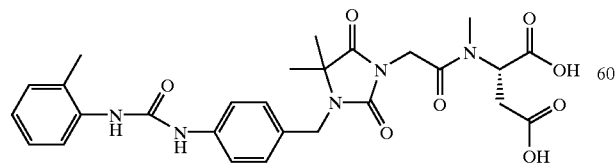

The compound was prepared by the process according to Scheme 1, Steps C, D (Method 1), E, F, G, H (Method 2), J (Method 1). In Step H (batch size 4.7 mmol), the amino compound of the formula III employed was di-tert-butyl N-methyl-L-aspartate hydrochloride. Yield: 628 mg.

ES(+)-MS: 554.3 (M+H)+

EXAMPLE 29

(S)3-(2-(3-(4-(3-(2-Methylphenyl)ureido)benzyl)-2,5-dioxoimidazolidin-1-yl)-acetylamino)-3-phenylpropionic Acid

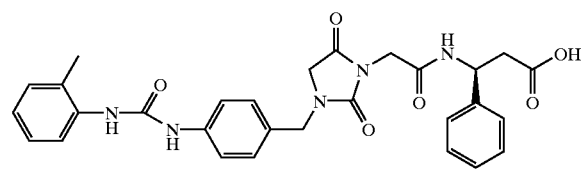

The compound was prepared by the process according to Scheme 1, Steps C, D (Method 1), E, F, G, H (Method 2), J (Method 2). In Step H (batch size 1.5 mmol), the amino compound of the formula III employed was ethyl (S)-3-amino-3phenylpropionate. Yield: 59 mg.

ES(+)-MS: 544.3 (M+H)+

EXAMPLE 30

(R)-3-(2-(3-(4-(3-(2-Chlorophenyl)ureido)benzyl)-2,5-dioxoimidazolidin-1-yl)-acetylamino)-3-methylpropionic Acid

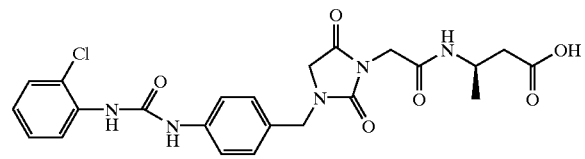

The compound was prepared by the process according to Scheme 1, Steps C, D (Method I), E, F, G, H (Method 2), J (Method 1). In Step H (batch size 1.44 mmol), the amino compound of the formula III employed was tert-butyl (R)-3-amino-3-methylpropionate. Yield: 448 mg.

ES(+)-MS: 502.3 (M+H)+

EXAMPLE 31–46

The compounds were prepared by the process according to Scheme 1, Steps C, D (Method 1), E, F, G, H (Method 2). In Step H (batch size 0.21–0.23 mmol) the amino compound of the formula III employed in the case of Examples 31–38 was tert-butyl (R)-3-amino-3-methylpropionate, in the case of Examples 39–46 ethyl (S)-3-amino-3-phenylpropionate. Step J was carried out in the case of Examples 31–38 by Method 1 (using TFA), in the case of Examples 39–46 by Method 2 (using lithium hydroxide). Yields: 30–87 mg. The compounds of the formula Ib prepared are listed in Table 1.

TABLE 1

Examples of formula Ib (Ib)

| Example No. | $R^3$ | $R^{51}$ | $R^{52}$ | $R^{53}$ | $R^{54}$ | ES-[+]-MS $[M + H]^+$ |
|---|---|---|---|---|---|---|
| 31 | Me | Me | H | Me | Me | 538.4 |
| 32 | Me | iPr | H | H | H | 538.4 |
| 33 | Me | Me | H | H | Et | 538.4 |
| 34 | Me | Me | H | H | Me | 524.4 |
| 35 | Me | Me | H | Me | H | 524.4 |
| 36 | Me | Me | Me | H | H | 524.4 |
| 37 | Me | Et | H | H | H | 524.4 |
| 38 | Me | CO$_2$Me | H | H | H | 554.3 |
| 39 | Ph | Me | H | Me | Me | 600.4 |
| 40 | Ph | iPr | H | H | H | 600.4 |
| 41 | Ph | Me | H | H | Et | 600.3 |
| 42 | Ph | Me | H | H | Me | 586.3 |
| 43 | Ph | Me | H | Me | H | 586.3 |
| 44 | Ph | Me | Me | H | H | 586.3 |
| 45 | Ph | Et | H | H | H | 586.3 |
| 46 | Ph | CO$_2$H | H | H | H | 602.3 |

EXAMPLE 47

((S)-2-(4,4-Dimethyl-3-(4-(3-(2-methylphenyl)ureido)benzyl)-2,5-dioxoimidazolidin-1-yl)-2-(2-methylpropyl)acetyl)-L-aspartyl-L-phenylglycine

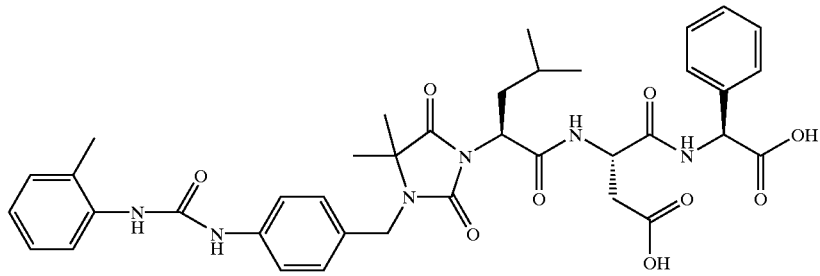

The compound was prepared by the process according to Scheme 1, Steps A, B, D, (Method 1), E, F, G, H (Method 1), J (Method 1). In Step H (batch size 1.04 mmol), the amino compound of the formula III employed was H-Asp(OtBu)-Phg-OtBu (hydrochloride). Yield: 350 mg.

ES(+)-MS: 729.4 (M+H)$^+$

EXAMPLE 48–69

The compounds were prepared by the process according to Scheme 4 by coupling hydantoincarboxylic acids of the formula IIa to H-Asp-Phg-OtBu which was linked to Wang polystyrene resin via the free COOH group of the Asp unit. The amino acid ester of the formula H$_2$N—CH(R$^{41}$)—COOtBu in Scheme 4 that was employed was L-phenylglycine tert-butyl ester. The compounds of the formula Ic prepared are listed in Table 2.

TABLE 2

(Ic)

Examples of the formula Ic

| Example No. | $R^{32}$ | ES-[+]-MS $[M + H]^+$ |
|---|---|---|
| 48 | 3-Fluorophenyl | 733.4 |
| 49 | 4-Fluorophenyl | 733.4 |
| 50 | 4-Methylphenyl | 729.4 |
| 51 | 3-Methylphenyl | 729.4 |
| 52 | n-Propyl | 681.4 |
| 53 | 4-Isopropylphenyl | 757.4 |
| 54 | 3,5-Bistrifluoromethylphenyl | 851.4 |
| 55 | 4-Trifluoromethoxyphenyl | 799.4 |
| 56 | 2-Trifluoromethoxyphenyl | 799.4 |
| 57 | 2-Nitrophenyl | 760.4 |
| 58 | Benzyl | 729.5 |
| 59 | Phenyl | 715.3 |
| 60 | 4-Methoxyphenyl | 745.4 |
| 61 | 2-Methoxyphenyl | 745.4 |
| 62 | 2-Chlorophenyl | 749.4 |
| 63 | Isopropyl | 681.4 |
| 64 | 3-Methoxyphenyl | 745.4 |
| 65 | tert-Butyl | 695.4 |
| 66 | Cyclohexyl | 721.4 |
| 67 | 2-Fluorophenyl | 733.4 |
| 68 | 2-Trifluoromethylphenyl | 783.3 |
| 69 | 4-Trifluoromethylphenyl | 783.3 |

EXAMPLE 70–87

The compounds were prepared by the process according to Scheme 5, Variant A, by coupling hydantoincarboxylic acids of the formula IIa to 3-amino-3-(3,4-ethylene-dioxyphenyl)propionic acid, which was linked to the resin via the free COOH group. The compounds of the formula Id prepared are listed in Table 3.

TABLE 3

(Id)

Examples of the formula Id

| Example No. | $R^{32}$ | ES-[+]-MS $[M + H]^+$ |
|---|---|---|
| 70 | 3-Fluorophenyl | 690.3 |
| 71 | 4-Fluorophenyl | 690.3 |

TABLE 3-continued (Id)

Examples of the formula Id

| Example No. | $R^{32}$ | ES-[+]-MS $[M + H]^+$ |
|---|---|---|
| 72 | 4-Methylphenyl | 686.4 |
| 73 | 3-Methylphenyl | 686.4 |
| 74 | n-Propyl | 638.4 |
| 75 | 4-Isopropylphenyl | 714.4 |
| 76 | 3,5-Bistrifluoromethylphenyl | 808.3 |
| 77 | 4-Trifluoromethoxyphenyl | 756.3 |
| 78 | 2-Trifluoromethoxyphenyl | 756.3 |
| 79 | 2-Nitrophenyl | 717.3 |
| 80 | Benzyl | 686.4 |
| 81 | 2-Methylphenyl | 690.4 |
| 82 | 2-Trifluoromethylphenyl | 740.3 |

TABLE 3-continued

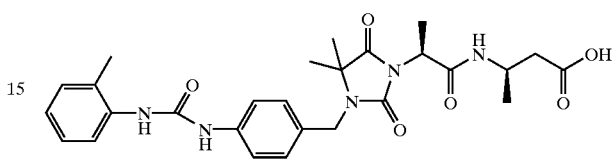

(Id)

| Example No. | Examples of the formula Id R³² | ES-[+]-MS [M + H]⁺ |
|---|---|---|
| 83 | Ethyl | 624.4 |
| 84 | 4-Trifluoromethylphenyl | 740.3 |
| 85 | 4-Methoxyphenyl | 702.4 |
| 86 | 2-Methoxyphenyl | 702.4 |
| 87 | 2-Chlorophenyl | 706.3 |

EXAMPLE 88

Sodium (R)-3-((S)-2-(4,4-dimethyl-3-(4-(3-phenylureido)benzyl)-2,5-dioxoimidazolidin-1-yl)-2-(2-methylpropyl)acetylamino)-3-methylpropionate

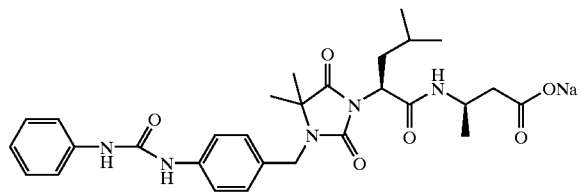

1 equivalent of 1N sodium hydroxide solution was added to a solution of 1 g (1.81 mmol) of (R)-3-((S)-2-(4,4-dimethyl-3-(4-(3-phenylureido)benzyl)-2,5-dioxoimidazolidin-1-yl)-2-(2-methylpropyl)acetylamino)-3-methylpropionic acid in 20 ml of THF and 50 ml of water. After 30 minutes at room temperature, the majority of the THF was removed in vacuo and the residue was freeze-dried. After chromatography on Sephadex LH20 (eluent:water), 930 mg of the title salt were obtained.

ES(+)-MS: 552.5 (M+H)⁺, 574.4 (sodium salt)

EXAMPLE 89

(R)-3-((S)-2-(4,4-Dimethyl-3-(4-(3-phenylureido)benzyl)-2,5-dioxoimidazolidin-1-yl)-2-methylacetylamino)-3-methylpropionic Acid

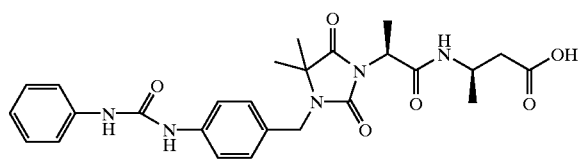

The compound was prepared by the process according to Scheme 2 (Step J by Method 1). In Step H (batch size 5.2 mmol), the amino compound of the formula III employed was tert-butyl (R)-3-amino-3-methylpropionate. Yield: 1.86 g.

ES(+)-MS: 510.4 (M+H)⁺

EXAMPLE 90

(R)-3-((S)-2-(4,4-Dimethyl-3-(4-(3-(2-methylphenyl)ureido)benzyl)-2,5-dioxoimidazolidin-1-yl)-2-methyl-acetylamino)-3-methylpropionic Acid

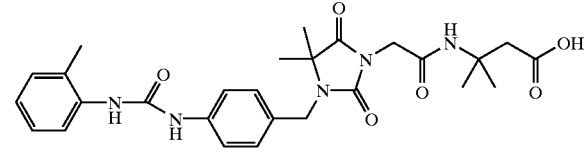

The compound was prepared by the process according to Scheme 2 (Step J by Method 1). In Step H (batch size 11.9 mmol), the amino compound of the formula III employed was tert-butyl (R)-3-amino-3-methylpropionate. Yield: 4.3 g.

FAB(+)-MS: 524.3 (M+H)⁺

EXAMPLE 91

3-(2-(4,4-Dimethyl-3-(4-(3-(2-methylphenyl)ureido)benzyl)-2,5-dioxoimidazolidin-1-yl)acetylamino)-3,3-dimethylpropionic Acid

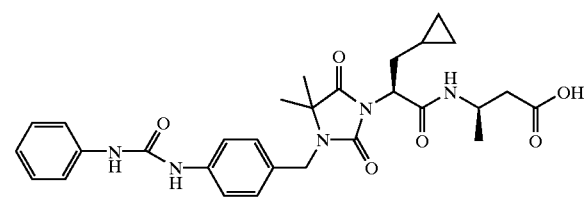

The compound was prepared by the process according to Scheme 1, Steps C, D (Method 1), E, F, G, H (Method 2), J (Method 2). In Step H (batch size 0.9 mmol), the amino compound of the formula III employed was methyl 3-amino-3,3-dimethylpropionate. Yield: 53 mg.

ES(+)-MS: 524.4 (M+H)⁺

EXAMPLE 92

(R)-3-((S)-2-(4,4-Dimethyl-3-(4-(3-phenylureido)benzyl)-2,5-dioxoimidazolidin-1-yl)-2-cyclopropylmethylacetylamino)-3-methylpropionic Acid The compound was prepared by the process according to Scheme 2, (Step J by Method 1). In Step H (batch size 1.29 mmol), the amino compound of the formula III employed was tert-butyl (R)-3-amino-3-methylpropionate.

Yield: 493 mg. ES(+)-MS: 550.5 (M+H)⁺

EXAMPLE 93

(S)-3-(2-(4,4-Dimethyl-3-(4-(3-(2-methylphenyl)ureido)benzyl)-2,5-dioxoimidazolidin-1-yl)acetylamino)-3-(3,4-methylenedioxyphenyl)propionic Acid

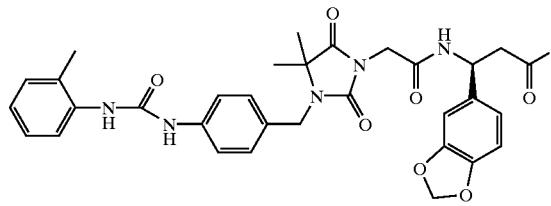

The compound was prepared by the process according to Scheme 1, Steps C, D (Method 1) E, F, G, H (Method 2), J (Method 1). In Step H (batch size 4 mmol), the amino compound of the formula III employed was tert-butyl (S)-3-amino-3-(3,4-methylenedioxyphenyl)propionate. Yield: 1.08 g.

FAB(+)-MS: 616.2 (M+H)$^+$

EXAMPLE 94

(S)-2-Benzyoxycarbonylamino-3-((4,4-dimethyl-3-(4-(2-methylphenyl)ureido)-benzyl)-2,5-dioxoimidazolidin-1-yl)acetylamino)propionic Acid The compound was prepared by the process according to Scheme 1, Steps C, D (Method 1), E, F, G, H (Method 2), J (Method 1). In Step H (batch size 1.89 mmol), the amino compound of the formula III employed was tert-butyl (S)-3-amino-2-benzyloxycarbonylaminopropionate. Yield: 410 mg.

FAB(+)-MS: 645.2 (M+H)$^+$

EXAMPLE 95–116

The esters of Examples 95, 96, 98–102 and 104–116 were prepared from the corresponding carboxylic acids (compounds of the formula I where E=R$^{10}$CO, R$^{10}$=hydroxyl) by esterification of the COOH group by the following general procedure: 6 equivalents of the corresponding absolute alcohol and then 0.8 equivalent of DMAP and 1.1 equivalents of DCC were added to a solution of the carboxylic acid in absolute DCM (7–10 ml per mmol of carboxylic acid) and the reaction mixture was allowed to stand at room temperature overnight. After filtration, the solvent was removed in vacuo and the residue was purified by chromatography. The esters of Examples 97 and 103 were obtained directly in the preparation of the carboxylic acids of Examples 19 and 11 (as intermediates in Step H).

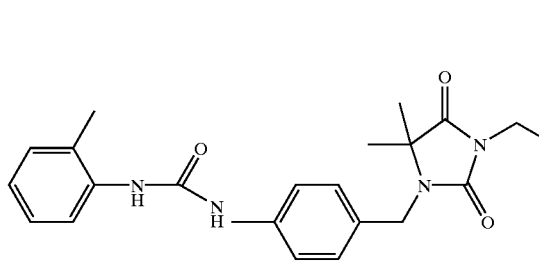

The esters of the formula Ie prepared are listed in Table 4.

TABLE 4

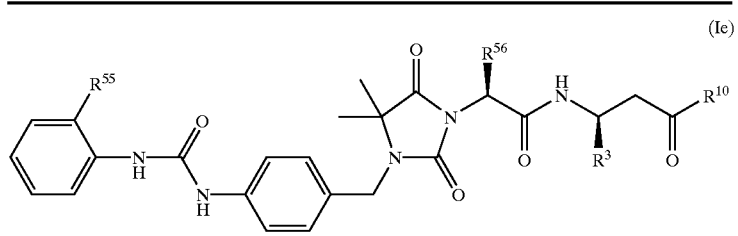

Examples of the formula Ie

| Example No. | R$^{55}$ | R$^{56}$ | R$^3$ | R$^{10}$ | ES-[+]- or FAB-[+]-MS [M + H]$^+$ |
|---|---|---|---|---|---|
| 95 | H | iBu | Me | OiPr | 594.4 |
| 96 | H | iBu | Me | OEt | 580.3 |

TABLE 4-continued (Ie)

Examples of the formula Ie

| Example No. | $R^{55}$ | $R^{56}$ | $R^3$ | $R^{10}$ | ES-[+]- or FAB-[+]-MS $[M + H]^+$ |
|---|---|---|---|---|---|
| 97 | H | iBu | Ph | OEt | 642.3 |
| 98 | H | iBu | Ph | OiPr | 656.5 |
| 99 | H | iBu | Ph | OiBu | 670.5 |
| 100 | H | iBu | Me | OiBu | 608.5 |
| 101 | H | iBu | Me | OMe | 566.4 |
| 102 | Me | H | Ph | OiPr | 614.4 |
| 103 | Me | H | Ph | OEt | 600.4 |
| 104 | Me | H | Me | OEt | 538.4 |
| 105 | Me | H | Me | OiPr | 552.4 |
| 106 | H | Me | Me | OiPr | 552.4 |
| 107 | H | Me | Me | OEt | 538.4 |
| 108 | Me | Me | Me | OEt | 552.4 |
| 109 | Me | Me | Me | OiPr | 566.5 |
| 110 | Me | H | Me | OiBu | 566.3 |
| 111 | H | Cyclopropyl-$CH_2$— | Me | OEt | 578.6 |
| 112 | H | Cyclopropyl-$CH_2$— | Me | OiPr | 592.6 |
| 113 | Me | H | Me | OMe | 524.5 |
| 114 | Me | H | 3,4-Methylene-dioxyphenyl | OiPr | 658.3 |
| 115 | Me | H | Me | OnPr | 552.2 |
| 116 | Me | H | Me | OnBu | 566.5 |

EXAMPLE 117

Isopropyl (2-(4,4-Dimethyl-3-(4-(3-(2-methylphenyl)ureido)benzyl)-2,5-dioxoimidazolidin-1-yl)-acetyl)-L-(2-adamantyl)aspartamidate

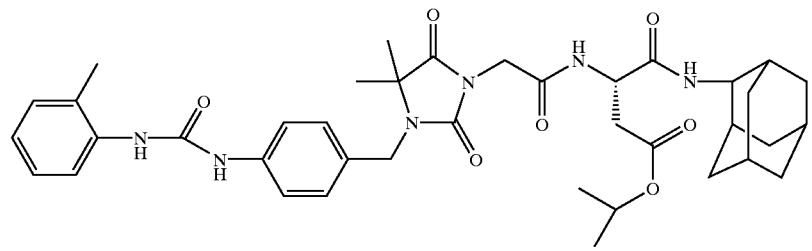

The compound was prepared from (2-(4,4-dimethyl-3-(4-(3-(2-methylphenyl)ureido)benzyl)-2,5-dioxoimidazolidin-1-yl)acetyl)-L-(2-adamantyl)aspartamide and isopropanol as described for Examples 95, 96, 98–102 and 104–116.
Batch size: 0.371 mmol of the starting aspartyl compound.
Yield: 210 mg.
ES(+)-MS: 715.4 $(M+H)^+$

EXAMPLE 118

Isopropyl (S)-2-Benzyloxycarbonylamino-3-((4,4-dimethyl-3-(4-(3-(2-methylphenyl)ureido)-benzyl)-2,5-dioxoimidazolidin-1-yl)acetylamino)propionate

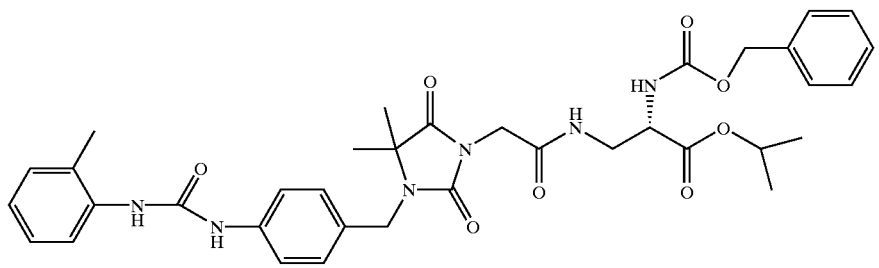

The compound was prepared from (S)-2-benzyloxycarbonylamino-3-((4,4-dimethyl-3-(4-(3-(2-methylphenyl)ureido)benzyl)-2,5-dioxoimidazolidin-1-yl)acetylamino)propionic acid and isopropanol as described in Examples 95, 96, 98–102 and 104–116. Batch size: 0.465 mmol of the starting propionic acid. Yield: 233 mg.

FAB(+)-MS: 687.3 (M+H)$^+$

EXAMPLE 119–124

The synthesis was carried out analogously to N. M. Nielsen, H. Bundgaard, Journal of Pharmaceutical Sciences, 1988, 77 (4), 285, incorporated by reference herein in its entirety, by reaction of (R)-3-(2-(4,4-dimethyl-3-(4-(3-(2-methylphenyl)ureido)-benzyl)-2,5-dioxoimidazolidin-1-yl)acetylamino)-3-methylpropionic acid with the respective chloroacetamide (Examples 119, 120, 122) or with chloromethyl pivalate (Example 121) or with (1-chloroethyl)ethyl carbonate (Example 123) or with bromomethyl acetate (Example 124). The reactions were carried out at 80° C. The substances were purified by means of preparative HPLC on Sephadex LH20 (eluent: acetonitrile/water). Batch size: 1.374 mmol of the starting propionic acid. The compounds of the formula if prepared are listed in Table 5.

TABLE 5

(If)

Examples of the formula If

| Example No. | R$^{10}$ | Yield | ES-[+]- or FAB-[+]- MS [M + H]$^+$ |
|---|---|---|---|
| 119 | O—CH$_2$—CO—NMe$_2$ | 280 mg | 595.5 |
| 120 | O—CH$_2$—CO—NEt$_2$ | 435 mg | 623.3 |
| 121 | O—CH$_2$—O—CO-tBu | 291 mg | 624.1 |
| 122 | O—CH$_2$—CO—NH$_2$ | 374 mg | 567.5 |
| 123 | O—CH[Me]—O—CO—OEt | 133 mg | 626.5 |
| 124 | O—CH$_2$—O—CO—Me | 276 mg | 582.5 |

EXAMPLE 125–129

Examples 125, 127, 128 and 129 were prepared by the process according to Scheme 1, Steps A, B, D (Method 1), E, F, G, H (Method 2). In Step H, the amino compound of the formula III employed was (R)-3-amino-3-methylpropanol (Examples 125 and 129) or (S)-3-amino-3-phenylpropanol (Example 128) or (S)-3-amino-3-(4-methoxyphenyl)propanol (Example 127). Example 126 was prepared by the process according to Scheme 1, Steps C, D (Method 1), E, F, G, H (Method 2). In Step H, the amino compound of the formula III employed was (S)-3-amino-3-phenylpropanol. The compounds of the formula Ig prepared are listed in Table 6.

TABLE 6

Examples of the formula Ig (Ig)

| Example No. | $R^{57}$ | $R^{58}$ | $R^3$ | ES-[+]- or FAB-[+]-MS [M + H]$^+$ |
|---|---|---|---|---|
| 125 | H | iBu | Me | 538.4 |
| 126 | Me | H | Ph | 558.3 |
| 127 | H | iBu | 4-Methoxyphenyl | 630.3 |
| 128 | H | iBu | Ph | 600.2 |
| 129 | Me | iBu | Me | 552.2 |

The 3-aminopropanols employed in the preparation of the compounds of Examples 125–129 were prepared as follows.

(S)-3-Amino-3-phenylpropanol 1.45 g (38.1 mmol) of lithium aluminum hydride were added in portions with ice-cooling to a suspension of 3.5 g (15.2 mmol) of ethyl (S)-3-amino-3-phenyl-propionate hydrochloride in 150 ml or absolute THF and the mixture was stirred at room temperature for 1 hour. 5 ml of water were then cautiously added dropwise with ice-cooling. The precipitate was filtered off and the filtrate was concentrated in vacuo. The residue was taken up in DCM and the solution was extracted with water. The organic phase was dried over sodium sulfate. After filtration and removal of the solvent in vacuo, 1.84 g of (S)-3-amino-3-phenylpropanol were obtained.

(R)-3-Amino-3-methylpropanol and (S)-3-Amino-3-(4-methoxyphenyl)propanol 1 equivalent of lithium aluminum hydride was added in portions to a solution of aluminum trichloride in absolute diethyl ether (about 3 ml per mmol of aluminum trichloride) and the mixture was heated under reflux for 30 minutes. 0.4 equivalent of tert-butyl (R)-3-amino-3-methylpropionate or tert-butyl (S)-3-amino-3-(4-methoxyphenyl)propionate was slowly added dropwise and the reaction mixture was heated under reflux for 1 hour. Water (0.072 ml per mmol of lithium aluminum hydride) and a solution of potassium hydroxide in water (per mmol of lithium aluminum hydride 1.688 g of potassium hydroxide in 2.8 ml of water) were then cautiously added dropwise with ice-cooling. The mixture was allowed to stand overnight at room temperature, the ether phase was decanted off and the residue was stirred several times with diethyl ether and DCM. The combined organic phases were dried over sodium sulfate. After filtration and removal of the solvent in vacuo, the corresponding aminoalcohol was obtained.

EXAMPLE 130
(R)-3-((S)-2-(4,4-Dimethyl-3-(4-(3-phenylureido)benzyl)-2,5-dioxoimidazolidin-1-yl)-2-(2-methylpropyl)acetylamino)-3-methylpropanal

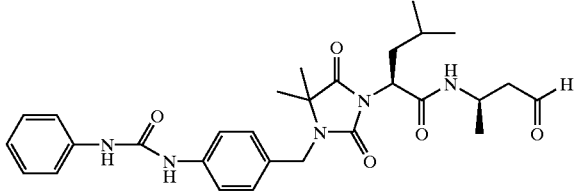

56.5 mg of (R)-3-((S)-2-(4,4-Dimethyl-3-(4-(3-phenylureido)-benzyl)-2,5-dioxoimidazolidin-1-yl)-2-(2-methylpropyl)acetylamino)-3-methylpropanol were dissolved in a mixture of 3 ml of ethyl acetate, 1 ml of toluene and 1 ml of water with 10.8 mg of potassium bromide. After addition of a catalytic amount of 4-acetamido-2,2,6,6-tetramethylpiperidine-1-oxyl (=4-acetamido-TEMPO), a mixture of 0.5 ml of sodium hypochlorite solution (13% strength), 0.5 ml of saturated sodium hydrogencarbonate solution and 1 ml of water was added dropwise at 0° C. The mixture was stirred at 0° C. for 25 minutes. After reaction was complete, the mixture was treated with ethyl acetate, and the organic phase was washed with sodium thiosulfate solution and dried over sodium sulfate. After filtration, the solvent was removed on a rotary evaporator and the residue was purified by reversed phase HPLC (water/acetonitrile). Yield: 15 mg.

EXAMPLE 131
(R)-3-((S)-2-(4,4-Dimethyl-3-(4-(3-phenylureido)benzyl)-2,5-dioxoimidazolidin-1-yl)-2-(2-methylpropyl)acetylamino)-3-methylpropionamide

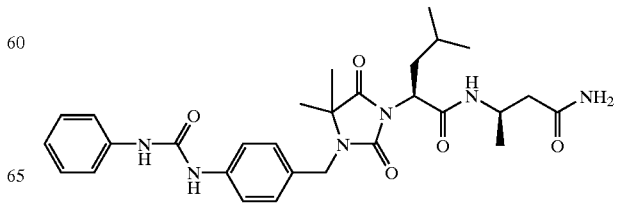

The compound was prepared from 0.5 g of (R)-3-((S)-2-(4,4-dimethyl-3-(4-(3-phenylureido)benzyl)-2,5-dioxoimidazolidin-1-yl)-2-(2-methylpropyl)acetylamino)-3-methylpropionic acid and Rink amide resin by the general procedure described above for the preparation of unsubstituted carboxamides on the solid phase. Yield: 349 mg.

ES(+)-MS: 551.3 (M+H)+

EXAMPLE 132

(S)-3-((S)-2-(4,4-Dimethyl-3-(4-(3-phenylureido)benzyl)-2,5-dioxoimidazolidin-1-yl)-2-(2-methylpropyl)acetylamino)-3-phenylpropionamide

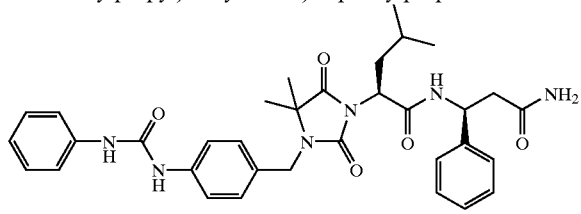

The compound was prepared analogously to Example 131 from (S)-3-((S)-2-(4,4-dimethyl-3-(4-(3-phenylureido)benzyl)-2,5-dioxoimidazolidin-1-yl)-2-(2-methylpropyl)acetylamino)-3-phenylpropionic acid.

ES(+)-MS: 613.3 (M+H)+

EXAMPLE 133

((S)-2-(4,4-Dimethyl-3-(4-(3-(2-methylphenyl)ureido)benzyl)-2,5-dioxoimidazolidin-1-yl)-2-(2-methylpropyl)acetyl)-L-aspartyl-L-valyl-L-proline The compound was prepared by solid-phase synthesis analogously to the general procedure described above for the preparation of compounds of the formula I which contain a peptide unit. For the synthesis of the tripeptide unit Asp-Val-Pro, 6 g of 2-chlorotrityl chloride polystyrene resin were first loaded with 4 g of Fmoc-Pro-OH. After removal of the Fmoc protective group, 3.1 g of Fmoc-Val-OH were employed in the second coupling step and, after repeated removal of the Fmoc group, 3.4 g of Fmoc-Asp(OtBu)-OH in the third coupling step. 11 g of the resin loaded with Fmoc-Asp(OtBu)-Val-Pro were obtained. After removal of the Fmoc group, 4 g of this resin were coupled using 2.7 g of (S)-2-(4,4-dimethyl-3-(4-(3-(2-methylphenyl)ureido)benzyl)-2,5-dioxoimidazolidin-1-yl)-2-(2-methylpropyl)acetic acid, 1.8 g of TOTU, 0.75 g of HOBT and 0.72 g of DIPEA in 25 ml of DMF. After washing the resin, the compound was removed from the resin using TFA/DCM (and at the same time the tert-butyl ester protective group was cleaved). The cleavage solution was concentrated and the residue was crystallized using diethyl ether. Yield 750 mg.

ES(+)-MS: 792.5 (M+H)+

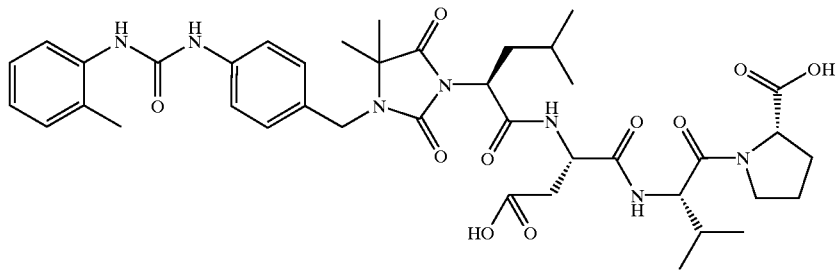

EXAMPLE 134

(2-(4,4-Dimethyl-3-(4-(3-(2-methylphenyl)ureido)benzyl)-2,5-dioxoimidazolidin-1-yl)acetyl)-L-(2-adamantyl)aspartamide

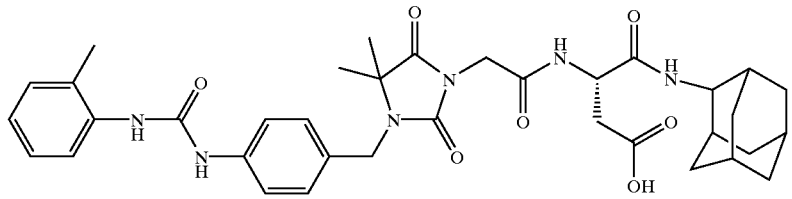

The compound was prepared by the process according to Scheme 1, Steps C, D (Method 1), E, F, G, H (Method 2), J (Method 1). In Step H (batch size 1.41 mmol), the amino compound of the formula III employed was tert-butyl L-(2-adamantyl)aspartamidate. Yield: 504 mg.

ES(+)-MS: 673.4 (M+H)$^+$

EXAMPLE 135–158

The ureas of Examples 135–158 were prepared by the process according to Scheme 5, Variant B. As described above, the corresponding 3-(4-(N-Fmoc-amino)-benzyl)-hydantoincarboxylic acids were coupled to 3-amino-3-(3,4-methylenedioxyphenyl)propionic acid, which was linked to the resin via the free COOH group, then the Fmoc protective group was removed and the amino group was derivatized by reaction with the appropriate isocyanate or with di(N-succinimidyl) carbonate and the appropriate amine. The compounds of the formula Ih prepared are listed in Table 7.

TABLE 7

(Ih)

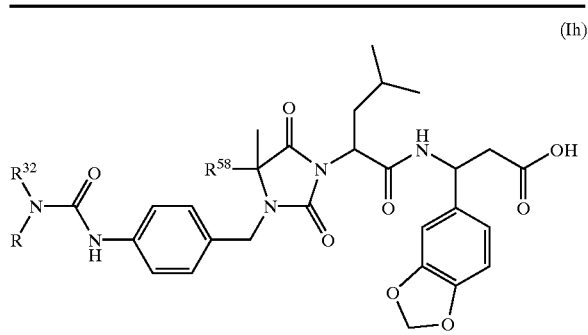

Examples of the formula Ih

| Example No. | R$^{32}$ | R | R$^{58}$ | ES-[+]- or FAB-[+]- MS [M + H]$^+$ |
|---|---|---|---|---|
| 135 | 2-Methylphenyl | H | Me | 672 |
| 136 | 2-Methoxybenzyl | H | Ph | 764 |
| 137 | 2-Methylphenyl | Me | Ph | 748 |
| 138 | 2-Trifluoromethylphenyl | H | Me | 726 |
| 139 | Ethyl | H | Me | 610 |
| 140 | 4-Trifluoromethylphenyl | H | Me | 726 |
| 141 | Cyclohexyl | H | Me | 664 |
| 142 | 3-Methylphenyl | H | Me | 672 |
| 143 | 4-Fluorophenyl | H | Me | 676 |
| 144 | 4-Methylphenyl | H | Me | 672 |
| 145 | n-Propyl | H | Me | 624 |
| 146 | 4-Isopropylphenyl | H | Me | 700 |
| 147 | 3,5-Bistrifluoromethylphenyl | H | Me | 794 |
| 148 | 4-Trifluoromethoxyphenyl | H | Me | 742 |
| 149 | 2-Trifluoromethoxyphenyl | H | Me | 742 |

TABLE 7-continued (Ih)

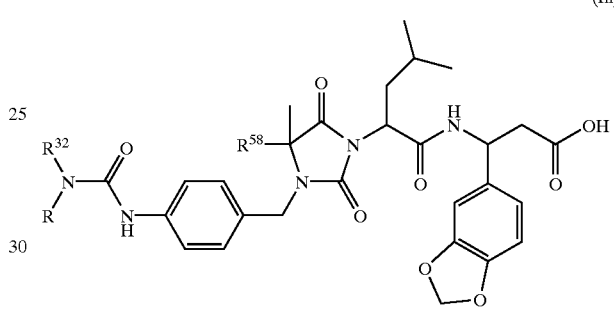

Examples of the formula Ih

| Example No. | R$^{32}$ | R | R$^{58}$ | ES-[+]- or FAB-[+]- MS [M + H]$^+$ |
|---|---|---|---|---|
| 150 | 2-Nitrophenyl | H | Me | 703 |
| 151 | 4-Methoxyphenyl | H | Me | 688 |
| 152 | 2-Methoxyphenyl | H | Me | 688 |
| 153 | 2-Chlorophenyl | H | Me | 692 |
| 154 | Isopropyl | H | Me | 624 |
| 155 | 3-Methoxyphenyl | H | Me | 688 |
| 156 | tert-Butyl | H | Me | 638 |
| 157 | Benzyl | H | Me | 672 |
| 158 | Phenyl | H | Me | 658 |

EXAMPLE 159–166

The thioureas of Examples 159–166 were prepared by the process according to Scheme 5, Variant B. As described above, the corresponding 3-(4-(N-Fmoc-amino)-benzyl)hydantoincarboxylic acid was coupled to 3-amino-3-(3,4-methylenedioxy-phenyl)propionic acid which was linked to the resin via the free COOH group, then the Fmoc protective group was removed and the amino group was derivatized by reaction with the appropriate isothiocyanate. The compounds of the formula Ik prepared are listed in Table 8.

TABLE 8

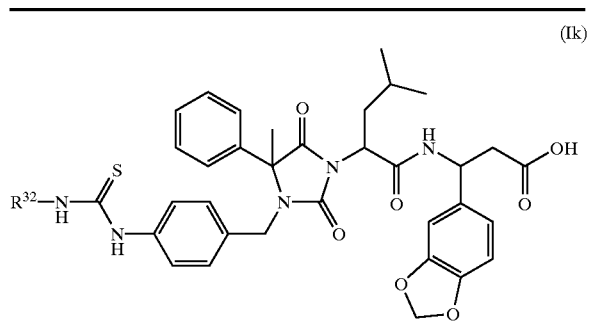

(Ik)

Examples of the formula Ik

| Example No. | R³² | ES-[+]- or FAB-[+]- MS [M + H]⁺ |
|---|---|---|
| 159 | 2-Methylphenyl | 750 |
| 160 | 4-Methylphenyl | 750 |
| 161 | Benzyl | 750 |
| 162 | 2-Iodophenyl | 862 |
| 163 | 2-Methoxyphenyl | 766 |
| 164 | tert-Butyl | 716 |
| 165 | 2-Tetrahydrofurylmethyl | 744 |
| 166 | 3-Methoxyphenyl | 766 |

EXAMPLE 167–182

The compounds of Examples 167–182 were prepared by the process according to Scheme 5, Variant B. As described above, the corresponding 3-(4-(N-Fmoc-amino)-benzyl)hydantoincarboxylic acid was coupled to 3-amino-3-(3,4-methylenedioxy-phenyl)propionic acid, which was linked to the resin via the free COOH group, then the Fmoc protective group was removed and the amino group was converted into a carbamate or an amide as described. The compounds of the formula Im prepared are listed in Table 9.

TABLE 9

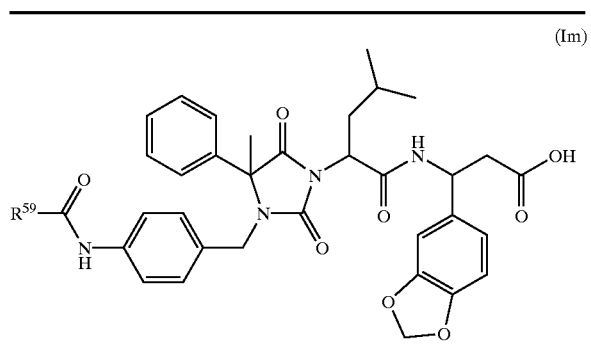

(Im)

Examples of the formula Im

| Example No. | R⁵⁹ | ES-[+]- or FAB-[+]-MS [M + H]⁺ |
|---|---|---|
| 167 | Benzyloxy | 735 |
| 168 | Phenyloxy | 721 |
| 169 | Phenyl | 705 |
| 170 | 2-Methylbenzyl | 733 |
| 171 | 2-Methylphenyl | 719 |
| 172 | 2-Chlorophenyl | 740 |
| 173 | 2-Fluorophenyl | 723 |
| 174 | 2-Nitrophenyl | 750 |
| 175 | 2-Trifluoromethylbenzyl | 787 |
| 176 | 2-Iodophenyl | 831 |
| 177 | 2-Methoxyphenyl | 735 |
| 178 | 2-Bromophenyl | 784 |

TABLE 9-continued

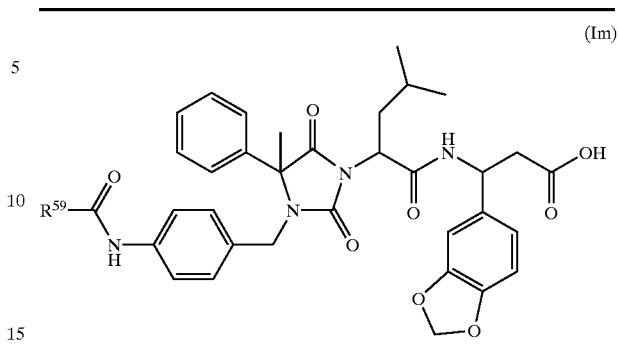

(Im)

Examples of the formula Im

| Example No. | R⁵⁹ | ES-[+]- or FAB-[+]-MS [M + H]⁺ |
|---|---|---|
| 179 | 2-Bromobenzyl | 798 |
| 180 | 2-Fluorobenzyl | 737 |
| 181 | 2-Nitrobenzyl | 764 |
| 182 | 2-Chlorobenzyl | 754 |

EXAMPLE 183

(2RS,3S)-3-((S)-2-(4,4-Dimethyl-3-(4-(3-(2-methylphenyl)ureido)benzyl)-2,5-dioxoimidazolidin-1-yl)-2-(2-methylpropyl)acetylamino)-2,3-diphenylpropionic Acid

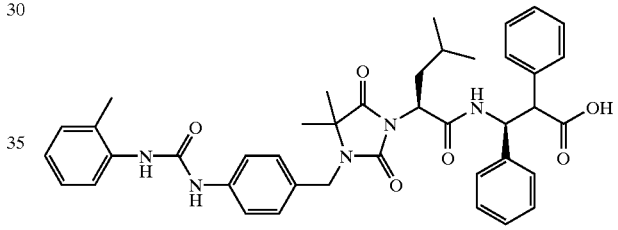

The compound was prepared by the process according to Scheme 1. Steps A, B, D (Method 1), E, F, G, H (Method 2). In Step H (batch size 0.33 mmol), the amino compound of the formula III employed was methyl (2RS,3R)-3-amino-2,3-diphenylpropionate. In Step J, the cleavage of the ester protective group was carried out analogously to Method 2 using 5 equivalents of a 1N aqueous lithium hydroxide solution in methanol for 3 hours and acidifying the solution with TFA to pH 3. Filtration of the solid obtained with suction and drying in vacuo afforded the title compound. Yield: 81 mg.

ES(+)-MS: 704.2 (M+H)⁺

EXAMPLE 184–188

The compounds were prepared by the process according to Scheme 1, Steps A, B, D (Method 1), E, F, G, H (Method 2). In Step H (batch size 0.5 mmol), the amino compound of the formula III employed in the case of Examples 184, 185, 186 and 188 was the corresponding tert-butyl (S)-3-amino-3-arylpropionate, and in the case of Example 187 the ethyl (S)-3-amino-3-pentafluorophenylpropionate. In the case of Examples 184, 185, 186 and 188, Step J was carried out according to Method 1 using TFA, in the case of Example 187 analogously to Method 2 using lithium hydroxide as described in Example 183. The product obtained in Example 187 contained lithium trifluoroacetate. The (S)-3-((S)-(2-(4,4-dimethyl-3-(4-(3-(2-methylphenyl)ureido)benzyl)-2,5-dioxoimidazolidin-1-yl)-2-(2-methylpropyl)acetylamino)-3-arylpropionic acids of the formula In prepared are listed in Table 10.

TABLE 10

(In)

[Structure of formula In]

Examples of the formula In

| Example No. | R³ | Yield | ES-[+]-MS [M + H]⁺ |
|---|---|---|---|
| 184 | 2-Naphthyl | 85 mg | 678.3 |
| 185 | 4-Biphenylyl | 140 mg | 704.3 |
| 186 | 1-Naphthyl | 100 mg | 678.3 |
| 187 | Pentafluorophenyl | 580 mg | 724.5 |
| 188 | 2,4-Dimethoxyphenyl | 320 mg | 688.5 |

EXAMPLE 189

(S)-3-((RS)-2-((RS)-4-Methyl-4-phenyl-3-(4-(3-(2-methylphenyl)ureido)benzyl)-2,5-dioxoimidazolidin-1-yl)-2-(2-methylpropyl)acetylamino)-3-(2,4-dimethoxyphenyl)propionic Acid

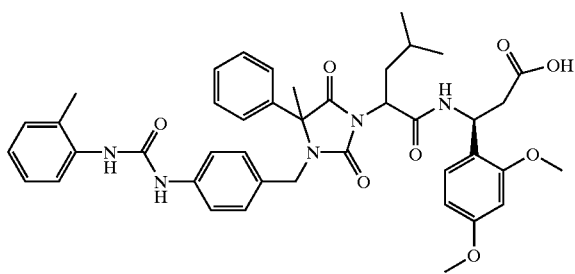

The compound was prepared by the process according to Scheme 1, Steps C, D (Method 1), E, F, G, H (Method 2), J (Method 1). In Step H (batch size 0.5 mmol), the amino compound of the formula III employed was tert-butyl (S)-3-amino-3-(2,4-dimethoxyphenyl)propionate. Yield: 320 mg.

ES(+)-MS: 750.5 (M+H)⁺

EXAMPLE 190–194

The compounds were prepared by the process according to Scheme 1, Steps C, D (Method 1), E, F, G, H (Method 2). In Step H (batch size 0.25 mmol), the corresponding ethyl (RS)-3-amino-3-arylpropionate was employed. The cleavage of the ester protective group in Step J was carried out analogously to Method 2 using lithium hydroxide as described in Example 183. The (RS)-3-((RS)-(2-((RS)-4-methyl-4-phenyl-3-(4-(3-(2-methylphenyl)ureido)-benzyl)-2,5-dioxoimidazolidin-1-yl)-2-(2-methylpropyl) acetylamino)-3-arylpropionic acids of the formula Ip prepared are listed in Table 11.

TABLE 11

(Ip)

[Structure of formula Ip]

Examples of the formula Ip

| Example No. | R³ | Yield | ES-[+]-MS [M + H]⁺ |
|---|---|---|---|
| 190 | 3,4-Dimethoxyphenyl | 145 mg | 750.4 |
| 191 | 4-tert-Butylphenyl | 161 mg | 752.4 |
| 192 | 4-Fluorophenyl | 163 mg | 714.3 |

TABLE 11-continued (Ip)

Examples of the formula Ip

| Example No. | $R^3$ | Yield | ES-[+]-MS [M + H]+ |
|---|---|---|---|
| 193 | 4-Methoxyphenyl | 159 mg | 720.5 |
| 194 | 4-Isobutylphenyl | 159 mg | 746.5 |

EXAMPLE 195

(RS)-2-Butylsulfonylamino-3-((RS)-2-((RS)-4-methyl-4-phenyl-3-(4-(3-(2-methyl-phenyl)ureido)benzyl)-2,5-dioxoimidazolidin-1-yl)-2-(2-methylpropyl)acetylamino)propionic Acid

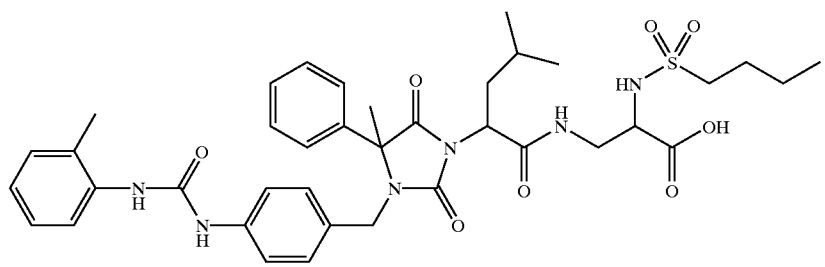

The compound was prepared by the process according to Scheme 1, Steps C, D (Method 1), E, F, G, H (Method 2). In Step H (batch size 0.25 mmol), the amino compound of the formula III employed was the ethyl (RS)-3-amino-2-(n-butylsulfonylamino)propionate. The cleavage of the ester protective group in Step J was carried out analogously to Method 2 using lithium hydroxide as described in Example 183. Yield: 259 mg (contained lithium trifluoroacetate).

ES(+)-MS: 749.4 (M+H)+

EXAMPLE 196

(RS)-3-((S)-2-(4,4-Dimethyl-3-(4-(3-(2-methylphenyl)ureido)benzyl)-2,5-dioxoimidazolidin-1-yl)-2-(2-methylpropyl)acetylamino)-3-phenylpropionic Acid

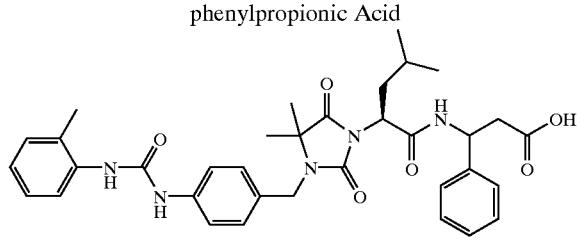

The compound was prepared analogously to the process according to Scheme 5 by coupling resin-bound (RS)-3-amino-3-phenylpropionic acid to the corresponding hydantoincarboxylic acid of the formula IIa, prepared by the process according to Scheme 1 (batch size of the coupling: 0.05 mmol of compound of the formula IIa). Yield: 4.2 mg

ES(+)-MS: 628.1 (M+H)+

EXAMPLE 97–218

The compounds were prepared analogously to the process according to Scheme 5 by coupling of the corresponding resin-bound 3-substituted (RS)-3-aminopropionic acid to the corresponding hydantoincarboxylic acid of the formula IIa, prepared by the process according to Scheme 1 (batch size of the coupling: 0.05 mmol of compound of the formula IIa). The 3-substituted (RS)-3-((RS)-(2-((RS)-4-methyl-4-phenyl-3-(4-(3-(2-methylphenyl)ureido)benzyl)-2,5-dioxoimidazolidin-1-yl)-2-(2-methylpropyl)acetylamino) propionic acids of the formula Iq prepared are listed in Table 12.

TABLE 12

Examples of the formula Iq (Iq)

| Example No. | R³ | Yield | ES-[+]-MS [M + H]⁺ |
|---|---|---|---|
| 197 | 2,3,5,6-Tetrafluorophenyl | 15.1 mg | 762.3 |
| 198 | 3-Methoxyphenyl | 9.7 mg | 720.3 |
| 199 | 3,4-Ethylenedioxyphenyl | 9.8 mg | 748.3 |
| 200 | 4-Trifluoromethoxyphenyl | 15.6 mg | 774.3 |
| 201 | 2,3-Dimethoxyphenyl | 10.0 mg | 750.5 |
| 202 | 2-Chlorophenyl | 14.6 mg | 724.3 |
| 203 | 3-Methylphenyl | 19.7 mg | 704.3 |
| 204 | 3,4-Difluorophenyl | 15.0 mg | 726.3 |
| 205 | 2,6-Difluorophenyl | 16.1 mg | 726.4 |
| 206 | tert-Butyl | 6.1 mg | 669.1 |
| 207 | 3-Fluorophenyl | 11.3 mg | 708.2 |
| 208 | 2,4,4-Trimethylpentyl | 4.3 mg | 668.3 |
| 209 | 4-Chlorophenyl | 6.4 mg | 724.3 |
| 210 | 4-Dimethylamino-1-naphthyl | 0.8 mg | 783.4 |
| 211 | Bicyclo[2.2.1]hept-2-en-5-yl | 0.6 mg | 706.4 |
| 212 | n-Octyl | 0.5 mg | 726.0 |
| 213 | 4-Methoxy-2,3-dimethylphenyl | 4.3 mg | 765.2 [M + NH₃]⁺ |
| 214 | 2-Fluorophenyl | 1.1 mg | 725.1 [M + NH₃]⁺ |
| 215 | 2,3-Dichlorophenyl | 12.8 mg | 758.3 |
| 216 | 4-Fluorophenyl | 1.7 mg | 708.3 |
| 217 | 2-Chloro-5-nitrophenyl | 13.1 mg | 746.4 |
| 218 | 4-[n-Butyl]phenyl | 17.9 mg | 746.4 |

EXAMPLE 219

((RS)-2-(RS))-4-Methyl-4-phenyl-3-(4-(3-(2-methylphenyl)ureido)benzyl)-2,5-dioxoimidazolidin-1-yl)-2-(2-methylpropyl)acetylamino)-L-aspartyl-L-phenylglycine tert-butyl Ester

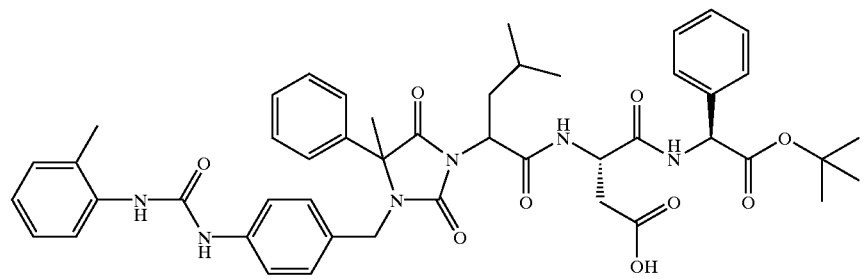

The compound was prepared by solid-phase synthesis analogously to the process according to Scheme 4. Aspartylphenylglycine tert-butyl ester, which was bonded to chlorotrityl chloride polystyrene resin, was coupled to the appropriate hydantoin-carboxylic acid of the formula IIa, prepared by the process according to Scheme 1 (batch size of the coupling: 0.05 mmol of compound of the formula IIa). The removal from the resin was carried out using a 10% strength solution of TFA in DCM for 20 minutes. Yield: 4.7 mg
ES(+)-MS: 846.9 (M+H)$^+$

EXAMPLE 220

(R)-3-(2-(4,4-Pentamethylene-3-(4-(3-(2-methylphenyl)ureido)benzyl)-2,5-dioxoimidazolidin-1-yl)acetylamino-3-methylpropionic Acid

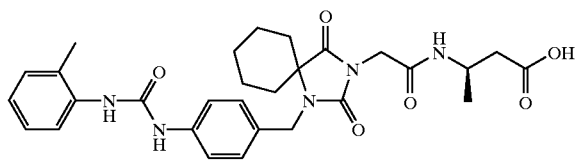

The compound can be prepared by the process according to Scheme 1, Steps C, D (Method 1), E, F, G, H (Method 2), J (Method 1). In Step H, the amino compound of the formula III employed is tert-butyl (R)-3-amino-3-methylpropionate.

EXAMPLE 221

(R)-3-((S)-2-((S)-4-(4-(Amino-imino-methyl)phenyl)-4-methyl-3-(4-(3-(2-methylphenyl)-ureido)-benzyl)-2,5-dioxoimidazolidin-1-yl)-2-(2-methylpropyl)acetylamino)-3-methylpropionic Acid

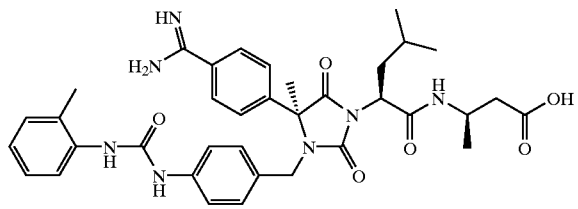

The compound can be prepared by the process according to Scheme 1. Steps A, B, D (Method 1), E, F, G, H (Method 2), J (Method 1). In Step H, the amino compound of the formula III employed is tert-butyl (R)-3-amino-3-methylpropionate.

Investigation of the Biological Activity

A) U937/VCAM-1 Cell Adhesion Test

The test method used for the activity of the compounds of the formula I on the interaction between VCAM-1 and VLA-4 is the assay described below which is specific for this interaction. The cellular binding components, i.e., the VLA-4 integrins, are supplied in their natural form as surface molecules on human U937 cells (ATCC CRL 1593). which belong to the leucocytes group. The specific binding components used are genetically engineered recombinant soluble fusion proteins, consisting of the extracytoplasmatic domain of human VCAM-1 and the constant region of a human immunoglobulin of the subclass IgG1.

Assay for the Measurement of the Adhesion of U937 Cells (ATCC CRL 1593) to hVCAM-1(1–3)-IgG 1. Preparation of Human VCAM-1 (1–3)-IgG and Human CD4-IgG A genetic construct for the expression of the extracellular domain of human VCAM-1, associated with the genetic sequence of the heavy chain of human immunoglobulin IgG1 (hinge, CH2 and CH3 regions), from Dr. Brian Seed, Massachusetts General Hospital. Boston, USA was employed (cf. Damle and Aruffo, Proc. Natl. Acad. Sci. USA 1991, 88, 6403–6407). The soluble fusion protein hVCAM-1(1–3)-IgG contained the three amino-terminal extracellular immunoglobulin-like domains of human VCAM-1 (Damle and Aruffo, Proc. Natl. Acad. Sci. USA 1991, 88, 6403–6407). CD4-IgG (Zettimeissl et al., DNA and Cell Biology 1990, 9, 347) served as a fusion protein for negative controls. The recombinant proteins were expressed as soluble proteins after DEAE/dextran-mediated DNA transfection in COS cells (ATCC CRL1651) according to standard procedures (Ausubel et al., Current Protocols in Molecular Biology, John Wiley & Sons, Inc., 1994).

2. Assay for the Measurement of the Adhesion of U937 Cells to hVCAM-1 (1–3)-IgG 2.1 96-well microtiter test plates (Nunc Maxisorb) were incubated at room temperature for 1 hour with 100 µl/well of a goat-anti-human IgG antibody solution (10 µg/ml in 50 mM tris, pH 9.5). After removal of the antibody solution, washing was carried out once with PBS.

2.2 150 µl/well of a blocking buffer (1% BSA in PBS) were incubated on the plates at room temperature for 0.5 hour. After removal of the blocking buffer, washing was carried out once with PBS.

2.3 100 µl per well of a cell culture supernatant of transfected COS cells were incubated on the plates at room temperature for 1.5 hours. The COS cells were transfected with a plasmid which codes for the three N-terminal immunoglobulin-like domains of VCAM-1, coupled to the Fc part of human IgG$_1$ (hVCAM-1 (1–3)-IgG). The content of hVCAM-1 (1–3)-IgG was about 0.5–1 µg/ml. After removal of the culture supernatant, washing was carried out once with PBS.

2.4 The plates were incubated at room temperature for 20 minutes with 100 µl/well of Fc receptor blocking buffer (1 mg/ml of γ-globulin, 100 mM NaCl, 100 µM MgCl$_2$, 100 µM MnCl$_2$, 100 µM CaCl$_2$, 1 mg/ml of BSA in 50 mM HEPES, pH 7.5). After removal of the Fc receptor blocking buffer, washing was carried out once with PBS.

2.5 20 µl of binding buffer (100 mM NaCl, 100 µM MgCl$_2$, 100 µM MnCl$_2$, 100 µM CaCl$_2$, 1 mg/ml of BSA in 50 mM HEPES, pH 7.5) were initially introduced, and the substances to be tested were added in 10 µl of binding buffer and incubated for 20 minutes. The controls used were antibodies against VCAM-1 (BBT, No. BBA6) and against VLA-4 (immunotech, No. 0764).

2.6 U937 cells were incubated in Fc receptor blocking buffer for 20 minutes and then added by pipette in a concentration of 1×10$^6$/ml and in an amount of 100 µl per well (final volume 125 µl/well).

2.7 The plates were slowly immersed at an angle of 45° in stop buffer (100 mM NaCl, 100 µM MgCl$_2$, 100 µM MnCl$_2$, 100 µM CaCl$_2$ in 25 mM tris, pH 7.5) and shaken off. The process was repeated.

2.8 50 µl/well of a dye solution (16.7 µg/ml of Hoechst Dye 33258, 4% formaldehyde, 0.5% triton X-100 in PBS) were then incubated on the plates for 15 minutes.

2.9 The plates were shaken off and slowly immersed at an angle of 45° in stop buffer (100 mM NaCl, 100 µM MgCl$_2$, 100 µM MnCl$_2$, 100 µM CaCl$_2$ in 25 mM tris, pH 7.5).

The process was repeated. Then, with the liquid (stop buffer), the plates were measured in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells adherent to the hVCAM-1 (1–3)-IgG remaining on the plate and thus a measure of the ability of the added test substance to inhibit this adhesion. From the inhibition of the adhesion at various concentrations of the test substance, the concentration $IC_{50}$ which leads to a 50% inhibition of adhesion was calculated.

3. Results

Test results which were obtained with compounds of the formula I are listed in Table 13.

TABLE 13

Results of the U937/VCAM-1 cell adhesion test

| Example No. | $IC_{50}$ (nM) | Example No. | $IC_{50}$ (nM) |
|---|---|---|---|
| 1 | 4 | 5 | 5 |
| 6 | 30 | 7 | 2.5 |
| 8 | 3.8 | 9 | 20 |
| 10 | 600 | 11 | 10 |
| 15 | 30 | 16 | 55 |
| 17 | 1.5 | 19 | 3 |
| 20 | 160 | 21 | 520 |
| 22 | 4 | 23 | 16 |
| 24 | 6 | 25 | 6 |
| 26 | 2900 | 27 | 27 |
| 28 | 110 | 29 | 890 |
| 30 | 580 | 34 | 490 |
| 38 | 400 | 41 | 1470 |
| 42 | 470 | 43 | 740 |
| 47 | 0.85 | 49 | 13 |
| 58 | 450 | 61 | 24.5 |
| 62 | 5 | 67 | 2.3 |
| 68 | 300 | 90 | 82 |
| 91 | 210 | 92 | 40 |
| 93 | 7 | 94 | 22 |
| 133 | 1.5 | 184 | 4 |
| 185 | 11 | 186 | 2.9 |
| 187 | 25 | 188 | 1.6 |
| 189 | 50 | 190 | 8 |
| 191 | 122 | 192 | 50 |
| 193 | 15 | 194 | 450 |
| 195 | 23 | 196 | 25 |
| 201 | 25 | 205 | 95 |
| 214 | 17 | 216 | 50 |
| 217 | 40 | 219 | 175 |

B) Leucocyte Adhesion in the Rat

In the leucocyte adhesion model, the effect on adhesion of leucocytes by the compounds of the formula I in venules of the rat is investigated. The leucocyte adhesion in the endothelium of postcapillary venules is regarded as an important step in inflammatory reactions (J. M. Harlan, Blood 1985, 65, 513–525). In the recruitment of leucocytes from the blood in inflamed areas, a well-coordinated dynamic sequence of events takes place, in which chemotactic cytokines and cellular adhesion molecules play an active part. It was found that VCAM-1/VLA-4 interactions play a crucial part in the adhesion and emigration of leucocytes and the increased permeability of vessels for macromolecules which are induced by various mediator substances and cytokines (D. Seiffge, Int. J. Microcirc. 1995, 15, 301–308). In the present model, a generalized inflammation or rheumatoid arthritis which leads to adhesion of the leucocytes and their emigration into diseased organ areas is caused by local or systemic injection of endotoxins, for example zymosan, bacterial toxins such as lipopolysaccharides (LPS) or Freund's adjuvant. The increased adhesion to the endothelium of the venules produced by the endotoxin is determined.

For the determination of leucocyte adhesion, an inverted camera microscope (from Zeiss) which was equipped with a video system was used. Male Sprague-Dawley rats (body weight about 250 g) were injected with zymosan or bacterial endotoxin under a slight halothane premedication. The control animals received an equal volume of 0.9%/strength saline solution. The test substance was then administered to the animals subcutaneously or orally as a single dose or as a multiple dose. To carry out the measurement, the rats were anesthetized by an intramuscular injection of 1.25 g/kg of urethane. They were allowed to breathe spontaneously through a tracheal tube. The body temperature was kept at 37° C. by means of a regulated heating pad. The mesentery was carefully exposed by means of a hypogastric incision on a thermostated (37° C.) window of the microscope stage, and was covered with liquid paraffin at 37° C. The ileocecal area of the mesentery was held in position with three blunt needles and modeling clay. After a 30-minute equilibration time, during which the tissue was allowed to stabilize, the leucocyte adhesion was determined in postcapillary venules of 20–30 µm diameter and about 100 µm length by counting in 2–3 segments of the venules at intervals of 10 minutes for 1 hour. A leucocyte was regarded as adherent to the endothelium if it was stationary for more than 30 seconds. After the experiment, the systemic leucocyte count and the fibrinogen content of the blood was determined. The inhibition of leucocyte adhesion by the test substance is indicated by the decrease (in %) of the number of adherent leucocytes in the treated animals in comparison with the number in the control animals.

C) Delayed-type Hypersensitivity in the Mouse

In the delayed-type hypersensitivity (DTH) model, the antiallergic or antiinflammatory action of the compounds of the formula I is investigated. DTH is an inflammatory reaction of the skin which is induced by sensitization with antigenic substances. In order to determine the corresponding inflammatory reaction and the leucocyte recruitment in the inflamed areas in vivo, the substances are tested on the mouse in the following DTH model (see also T. B. Issekutz, J. Immunol. 1991, 147, 4178–4184).

Groups of female BALB/c mice (body weight about 20 g) were epicutaneously sensitized on a shaved part of the skin with 150 µl of a 3% strength solution of oxazolone, which had been shown to induce a strong inflammatory DTH reaction. 6 days later the reaction was challenged by administration of 20 µl of a 1% strength oxazolone solution on the right ear of the animals. The test substances were administered subcutaneously or orally in each case 44 hours before the challenge of the reaction, 20 hours before the challenge and 4 hours after the challenge. Directly before the challenge of the reaction, and 24 hours after the challenge, the altered ear thickness due to the inflammatory swelling of the ear was measured on the right ear using a Mitutoyo Engineering micrometer. The difference between these two measurements was determined for each animal of the group. The mean values of the differences of an animal group treated with the test substance on the one hand and of an untreated control group on the other hand are compared. The percentage inhibition of ear swelling is indicated.

D) Anti-asthmatic Action in the Guinea-pig

The effect on lung function and the anti-asthmatic action of the compounds of the formula I can be determined in a model on the guinea-pig which follows the method described by G. Moacevic, Arch. Toxicol. 1975, 34, 1. For this purpose, the technical preparations for the investigation are carried out according to the details described by Moacevic. Male albino guinea-pigs having a body weight of 300–500 g are employed. The animals are placed in a plethysmograph (FMI) and three starting values of the parameters respiratory rate and respiratory amplitude are recorded. In this model, an asthmatic respiration is characterized by the decrease of the respiratory amplitude (=lowering of the respiratory volume on account of bronchoconstriction) and the increase in the respiratory frequency (=reflex reaction). This condition is known in asthma patients as dyspnoea.

22 days before the start of the study, the albino guinea-pigs are sensitized with 1 ml per animal of a 0.1% strength ovalbumin solution on two successive days. The experimental asthma attack is induced by inhalation of a 0.3% strength ovalbumin solution for 1 minute. After a recovery phase of 40–60 minutes, the animals inhale the test substance as an aqueous solution. Immediately afterwards, 0.3% strength ovalbumin solution is administered for 1 minute. In the following recovery phase of 30 minutes, the animals breathe normal air. This process is repeated twice. If the asthma attacks become life-threatening, oxygen is administered to the animals.

German Application 1 9751251.8 filed Nov. 19, 1997, for which priority is claimed under 35 U.S.C. §119, is incorporated by reference herein in its entirety.

Although only a few exemplary embodiments of this invention have been described in detail above, those skilled in the art will readily appreciate that many modifications are possible in the exemplary embodiments without materially departing from the teachings and advantages of this invention. Accordingly, all such modifications are intended to be included within the scope of this invention.

What is claimed is:

1. A compound of the formula I

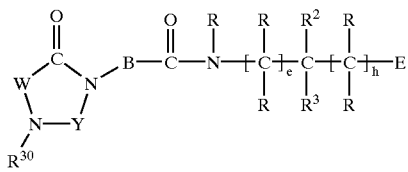

(I)

wherein

W is a divalent radical selected from the group consisting of $R^1$—A—$C(R^{13})$, $R^1$—A—$C(R^{13})$=C,

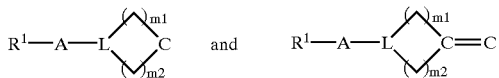

wherein the ring systems

may contain one or two identical or different atoms selected from the group consisting of N, O, and S, may be saturated or mono- or polyunsaturated and may be substituted by 1, 2, or 3 identical or different substituents $R^{13}$ and/or by one or two doubly bonded oxygen atoms and/or sulfur atoms, and wherein L is $C(R^{13})$ or N and wherein m1 and m2 independently of one another are one of the numbers 0, 1, 2, 3, 4, 5 and 6, but the sum m1+m2 is one of the numbers 1, 2, 3, 4, 5, or 6;

Y is a carbonyl group, thiocarbonyl group, or methylene group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl, or a divalent radical of a 5-membered or 6-membered, saturated or unsaturated heterocyle which may contain one or two nitrogen atoms and which may be mono-substituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent radical selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl and $(C_1-C_3)$-alkylenephenyl-$(C_1-C_3)$-alkyl, where the $(C_1-C_6)$-alkylene radical and the $(C_2-C_6)$-alkenylene radical are either unsubstituted or substituted by one or more of the same or different radicals which are selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl or heteroaryl-$(C_1-C_6)$-alkyl optionally substituted in the heteroaryl radical;

E is tetrazolyl, $(R^8O)_2P(O)$, $R^{10}OS(O)_2$, $R^9NHS(O)_2$, $R^6CO$, $R^7CO$, $R^{10}CO$, HCO, $R^8O$—$CH_2$, $R^8CO$—O—$CH_2$, $R^{8a}O$—CO—O—$CH_2$, or $(R^8O)_2P(O)$—O—$CH_2$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where all radicals R are independent of one another and the radicals R may be the same or different;

$R^1$ is hydrogen, $(C_1-C_{10})$-alkyl which may optionally be mono- or polysubstituted by fluorine, $(C_3-C_{12})$-cycloalkyl, $(C_3-C_{12})$-cycloalkyl-$(C_1-C_8)$-alkyl, $R^{21}$—$((C_6-C_{14})$-aryl) optionally substituted in the aryl radical, $(R^{21}$—$((C_6-C_{14})$-aryl))-$(C_1-C_8)$-alkyl optionally substituted in the aryl radical, the radical Het-, Het-$(C_1-C_8)$-alkyl or one of the radicals —X—NH—C(=NH)—$R^{20}$—, $X^1$—NH—$R^{20}$—, $R^{21}O$—$R^{20}$—, $R^{21}N(R^{21})$—$R^{20}$—, $R^{21}C(O)$—, $R^{21}O$—$C(O)$—, $R^{22}N(R^{21})$—$C(O)$—, $R^{22}C(O)$—$N(R^{21})$—, $R^{21}O$—N=, O= and S=;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which may also be substituted in the aryl radical, cyano, hydroxyl, $(C_1-C_6)$-alkoxy, $(C_6-C_{14})$-aryl-$(C_1-C_6)$-alkoxy which may also be substituted in the aryl radical, or amino;

$X^1$ has one of the meanings of X or is R'—NH—C(=N—R''), wherein R' and R'' independently of one another have the meanings of X;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_{10})$-alkyl which may optionally be mono- or polysubstituted by fluorine, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$- tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{21}$, $COOR^{15}$, $CON(CH_3)R^{15}$, or $CONHR^{15}$;

$R^4$ is hydrogen or $(C_1-C_{10})$-alkyl which is unsubstituted or is mono- or polysubstituted by identical or different radicals which are selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{10})$-alkyl)-aminocarbonyl, $(C_6-C_{14})$-aryl-$(C_1-C_8)$-alkoxycarbonyl which may also be substituted in the aryl radical, $(C_1-C_8)$-alkoxycarbonyl, $R^6$—CO, $R^7$—CO, tetrazoyl, and trifluoromethyl;

$R^5$ is optionally substituted $(C_6-C_{14})$-aryl, $(C_6-C_{14})$-aryl-$(C_1-C_8)$-alkyl optionally substituted in the aryl radical, or a radical of an optionally substituted monocyclic or bicyclic, 5-membered to 12 membered heterocyclic ring which may be aromatic, partially saturated or completely saturated and which may contain one, two, or three identical or different heteroatoms selected from the group consisting of nitrogen, oxygen, and sulfur;

$R^6$ is the radical of a natural or unnatural amino acid, imino acid, optionally N-$(C_1-C_8)$-alkylated or N-$((C_6-C_{14})$-aryl-$(C_1-C_8)$-alkylated) azaamino acid which may also be substituted in the aryl radical, or the radical of a dipeptide, tripeptide or tetrapeptide, and their esters and amides, wherein free functional groups may be protected by protective groups and wherein the nitrogen atoms in the amide bonds in the group $R^6$—CO may carry a radical R as a substituent;

$R^7$ is the radical of a 5-membered to 10-membered, saturated monocyclic or polycyclic heterocycle bonded via a nitrogen atom, which may contain one, two, three or four identical or different additional ring heteroatoms selected from the group consisting of oxygen, nitrogen, and sulfur and which may optionally be substituted on carbon atoms and on additional ring nitrogen atoms, wherein additional ring nitrogen atoms may carry identical or different radicals selected from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^8$ is hydrogen, $(C_1-C_{10})$-alkyl, optionally substituted $(C_6-C_{14})$-aryl or $(C_6-C_{14})$-aryl-$(C_1-C_8)$-alkyl which may also be substituted in the aryl radical, where the radicals $R^8$ are independent of one another and may be the same or different;

$R^{8a}$ independently of $R^8$ has one of the meanings of $R^8$ with the exception of hydrogen;

$R^9$ is hydrogen, aminocarbonyl, $(C_1-C_{10})$-alkylaminocarbonyl, $(C_3-C_8)$-cycloalkylaminocarbonyl, optionally substituted $(C_6-C_{14})$-arylaminocarbonyl, $(C_1-C_{10})$-alkyl, optionally substituted $(C_6-C_{14})$-aryl or $(C_3-C_8)$-cycloalkyl;

$R^{10}$ is hydroxyl, $(C_1-C_{10})$-alkoxy, $(C_6-C_{14})$-aryl-$(C_1-C_8)$-alkoxy which may also be substituted in the aryl radical, optionally substituted $(C_6-C_{14})$-aryloxy, $(C_1-C_8)$-alkylcarbonyloxy-$(C_1-C_6)$alkoxy, $(C_6-C_{14})$-arylcarbonyloxy-$(C_1-C_6)$-alkoxy optionally substituted in the aryl radical, $(C_6-C_{14})$-aryl-$(C_1-C_6)$-alkylcarbonyloxy-$(C_1-C_6)$-alkoxy optionally substituted in the aryl radical, $(C_1-C_8)$-alkoxycarbonyloxy-$(C_1-C_6)$-alkoxy, $(C_6-C_{14})$-aryloxycarbonyloxy-$(C_1-C_6)$alkoxy optionally substituted in the aryl radical, $(C_6-C_{14})$-aryl-$(C_1-C_6)$-alkoxycarbonyloxy$(C_1-C_6)$-alkoxy optionally substituted in the aryl radical, amino, mono- or di-$((C_1-C_{10})$-alkyl)-amino or $R^8R^8N$—CO$(C_1-C_6)$-alkoxy, in which the radicals $R^8$ are independent of one another and may be the same or different;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalky-$(C_1-C_8)$-alkyl, optionally substituted $(C_6-C_{14})$-aryl, $(C_6-C_4)$-aryl-$(C_1-C_8)$-alkyl optionally substituted in the aryl radical, optionally substituted heteroaryl or heteroaryl-$(C_1-C_8)$-alkyl optionally substituted in the heteroaryl radical, or the radical $R^{15}$;

$R^{12b}$ is amino, di-$((C_1-C_{10})$-alkyl)-amino or $R^{12a}$—NH;

$R^{13}$ is hydrogen, $(C_1-C_6)$-alkyl which may optionally be mono- or polysubstituted by fluorine, optionally substituted $(C_6-C_{14})$-aryl, $(C_6-C_{14})$-aryl-$(C_1-C_6)$-alkyl optionally substituted in the aryl radical, $(C_3-C_8)$-cycloalkyl or $(C_3-C_8)$-cycloalkyl-$(C_1-C_6)$-alkyl;

$R^{15}$ is $R^{16}$—$(C_1-C_6)$-alkyl or $R^{16}$;

$R^{16}$ is a 6-membered to 24-membered, bicyclic or tricyclic radical which is saturated or partially unsaturated and which may also contain one, two, three or four identical or different heteroatoms selected from the group consisting of nitrogen, oxygen, and sulfur and which may also be substituted by one or more identical or different substituents selected from the group consisting of $(C_1-C_4)$-alkyl and oxo;

$R^{20}$ is a direct bond or a divalent $(C_1-C_6)$-alkylene radical;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, the radical Het or Het-$(C_1-C_8)$-alkyl in which alkyl radicals may be monosubstituted or polysubstituted by fluorine and the radicals $R^{21}$, if they occur more than once, are independent of one another and may be identical or different;

$R^{22}$ is $R^{21}$—, $R^{21}O$—, $R^{21}N(R^{21})$—, $R^{21}C(O)$—, $R^{21}O$—C(O)—, $R^{21}N(R^{21})$—C(O)—, $R^{21}N(R^{21})$—C(=N(R^{21}))$— or $R^{21}C(O)$—N(R^{21})$—;

$R^{30}$ is one of the radicals $R^{32}$—(R)N—CO—N(R)—$R^{31}$, $R^{32}$—(R)N—CS—N(R)—$R^{31}$, $R^{32}$—(R)N—S(O)$_n$—N(R)—$R^{31}$, $R^{32}$—CO—N(R)—$R^{31}$, $R^{32}$—CS—N(R)—$R^{31}$, $R^{32}$—S(O)$_n$—N(R)—$R^{31}$, $R^{32}$—(R)N—CO—$R^{31}$, $R^{32}$—(R)N—CS—$R^{31}$, $R^{32}$—(R)N—S(O)$_n$—$R^{31}$, $R^{32}$—CO—$R^{31}$, $R^{32}$—CS—$R^{31}$, $R^{32}$—S(O)$_n$—$R^{31}$ or $R^{12a}$—O—CO—N(R)—$R^{31}$, where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is a divalent radical —$R^{33}$—$R^{34}$—$R^{35}$—$R^{36}$— where $R^{36}$ is bonded to the nitrogen atom in the imidazolidine ring in the formula I;

$R^{32}$ is hydrogen, $(C_1-C_8)$-alkyl, which may optionally be substituted by 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$- tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical;

$R^{33}$ is a direct bond or a divalent $(C_1-C_6)$-alkylene radical;

$R^{34}$ is a divalent radical selected from the group consisting of $(C_1-C_8)$-alkylene, $(C_3-C_{12})$-cycloalkylene, $(C_6-C_{12})$-bicycloalkylene, $(C_6-C_{12})$-tricycloalkylene, optionally substituted $(C_6-C_{14})$-arylene and optionally substituted heteroarylene;

$R^{35}$ is a direct bond or a divalent $(C_1-C_8)$-alkylene radical;

$R^{36}$ is a direct bond, the group —CO— or the group —S(O)$_n$—;

Het is a radical of a monocyclic or polycyclic, 4-membered to 14-membered, aromatic or nonaromatic ring which contains 1, 2, 3 or 4 identical or different heteroatoms selected from the group consisting of N, O and S as ring members and may optionally be substituted by one or more of the same or different substituents;

e and h independently of one another are 0 or 1;

n is 1 or 2, where the numbers n, if they occur more than once, are independent of one another and may be identical or different;

in any of its stereoisomeric forms or mixtures thereof in any ratios, or a physiologically tolerable salt thereof.

2. A compound of the formula I as claimed in claim 1, in which

W is a divalent radical selected from the group consisting of $R^1$—A—C($R^{13}$), $R^1$—A—C($R^{13}$)=C,

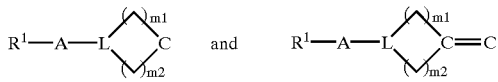

in which the ring systems

may contain one or two identical or different heteroatoms selected from the group consisting of N and O, may be saturated or monounsaturated and may be substituted by 1 or 2 identical or different substituents $R^{13}$ and/or by one or two doubly bonded oxygen atoms, and wherein L is C($R^{13}$) or N and wherein m1 and m2 independently of one another are one of the numbers 0, 1, 2, 3, 4 or 5, but the sum m1+m2 is one of the numbers 1, 2, 3, 4, and 5;

Y is a carbonyl group or thiocarbonyl group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl, or a divalent radical a 5-membered or 6-membered, saturated or unsaturated heterocycle which may contain one or two nitrogen atoms and which may be monosubstituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent methylene radical or ethylene radical, where the methylene radical and the ethylene radical are unsubstituted or substituted by one or more of the same or different radicals which are selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is tetrazoyl, $R^{10}CO$, $R^8O$—$CH_2$, $R^8CO$—O—$CH_2$ or $(R^8O)_2P(O)$—O—$CH_2$;

R is hydrogen, $(C_1-C_8)$-alkyl, $(C_3-C_{10})$-cycloalkyl, $(C_3-C_{10})$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl or heteroaryl-$(C_1-C_6)$-alkyl optionally substituted in the heteroaryl radical, where all radicals R are independent of one another and the radicals R may be the same or different;

$R^1$ is hydrogen, $(C_1-C_{10})$-alkyl which may optionally be monosubstituted or polysubstituted by fluorine, $(C_3-C_{10})$-cycloalkyl, $(C_3-C_{10})$-cycloalkyl-$(C_1-C_6)$-alkyl, $R^{21}$—(($C_6-C_{14}$)-aryl) optionally substituted in the aryl radical, ($R^{21}$—(($C_6-C_{14}$)-aryl))-$(C_1-C_8)$-alkyl optionally substituted in the aryl radical, the radical Het-, Het-$(C_1-C_8)$-alkyl or one of the radicals X—NH—C(=NH)—$R^{20}$—, $X^1$—NH—$R^{20}$—, $R^{21}$O—$R^{20}$—, $R^{22}$C(O)—N($R^{21}$), $R^{22}$N($R^{21}$)—C(O)—, $R^{21}$O—N=, O= and S=;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which may also be substituted in the aryl radical, hydroxyl, $(C_1-C_6)$-alkoxy, $(C_6-C_{14})$-aryl-$(C_1-C_6)$-alkoxy which may also be substituted in the aryl radical, or amino;

$X^1$ has one of the meanings of X or is R'—NH—C(=N—R"), wherein R' and R" independently of one another have the meanings of X;

$R^2$ is hydrogen, $(C_1-C_8)$-alkyl, optionally substituted $(C_6-C_{10})$-aryl or $(C_6-C_{10})$-aryl-$(C_1-C_8)$-alkyl optionally substituted in the aryl radical;

$R^3$ is hydrogen, $(C_1-C_8)$-alkyl which may optionally be substituted by 1 to 8 fluorine atoms, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}$NH, COO$R^{21}$, CON(CH$_3$)$R^4$, CONHR$^4$, COOR$^{15}$, CON(CH$_3$)R$^{15}$, or CONHR$^{15}$;

$R^4$ is hydrogen or $(C_1-C_8)$-alkyl which is unsubstituted or monosubstituted or polysubstituted by the same or different radicals which are selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-(($C_1-C_{10}$)-alkyl)-aminocarbonyl, $(C_6-C_{14})$-aryl-$(C_1-C_8)$-alkoxycarbonyl which may also be substituted in the aryl radical, $(C_1-C_8)$-alkoxycarbonyl, $R^6$—CO, $R^7$—CO, tetrazoyl and trifluoromethyl;

$R^5$ is optionally substituted $(C_6-C_{14})$-aryl, $(C_6-C_{14})$-aryl-$(C_1-C_8)$-alkyl optionally substituted in the aryl radical or a radical of an optionally substituted monocyclic or bicyclic, 5-membered to 12-membered heterocyclic ring, which may be aromatic, partially saturated or completely saturated and which may contain one, two or three identical or different heteroatoms which are selected from the group consisting of nitrogen, oxygen, and sulfur;

$R^6$ is the radical of a natural or unnatural amino acid, imino acid, optionally N-$(C_1-C_8)$-alkylated or N-$((C_6-C_{14})$-aryl-$(C_1-C_8)$-alkylated) azaamino acid which may also be substituted in the aryl radical, or the radical of a dipeptide, tripeptide or tetrapeptide, as well as their esters and amides, wherein free functional groups may be protected by protective groups and in which the nitrogen atoms in the amide bonds in the group $R^6$—CO may carry a radical R as a substituent;

$R^7$ is the radical of a 5-membered to 10-membered, saturated monocyclic or polycyclic heterocycle bonded via a nitrogen atom, which may contain one, two, three or four identical or different additional ring heteroatoms selected from the group consisting of oxygen, nitrogen, and sulfur and which may optionally be substituted on carbon atoms and on additional ring nitrogen atoms, wherein additional ring nitrogen atoms may carry the same or different radicals which are selected from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^8$ is hydrogen, $(C_1-C_6)$-alkyl, optionally substituted $(C_6-C_{10})$-aryl or $(C_6-C_{10})$-aryl-$(C_1-C_6)$-alkyl which may also be substituted in the aryl radical;

$R_{10}$ is hydroxyl, $(C_1-C_8)$-alkoxy, $(C_6-C_{12})$-aryl-$(C_1-C_8)$-alkoxy which may also be substituted in the aryl radical, optionally substituted $(C_6-C_{12})$-aryloxy, $(C_1-C_8)$-alkylcarbonyloxy-$(C_1-C_6)$-alkoxy, $(C_6-C_{12})$-aryl-$(C_1-C_6)$-alkylcarbonyloxy-$(C_1-C_6)$-alkoxy optionally substituted in the aryl radical, $(C_1-C_8)$-alkoxycarbonyloxy-$(C_1-C_6)$-alkoxy, $(C_6-C_{12})$-aryl-$(C_1-C_6)$-alkoxycarbonyloxy-$(C_1-C_6)$-alkoxy optionally substituted in the aryl radical, amino, mono- or di-$((C_1-C_8)$-alkyl)-amino, aminocarbonyl-$(C_1-C_6)$-alkoxy, (mono- or di-$((C_1-C_8)$-alkyl)-amino)-carbonyl-$(C_1-C_6)$-alkoxy, (mono- or di-$((C_6-C_{12})$-aryl-$(C_1-C_6)$-alkyl))amino)-carbonyl-$(C_1-C_6)$-alkoxy or (N-$((C_1-C_8)$-alkyl)-N-$((C_6-C_{12})$-aryl-$(C_1-C_6)$-alkyl)-amino)-carbonyl-$(C_1-C_6)$-alkoxy both optionally substituted in the aryl radical;

$R^{11}$ is hydrogen, $R^{12a}$, $R^{12a}$—CO, $R^{12a}$—O—CO, $R^{12b}$—CO, $R^{12b}$—CS or $R^{12a}$—S(O)$_2$;

$R^{12a}$ is $(C_1-C_{10})$-alkyl, $(C_2-C_8)$-alkenyl, $(C_2-C_8)$-alkynyl, $(C_5-C_{10})$-cycloalkyl, $(C_5-C_{10})$-cycloalky-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-$((C_1-C_{10})$-alkyl)-amino or $R^{12a}$—NH;

$R^{13}$ is hydrogen or $(C_1-C_6)$-alkyl;

$R^{15}$ is $R^{16}$—$(C_1-C_6)$-alkyl or $R^{16}$;

$R^{16}$ is a 6-membered to 14-membered, bicyclic or tricyclic radical which is saturated or partially unsaturated and which may also contain one, two, three or four identical or different heteroatoms selected from the group consisting of nitrogen, oxygen, and sulfur and which may also be substituted by one or more identical or different substituents selected from the group consisting of $(C_1-C_4)$-alkyl and oxo;

$R^{20}$ is a direct bond or $(C_1-C_4)$-alkylene;

$R^{21}$ is hydrogen, $(C_1-C_8)$-alkyl, $(C_3-C_{10})$-cycloalkyl, $(C_3-C_{10})$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, the Het or Het-$(C_1-C_6)$-alkyl, in which alkyl radicals may be monosubstituted or polysubstituted by fluorine and the radicals $R^{21}$, if they occur more than once, may be identical or different;

$R^{22}$ is $R^{21}$—, $R^{21}N(R^{21})$—, $R^{21}C(O)$, $R^{21}O$—C(O)— or $R^{21}N(R^{21})$—C(=N($R^{21}$))—;

$R^{30}$ is one of the radicals $R^{32}$—(R)N—CO—N(R)—$R^{31}$, $R^{32}$(R)N—CS—N(R)—$R^{31}$, $R^{32}$—(R)N—S(O)$_n$—N(R)—$R^{31}$, $R^{32}$—CO—N(R)—$R^{31}$, $R^{32}$—S(O)$_n$—N(R)—$R^{31}$, $R^{32}$—(R)N—CO—$R^{31}$, $R^{32}$—(R)N—S(O)$_n$—$R^{31}$, $R^{32}$—CO—$R^{31}$, $R^{32}$—S(O)$_n$—$R^{31}$ or $R^{12a}$—O—CO—N(R)—$R^{31}$ where $R^{30}$ cannot be $R^{32}$—CO—N(R)—$R^{31}$ if at the same time W is $R^1$—A—C($R^{13}$), A is a direct bond and $R^1$ and $R^{13}$ are hydrogen;

$R^{31}$ is a divalent radical —$R^{33}$—$R^{34}$—$R^{35}$—$R^{36}$ where $R^{36}$, —is bonded to the nitrogen atom in the imidazolidine ring in the formula I;

$R^{32}$ is hydrogen, $(C_1-C_8)$-alkyl, which may optionally be substituted by 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical;

$R^{33}$ is a direct bond or a divalent $(C_1-C_6)$-alkylene radical;

$R^{34}$ is a divalent radical selected from the group consisting of $(C_1-C_8)$-alkylene, $(C_5-C_{10})$-cycloalkylene, $(C_6-C_{12})$-bicycloalkylene, optionally substituted $(C_6-C_{14})$-arylene and optionally substituted heteroarylene;

$R^{35}$ is a direct bond or a divalent $(C_1-C_8)$-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1, 2, 3 or 4 identical or different heteroatoms selected from the group consisting of N and O as ring members and which may optionally be substituted by one or more identical or different substituents;

e and h independently of one another are 0 or 1;

n is 1 or 2, where the numbers n, if they occur more than once, are independent of one another and may be identical or different;

in any of its stereoisomeric forms or mixtures thereof in any ratios, or a physiologically tolerable salt thereof.

3. A compound of the formula I as claimed in claim 1, wherein

W is a divalent radical selected from the group consisting of $R^1$—A—$C(R^{13})$ and

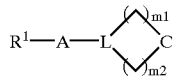

wherein the ring systems

may contain one or two identical or different heteroatoms selected from the group consisting of N and O, may be saturated or monosaturated and may be substituted by 1 or 2 identical or different substituents $R^{13}$ and/or by one or two doubly bonded oxygen atoms, and wherein L is $C(R^{13})$ or N and wherein m1 and m2 independently of one another are one of the numbers 0, 1, 2, 3 and 4, the sum m1+m2, however, is one of the numbers 1, 2, 3 and 4;

Y is a carbonyl group or thiocarbonyl group;

A is a direct bond, one of the divalent radicals $(C_1-C_6)$-alkylene, $(C_5-C_6)$-cycloalkylene, phenylene, phenylene-$(C_1-C_4)$-alkyl, or a divalent radical of a 5-membered or 6-membered, saturated or unsaturated heterocycle which may contain one or two nitrogen atoms and which may be monosubstituted or disubstituted by $(C_1-C_6)$-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or substituted by one or more identical or different radicals which are selected from the group consisting of $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^{10}CO$, HO—$CH_2$ or $R^8CO$—O—$CH_2$;

R is hydrogen or $(C_1-C_8)$-alkyl, where all radicals R are independent of one another and the radicals R may be the same or different;

$R^1$ is hydrogen, $(C_1-C_{10})$-alkyl which may optionally be monosubstituted or polysubstituted by fluorine, $R^{21}$—$((C_6-C_{10})$-aryl) optionally substituted in the aryl radical, $(R^{21}-((C_6-C_{10})$-aryl))-$(C_1-C_6)$-alkyl optionally substituted in the aryl radical, the radical Het-, Het-$(C_1-C_6)$-alkyl or one of the radicals X—NH—C(=NH)—$R^{20}$—, $X^1$—NH—$R^{20}$—, $R^{22}N(R^{21})$—C(O)—, O= and S=;

X is hydrogen, $(C_1-C_6)$-alkyl, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl, optionally substituted $(C_6-C_{10})$-arylcarbonyl, optionally substituted $(C_6-C_{10})$-aryloxycarbonyl, $(C_6-C_{14})$-aryl-$(C_1-C_6)$-alkoxycarbonyl which may also be substituted in the aryl radical, hydroxyl, $(C_1-C_6)$-alkoxy, or amino;

$X^1$ has one of the meanings of X or is R'—NH—C(=N—R''), wherein R' and R'' independently of one another have the meanings of X;

$R^2$ is hydrogen or $(C_1-C_8)$-alkyl;

$R^3$ is hydrogen, $(C_1-C_8)$-alkyl which may optionally be substituted by 1 to 6 fluorine atoms, optionally substituted $(C_6-C_{12})$-aryl, $(C_6-C_{12})$-aryl-$(C_1-C_6)$-alkyl optionally substituted in the aryl radical, optionally substituted heteroaryl, heteroaryl-$(C_1-C_6)$-alkyl optionally substituted in the heteroaryl radical, $(C_3-C_8)$-cycloalkyl, $(C_3-C_8)$-cycloalkyl-$(C_1-C_6)$-alkyl, $(C_6-C_{12})$-bicycloalkyl, $(C_6-C_{12})$-bicycloalkyl-$(C_1-C_6)$-alkyl, $(C_6-C_{12})$-tricycloalkyl, $(C_6-C_{12})$-tricycloalkyl-$(C_1-C_6)$-alkyl, $(C_2-C_8)$-alkenyl, $(C_2-C_8)$-alkynyl, $R^{11}NH$, $COOR^{21}$, $CON(CH_3)R^4$, $CONHR^4$, $CON(CH_3)R^{15}$ or $CONHR^{15}$;

$R^4$ is $(C_1-C_8)$-alkyl which is unsubstituted or monosubstituted or disubstituted by identical or different radicals which are selected from the group consisting of hydroxyl, $(C_1-C_8)$-alkoxy, $R^5$, optionally substituted $(C_3-C_8)$-cycloalkyl, hydroxycarbonyl, aminocarbonyl, $(C_6-C_{10})$-aryl-$(C_1-C_4)$-alkoxycarbonyl which may also be substituted in the aryl radical, $(C_1-C_6)$-alkoxycarbonyl, $R^6$—CO, $R^7$—CO, tetrazoyl, and trifluoromethyl;

$R^5$ is optionally substituted $(C_6-C_{12})$-aryl, $(C_6-C_{12})$-aryl-$(C_1-C_8)$-alkyl optionally substituted in the aryl radical or a radical of an optionally substituted monocyclic or bicyclic, 5-membered to 12-membered heterocyclic ring, which may be aromatic, partially saturated or completely saturated and which may contain one, two or three identical or different heteroatoms selected from the group consisting of nitrogen, oxygen, and sulfur;

$R^6$ is the radical of a natural or unnatural amino acid, imino acid, optionally N-$(C_1-C_8)$-alkylated or N-$((C_6-C_{12})$-aryl-$(C_1-C_8)$-alkylated) azaamino acid which may also be substituted in the aryl radical, or the radical of a dipeptide or tripeptide as well as their esters and amides, wherein free functional groups may be protected by protective groups and wherein the nitrogen atoms in the amide bonds in the group $R^6$—CO may carry a radical R as a substituent;

$R^7$ is the radical of 5-membered to 7-membered, saturated monocyclic or bicyclic heterocycle bonded via a nitrogen atom, which may contain one, two, three or four identical or different additional ring heteroatoms selected from the group consisting of oxygen, nitrogen, and sulfur and which may optionally be substituted on carbon atoms and on additional ring nitrogen atoms, wherein additional ring nitrogen atoms may carry the same or different radicals which are selected from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_6)$-alkyl, $(C_3-C_8)$-cycloalkyl, $(C_3-C_8)$-cycloalkyl-$(C_1-C_8)$-alkyl, optionally substituted $(C_6-C_{10})$-aryl or $(C_6-C_{10})$-aryl-$(C_1-C_4)$-alkyl optionally substituted in the aryl radical;

$R^8$ is hydrogen, $(C_1-C_6)$-alkyl or phenyl-$(C_1-C_4)$-alkyl optionally substituted in the phenyl radical;

$R^{10}$ is hydroxyl, $(C_1-C_8)$-alkoxy, $(C_6-C_{10})$-aryl-$(C_1-C_6)$-alkoxy which may also be substituted in the aryl radical, optionally substituted $(C_6-C_{10})$-aryloxy, $(C_1-C_6)$-alkylcarbonyloxy-$(C_1-C_6)$-alkoxy, $(C_1-C_6)$-alkoxycarbonyloxy-$(C_1-C_6)$-alkoxy, amino, mono- or di-$((C_1-C_6)$-alkyl)-amino, aminocarbonyl-$(C_1-C_6)$- alkoxy or (mono- or di-(($C_1$–$C_6$)-alkyl)-amino)-carbonyl-($C_1$–$C_6$)-alkoxy;

$R^{11}$ is hydrogen, $R^{12a}$, $R^{12a}$—CO, $R^{12a}$—O—CO, $R^{12b}$—CO or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalky-($C_1$–$C_8$)-alkyl, optionally substituted ($C_6$–$C_{14}$)-aryl, ($C_6$–$C_4$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, or the radical $R^{15}$;

$R^{12b}$ is amino, di-(($C_1$–$C_{10}$)-alkyl)-amino or $R^{12a}$—NH;

$R^{13}$ is hydrogen or ($C_1$–$C_6$)-alkyl;

$R^{15}$ is $R^{16}$—($C_1$–$C_6$)-alkyl or $R^{16}$;

$R^{16}$ is a 6-membered to 14-membered, bicyclic or tricyclic radical which is saturated or partially unsaturated and which may also contain one, two, three or four identical or different heteroatoms selected from the group consisting of nitrogen, oxygen, and sulfur and which may also be substituted by one or more identical or different substituents selected from the group consisting of ($C_1$–$C_4$)-alkyl and oxo;

$R^{20}$ is a direct bond or ($C_1$–$C_2$)-alkylene;

$R^{21}$ is hydrogen, ($C_1$–$C_6$)-alkyl, ($C_3$–$C_6$)-cycloalkyl, ($C_3$–$C_6$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, the radical Het or Het-($C_1$–$C_4$)-alkyl, in which alkyl radicals may be monosubstituted or polysubstituted by fluorine and the radicals $R^{21}$, if they occur more than once, may be the same or different;

$R^{22}$ is $R^{21}$—, $R^{21}$N($R^{21}$)— or $R^{21}$N($R^{21}$)—C(=N($R^{21}$))—;

$R^{30}$ is one of the radicals $R^{32}$(R)N—CO—N(R)—$R^{31}$, $R^{32}$(R)N—CS—N(R)—$R^{31}$, $R^{32}$—CO—N(R)—$R^{31}$ or $R^{32}$—(R)N—CO—$R^{31}$, where $R^{30}$ cannot be $R^{32}$—CO—N(R)$R^{31}$ if at the same time W is $R^1$—A—C($R^{13}$), A is a direct bond and $R^1$ and $R^{13}$ are hydrogen;

$R^{31}$ is a divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_1$–$C_6$)-alkyl which may optionally be substituted by 1 to 6 fluorine atoms, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl or heteroaryl-($C_1$–$C_6$)-alkyl optionally substituted in the heteroaryl radical;

$R^{33}$ is a direct bond or a divalent ($C_1$–$C_4$)-alkylene radical;

$R^{34}$ is a divalent radical selected from the group consisting of ($C_1$–$C_6$)-alkylene, ($C_5$–$C_6$)-cycloalkylene, optionally substituted ($C_6$–$C_{10}$)-arylene and optionally substituted heteroarylene;

$R^{35}$ is a direct bond or a divalent ($C_1$–$C_4$)-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1 or 2 identical or different heteroatoms selected from the group consisting of N and O as ring members and which may optionally be substituted by one or more, identical or different substituents;

e and h independently of one another are 0 or 1;

n is 1 or 2;

in any of its stereoisomeric forms or mixtures thereof in any ratios, or a physiologically tolerable salt thereof.

4. A compound of the formula I as claimed in claim 1, in which

W is the divalent radical $R^1$—A—C($R^{13}$),

Y is a carbonyl group;

A is a direct bond, one of the divalent radicals ($C_1$–$C_6$)-alkylene, phenylene, phenylene-($C_1$–$C_2$)-alkyl, or a divalent radical of a 5-membered or 6-membered, saturated or unsaturated heterocycle which may contain one or two nitrogen atoms and which may be monosubstituted or disubstituted by ($C_1$–$C_6$)-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or substituted by a radical selected from the group consisting of ($C_1$–$C_8$)-alkyl, ($C_2$–$C_8$)-alkenyl, ($C_2$–$C_8$)-alkynyl, ($C_3$–$C_6$)-cycloalkyl, ($C_3$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

E is $R^{10}$CO, HO—$CH_2$ or $R^8$CO—O—$CH_2$;

R is hydrogen or ($C_1$–$C_8$)-alkyl where all radicals R are independent of one another and the radicals R may be identical or different;

$R^1$ is hydrogen, ($C_1$–$C_{10}$)-alkyl which may optionally be monosubstituted or polysubstituted by fluorine, $R^{21}$—(($C_6$–$C_{10}$)-aryl) optionally substituted in the aryl radical, ($R^{21}$—(($C_6$–$C_{10}$)-aryl))-($C_1$–$C_6$)-alkyl optionally substituted in the aryl radical, the radical Het-, Het-($C_1$–$C_4$)-alkyl or one of the radicals X—NH—C(=NH)—$R^{20}$—, $X^1$—NH—$R^{20}$—, and O=;

X is hydrogen, ($C_1$–$C_6$)-alkyl, ($C_1$–$C_6$)-alkylcarbonyl, ($C_1$–$C_6$)-alkoxycarbonyl, ($C_1$–$C_6$)-alkylcarbonyloxy-($C_1$–$C_6$)-alkoxycarbonyl, optionally substituted ($C_6$–$C_{10}$)-arylcarbonyl, optionally substituted ($C_6$–$C_{10}$)-aryloxycarbonyl, ($C_6$–$C_{14}$)-aryl-($C_1$–$C_6$)-alkoxycarbonyl which may also be substituted in the aryl radical, hydroxyl, ($C_1$–$C_6$)-alkoxy, or amino;

$X^1$ has one of the meanings of X or is R'—NH—C(=N—R''), wherein R' and R'' independently of one another have the meanings of X;

$R^2$ is hydrogen or ($C_1$–$C_6$)-alkyl;

$R^3$ is hydrogen, ($C_1$–$C_8$)-alkyl which may optionally be substituted by 1 to 6 fluorine atoms, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, ($C_3$–$C_8$)-cycloalkyl, ($C_3$–$C_8$)-cycloalkyl-($C_1$–$C_4$)-alkyl, ($C_6$–$C_{12}$)-bicycloalkyl, ($C_6$–$C_{12}$)-bicycloalkyl-($C_1$–$C_4$)-alkyl, ($C_6$–$C_{12}$)-tricycloalkyl, ($C_6$–$C_{12}$)-tricycloalkyl-($C_1$–$C_4$)-alkyl, ($C_2$–$C_8$)-alkenyl, ($C_2$–$C_8$)-alkynyl, $R^{11}$NH, COO$R^{21}$, CON(CH$_3$)$R^4$, CONH$R^4$, CON(CH$_3$)$R^{15}$ or CONH$R^{15}$;

$R^4$ is ($C_1$–$C_6$)-alkyl which is unsubstituted or monosubstituted or disubstituted by the same or different radicals which are selected from the group consisting of hydroxyl, ($C_1$–$C_8$)-alkoxy, $R^5$, optionally substituted ($C_3$–$C_8$)-cycloalkyl, hydroxycarbonyl, aminocarbonyl, ($C_6$–$C_{10}$)-aryl-($C_1$–$C_4$)-alkoxycarbonyl, which may also be substituted in the aryl radical, ($C_1$–$C_6$)-alkoxycarbonyl, $R^6$—CO, $R^7$—CO, tetrazoyl and trifluoromethyl;

$R^5$ is optionally substituted ($C_6$–$C_{10}$)-aryl, ($C_6$–$C_{10}$)-aryl-($C_1$–$C_4$)-alkyl optionally substituted in the aryl radical or a radical of an optionally substituted monocyclic or bicyclic, 5-membered to 12-membered heterocyclic ring, which may be aromatic, partially saturated or completely saturated and which may contain one, two or three identical or different heteroatoms selected from the group consisting of nitrogen, oxygen, and sulfur;

$R^6$ is the radical of a natural or unnatural amino acid or the radical of a dipeptide or tripeptide, as well as their esters and amides, wherein free functional groups may be protected by protective groups and wherein the nitrogen atoms in the amide bonds in the group $R^6$—CO may carry a radical R as a substituent;

$R^7$ is the radical of a 5-membered to 7-membered, saturated monocyclic heterocycle bonded via a nitrogen atom, which may contain one or two identical or different additional ring heteroatoms selected from the group consisting of oxygen, nitrogen, and sulfur and which may optionally be substituted on carbon atoms and on additional ring nitrogen atoms, wherein additional ring nitrogen atoms may carry the same or different radicals which are selected from the group consisting of hydrogen, $R^h$, HCO, $R^h$CO, $R^h$O—CO, HO—CO—($C_1$–$C_4$)-alkyl and $R^h$O—CO—($C_1$–$C_4$)-alkyl as substituents and $R^h$ is ($C_1$–$C_4$)-alkyl, optionally substituted ($C_6$–$C_{10}$)-aryl or ($C_6$–$C_{10}$)-aryl-($C_1$–$C_4$)-alkyl optionally substituted in the aryl radical;

$R^8$ is hydrogen, ($C_1$–$C_6$)-alkyl or phenyl-($C_1$–$C_4$)-alkyl optionally substituted in the phenyl radical;

$R^{10}$ is hydroxyl, ($C_1$–$C_8$)-alkoxy, ($C_6$–$C_{10}$)-aryl-($C_1$–$C_6$)-alkoxy which may also be substituted in the aryl radical, optionally substituted ($C_6$–$C_{10}$)-aryloxy, ($C_1$–$C_6$)-alkylcarbonyloxy-($C_1$–$C_6$)-alkoxy, ($C_1$–$C_6$)-alkoxycarbonyloxy-($C_1$–$C_6$)-alkoxy, amino, mono- or di-(($C_1$–$C_6$)-alkyl)-amino, aminocarbonyl-($C_1$–$C_6$)-alkoxy or (mono- or di-(($C_1$–$C_6$)-alkyl)-amino)-carbonyl-($C_1$–$C_6$)-alkoxy;

$R^{11}$ is hydrogen, $R^{12a}$, $R^{12a}$—CO, $R^{12a}$—O—CO, $R^{12b}$—CO or $R^{12a}$—S(O)$_2$;

$R^{12a}$ is ($C_1$–$C_8$)-alkyl, ($C_2$–$C_8$)-alkenyl, ($C_2$–$C_8$)-alkynyl, ($C_5$–$C_6$)-cycloalkyl, ($C_5$–$C_6$)-cycloalky-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, or the radical $R^{15}$;

$R^{12b}$ is amino, di-(($C_1$–$C_8$)-alkyl)-amino or $R^{12a}$—NH;

$R^{13}$ is hydrogen or ($C_1$–$C_6$)-alkyl;

$R^{15}$ is $R^{16}$—($C_1$–$C_6$)-alkyl or $R^{16}$;

$R^{16}$ is a 6-membered to 12-membered, bicyclic or tricyclic radical which is saturated or partially unsaturated and which may also contain one, two, three or four identical or different heteroatoms selected from the group consisting of nitrogen, oxygen, and sulfur and which may also be substituted by one or more of the same or different substituents which are selected from the group consisting of ($C_1$–$C_4$)-alkyl and oxo;

$R^{20}$ is a direct bond or methylene;

$R^{21}$ is hydrogen, ($C_1$–$C_6$)-alkyl, optionally substituted ($C_6$–$C_{10}$)-aryl, ($C_6$–$C_{10}$)-aryl-($C_1$–$C_2$)-alkyl optionally substituted in the aryl radical, the radical Het or Het-($C_1$–$C_2$)-alkyl, in which alkyl radicals may be monosubstituted to tetrasubstituted by fluorine and the radicals $R^{21}$, if they occur more than once, may be the same or different;

$R^{30}$ is one of the radicals $R^{32}$(R)N—CO—N(R)—$R^{31}$ or $R^{32}$(R)N—CS—N(R)—$R^{31}$, $R^{31}$ is the divalent radical selected from the group consisting of ($C_1$–$C_6$)-alkylene, optionally substituted ($C_6$–$C_{10}$)-arylene, ($C_6$–$C_{10}$)-arylene-($C_1$–$C_4$)-alkyl optionally substituted in the arylene radical, ($C_5$–$C_6$)-cycloalkylene, ($C_5$–$C_6$)-cycloalkylene-($C_1$–$C_4$)-alkyl, optionally substituted heteroarylene or heteroarylene-($C_1$–$C_4$)-alkyl optionally substituted in the heteroarylene radical, where in the case of the arylenealkyl radical, of the cycloalkylenealkyl radical and of the heteroarylenealkyl radical the alkyl group is bonded to the nitrogen atom in the imidazolidine ring of formula I;

$R^{32}$ is hydrogen, ($C_1$–$C_6$)-alkyl which may optionally be substituted by 1 to 6 fluorine atoms, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl or heteroaryl-($C_1$–$C_4$)-alkyl optionally substituted in the heteroaryl radical;

Het is a radical of a monocyclic or polycyclic, 5-membered to 10-membered, aromatic or nonaromatic ring which contains 1 or 2 identical or different heteroatoms selected from the group consisting of N and O as ring members and which may optionally be substituted by one or more, identical or different substituents;

e and h independently of one another are 0 or 1;

in any of its stereoisomeric forms or mixtures thereof in any ratios, or a physiologically tolerable salt thereof.

5. A compound of the formula I as claimed in claim 1, in which W has a meaning other than $CH_2$, in any of its stereoisomeric forms or mixtures thereof in any ratios, or a physiologically tolerable salt thereof.

6. A compound of the formula I as claimed in claim 1, wherein B is unsubstituted methylene or methylene which is substituted by ($C_1$–$C_6$)-alkyl or ($C_3$–$C_6$)-cycloalkyl-($C_1$–$C_2$)-alkyl, in any of its stereoisomeric forms or mixtures thereof in any ratios, or its physiologically tolerable salt.

7. A compound of the formula I as claimed in claim 1, wherein $R^{30}$ is one of the radicals $R^{32}$—(R)N—CO—N(R)—$R^{31}$ or $R^{32}$—(R)N—CS—N(R)—$R^{31}$, in any of its stereoisomeric forms or mixtures thereof in any ratios, or its physiologically tolerable salt.

8. A compound of the formula I as claimed in claim 1, wherein $R^{30}$ is the radical $R^{32}$—NH—CO—NH—$R^{31}$ and, therein, $R^{31}$ is the divalent radical-(1,4-phenylene)-$CH_2$— in which the methylene group is bonded to the nitrogen atom in the imidazolidine ring, and $R^{32}$ is unsubstituted or substituted phenyl, in any of its stereoisomeric forms or mixtures thereof in any ratios, or its physiologically tolerable salt.

9. A compound of the formula I as claimed in claim 1, wherein W has a meaning other than $CH_2$, B is unsubstituted methylene or methylene which is substituted by ($C_1$–$C_6$)-alkyl or ($C_3$–$C_6$)-cycloalkyl-($C_1$–$C_2$)-alkyl, $R^{30}$ is the radical $R^{32}$NH—CO—NH—$R^{31}$, $R^{31}$ is the divalent radical-(1,4)-phenylene-$CH_2$— in which the methylene group is bonded to the nitrogen atom in the imidazolidine ring, $R^{32}$ is unsubstituted or substituted phenyl, and the group —NR—[C(R)(R)]$_e$—C(R$^2$)(R$^3$)—[C(R)(R)]$_h$—E in the formula I is the group —NH—CH(R$^3$)—CH$_2$—E, in any of its stereoisomeric forms or mixtures in any ratios, or ts physiologically tolerable salt.

10. A compound of the formula I as claimed in claim 4, wherein B is unsubstituted methylene or methylene which is substituted by (C$_1$–C$_6$)-alkyl or (C$_3$–C$_6$)-cycloalkyl-(C$_1$–C$_6$)-alkyl, in any of its stereoisomeric forms or mixtures in all ratios, or a physiologically tolerable salt thereof.

11. A compound of the formula I as claimed in claim 4, in which R$^{30}$ is the radical R$^{32}$—NH—CO—NH—R$^{31}$ and, therein, R$^{31}$ is the divalent radical-(1,4-phenylene)-CH$_2$— in which the methylene group is bonded to the nitrogen atom in the imidazolidine ring, and R$^{32}$ is unsubstituted or substituted phenyl, in any of its stereoisomeric forms or mixtures thereof in all ratios, or a physiologically tolerable salt thereof.

12. A compound of the formula I as claimed in claim 4, wherein W has a meaning other than CH$_2$, B is unsubstituted methylene or methylene which is substituted by (C$_1$–C$_6$)-alkyl or (C$_3$–C$_6$)-cycloalkyl-(C$_1$–C$_2$)-alkyl, R$^{30}$ is the radical R$^{32}$NH—CO—NH—R$^{31}$, R$^{31}$ is the divalent radical —(1,4-phenylene)-CH$_2$— in which the methylene group is bonded to the nitrogen atom in the imidazolidine ring, R$^{32}$ is unsubstituted or substituted phenyl, and the group —NR—[C(R)(R)]$_e$—C(R$^2$)(R$^3$)—[C(R)(R)]$_h$—E in the formula I is the group —NH—CH(R$^3$)—CH$_2$—E, in any of its stereoisomeric forms or mixtures thereof in any ratios, or a physiologically tolerable salt thereof.

13. A process for the preparation of a compound of the formula I as claimed in claim 1, which comprises carrying out a fragment condensation of a compound of the formula II

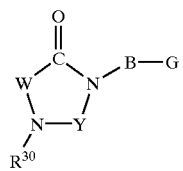

(II)

with a compound of the formula III,

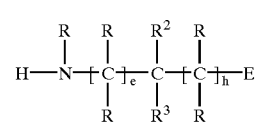

(III)

where, in the formulae II and III, the groups W, Y, B, E, R, R$^2$, R$^3$ and R$^{30}$ as well as e and h are defined as indicated in claim 1, or alternatively functional groups may be present in protected form or in the form of precursors, and where G is hydroxycarbonyl, alkoxycarbonyl, or activated carboxylic acid derivatives.

14. A pharmaceutical composition which contains an effective amount of one or more compounds of the formula I as claimed in claim 1 or a physiologically tolerable salt thereof and a pharmaceutically innocuous excipient.

15. A method for the therapy or prophylaxis of inflammation in a mammal in need thereof comprising administering to the mammal a composition according to claim 14.

16. A method for the therapy or prophylaxis of arthritis, rheumatoid arthritis, polyarthritis, inflammatory bowel disease, systemic lupus erythematosus, multiple sclerosis or an inflammatory disorder of the central nervous system, in a mammal in need thereof, comprising administering to the mammal, a composition according to claim 14.

17. A method for the therapy or prophylaxis of asthma or an allergy in a mammal in need thereof, comprising administering to the mammal, a composition according to claim 14.

18. A method for the therapy or prophylaxis of cardiovascular disorder, arteriosclerosis, restenosis, of diabetes, damage to an organ transplant, an immune disorder, an autoimmune disorder, tumor growth or formation, tumor metastases or malaria, in a mammal in need thereof, comprising administering to the mammal a composition according to claim 14.

19. A method for inhibiting adhesion and/or migration of leucocytes or inhibiting a VLA-4 receptor in a mammal in need thereof, comprising administering to a mammal a composition according to claim 14.

\* \* \* \* \*